(12) United States Patent
Gong et al.

(10) Patent No.: US 11,028,174 B1
(45) Date of Patent: Jun. 8, 2021

(54) BIFUNCTIONAL MOLECULES TARGETING PD-L1 AND TGF-β

(71) Applicant: Lepu Biopharma Co., Ltd., Shanghai (CN)

(72) Inventors: Wenci Gong, Shanghai (CN); Yiwei Tou, Beijing (CN)

(73) Assignee: Lepu Biopharma Co., Ltd., Shanghai (CN)

( * ) Notice: Subject to any disclaimer, the term of this patent is extended or adjusted under 35 U.S.C. 154(b) by 0 days.

(21) Appl. No.: 17/006,517

(22) Filed: Aug. 28, 2020

(30) Foreign Application Priority Data

Jul. 28, 2020 (WO) ................ PCT/CN2020/105286

(51) Int. Cl.
| | | |
|---|---|---|
| *C07K 16/00* | (2006.01) | |
| *A61K 39/395* | (2006.01) | |
| *C07K 16/28* | (2006.01) | |
| *C07K 14/71* | (2006.01) | |
| *A61P 35/00* | (2006.01) | |
| *A61K 39/00* | (2006.01) | |

(52) U.S. Cl.
CPC .......... *C07K 16/2827* (2013.01); *A61P 35/00* (2018.01); *C07K 14/71* (2013.01); *A61K 2039/505* (2013.01); *C07K 2317/24* (2013.01); *C07K 2317/33* (2013.01); *C07K 2317/565* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 9,676,863 | B2 | 6/2017 | Lu |
| 9,809,637 | B2 | 11/2017 | Kumar et al. |
| 2015/0056199 | A1 | 2/2015 | Kumar et al. |
| 2019/0169621 | A1 | 6/2019 | Govindappa et al. |
| 2020/0157180 | A1 | 5/2020 | Gu et al. |

*Primary Examiner* — Mark Halvorson
(74) *Attorney, Agent, or Firm* — Sheppard Mullin Richter & Hampton LLP

(57) ABSTRACT

Provided are anti-PD-L1 antibodies with superior activities in blocking the PD-1 and PD-L1 interactions. Also provided are multifunctional molecules that include the anti-PD-L1 antibodies or fragments thereof fused to an extracellular domain of human TGF-beta receptor type-2.

16 Claims, 29 Drawing Sheets

Specification includes a Sequence Listing.

BIFUNCTIONAL MOLECULES TARGETING PD-L1 AND TGF-β

CROSS REFERENCE TO RELATED APPLICATIONS

This application claims priority to PCT/CN2020/105286, filed Jul. 28, 2020, which is hereby incorporated by reference in its entirety.

SEQUENCE LISTING

The instant application contains a Sequence Listing which has been filed electronically in ASCII format and is hereby incorporated by reference in its entirety. Said ASCII copy, created on Aug. 28, 2020, is named 320293US_ST25.txt and is 112,479 bytes in size.

BACKGROUND

The exciting advances in cancer immunotherapy in recent years have led to paradigm shifts in oncology. The most noticeable results have been with T-cell-based therapies including immune checkpoint inhibitors (ICI), genetically engineered T-cells and bispecific antibodies (BsAb). T-cells represent a major class of immunosurveillance and tumor eradication with exquisite specificity and long-term memory. However, in the tumor microenvironment, T-cells can become exhausted or tolerized to tumor cells. T-cell exhaustion is commonly associated with overexpression of inhibitory receptors, including programmed death receptor-1 (PD-1), cytotoxic T lymphocyte antigen-4 (CTLA-4), lymphocyte-activation gene-3 (LAG-3), T-cell immunoglobulin domain and mucin domain-3 (TIM-3), IL-10 receptor, and killer immunoglobulin receptors.

Monoclonal antibody (mAb) based therapies to counteract these checkpoint molecules can remove the brake that restrains tumor-infiltrating T-cells, thereby achieving significant clinical benefits in different malignancies. For instance, blocking PD-1/PD-L1 interactions can enhance immune normalization and reinforce anticancer responses. However, the noticeable deficiency of PD-1/PD-L1 blockades is inconsistency across a homogeneous study population with similar tumor characteristics. Also, PD-1/PD-L1 blockade treatments may also cause certain inflammatory side effects in some patients. The limitations of monotherapy with PD-1/PD-L1 blockades and the lack of promising alternatives has made it necessary to seek combination treatment methods which can activate antitumor immunity and enhance treatment efficacy.

M7824 (bintrafusp alfa) is a bifunctional protein composed of a monoclonal antibody against programmed death ligand 1 (PD-L1) fused to the extracellular domain of human transforming growth factor-β (TGF-β) receptor II, which functions as a "trap" for all three TGF-θ isoforms. The PD-L1 portion is the based on avelumab, which has been approved for the treatment of Merkel cell carcinoma and urothelial cancer. Current clinical data show, however, that the use of M7824 is associated with undesired skin growth and the overall response rate was only about 35% to 40% in a phase II trial for patients with HPV-positive malignancies. Improved therapies are needed, therefore.

SUMMARY

The present disclosure provides, in some embodiments, bifunctional molecules that target both the PD-L1 protein and TGF-β. The disclosed PD-L1 targeting unit, comprised of an anti-PD-L1 antibody, is fused to an extracellular domain of human transforming growth factor-β (TGF-β) receptor II which functions as a trap for TGF-β. Experimental data show that these new bifunctional molecules are more effective than M7824, the current lead candidate in clinical development.

In accordance with one embodiment of the present disclosure, therefore, provided is a multifunctional molecule, comprising an anti-PD-L1 (programmed death-ligand 1) antibody or fragment thereof and an extracellular domain of human TGF-β RII (TGF-beta receptor type-2), wherein the anti-PD-L1 antibody or fragment thereof has specificity to the human PD-L1 protein and comprises a heavy chain variable region (VH) comprising a VH CDR1, a VH CDR2 and a VH CDR3, and a light chain variable region (VL) comprising a VL CDR1, a VL CDR2, and a VL CDR3, wherein the VH CDR1, VH CDR2, VH CDR3, VL CDR1, VL CDR2, and VL CDR3, respectively, comprise the amino acid sequences of SEQ ID NO:7-12, 13-18, 19; 20; 21-24, or 19; 91; 21-24, or 19; 92; 21-24, wherein the human TGF-β RII extracellular domain comprises the amino acid sequence of SEQ ID NO:72 and is fused to the anti-PD-L1 antibody or fragment thereof.

In one embodiment, provided is an anti-PD-L1 (programmed death-ligand 1) antibody or fragment thereof, which has specificity to the human PD-L1 protein and comprises a heavy chain variable region (VH) comprising a VH CDR1, a VH CDR2 and a VH CDR3, and a light chain variable region (VL) comprising a VL CDR1, a VL CDR2, and a VL CDR3, wherein the VH CDR1, VH CDR2, VH CDR3, VL CDR1, VL CDR2, and VL CDR3, respectively, comprise the amino acid sequences of SEQ ID NO:7-12, 13-18, 19; 20; 21-24, or 19; 91; 21-24, or 19; 92; 21-24.

Also provided is a multifunctional molecule, comprising an antibody or antigen-binding fragment thereof fused, through a peptide linker, to the N-terminus of the amino acid sequence of SEQ ID NO:72, wherein the peptide linker (a) is at least 30 amino acid residues in length, or (b) is at least 25 amino acid residues in length and comprises an alpha helix motif.

Also provided are uses and methods for treating cancer with any of the molecules of the present disclosure.

DETAILED DESCRIPTION

Definitions

Figure 1:
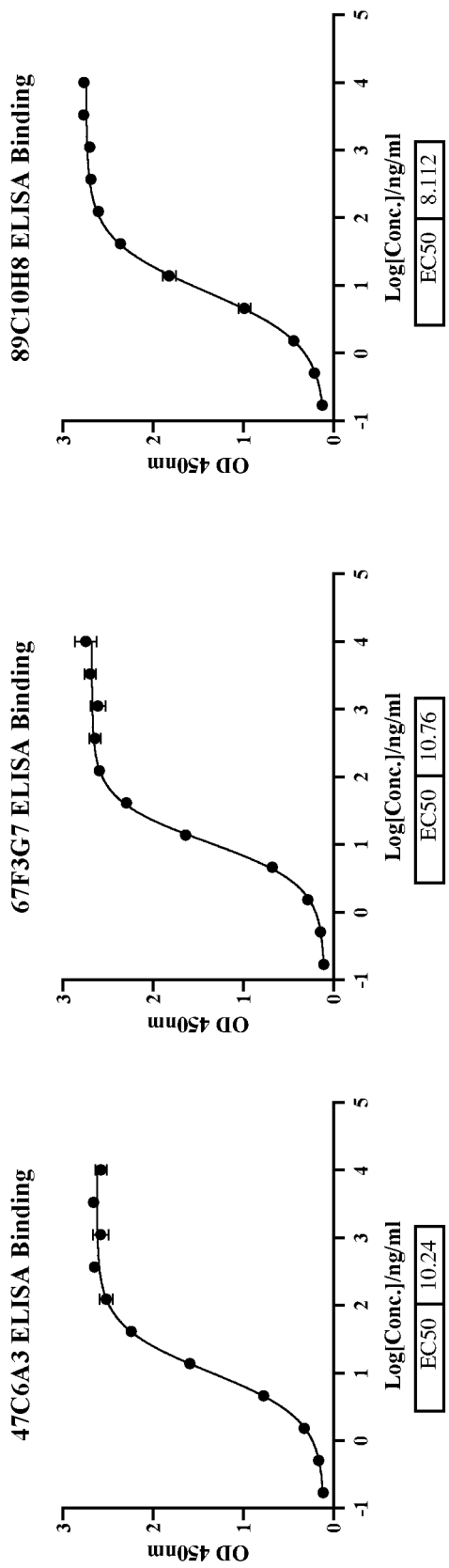
FIG. 1 shows that 47C6A3, 67F3G7 and 89C10H8 can bind to human PD-L1 with high affinity.
Figure 2:
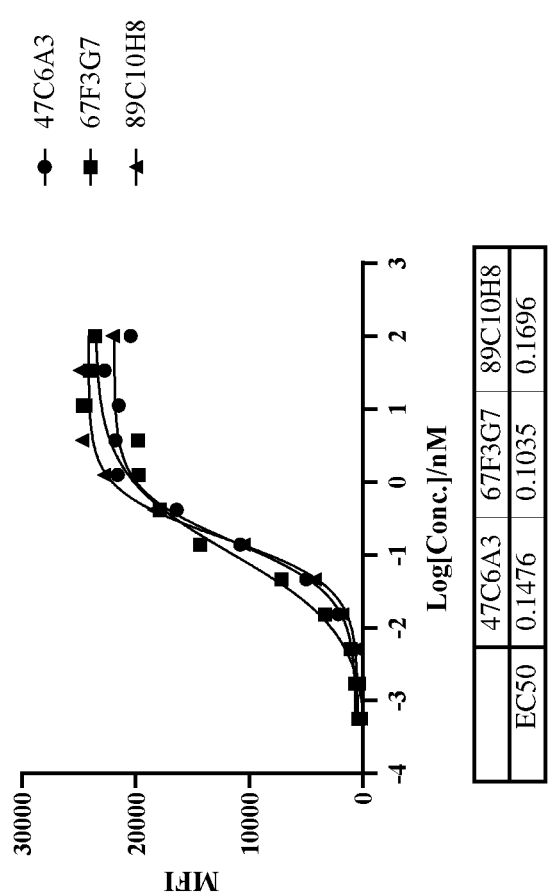
FIG. 2 shows the 47C6A3, 67F3G7 and 89C10H8 antibodies can highly binding to PD-L1 expressed on mammalian cells.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG$_1$, IgG$_2$, IgG$_3$, IgG$_4$, IgG$_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Multifunctional Molecules

As demonstrated in the appended experimental examples, the instant inventors were able to identify a number of bifunctional fusion proteins that include an anti-PD-L1 unit and a TGF-β-targeting unit. As shown in Example 14, for instance, both of the tested bifunctional proteins, LP008-02 and LP008-06a-ES, exhibited greater efficacy than M7824 in a MC38 mouse model. M7824 is a PD-L1/TGF-β dual targeting fusion protein currently in phase II clinical trial for patients with HPV-positive malignancies. M7824's anti-PD-L1 unit is based on avelumab, which is a leading PD-L1 antibody and has been approved for the treatment of Merkel cell carcinoma and urothelial cancer. The superior performance of the newly disclosed bifunctional proteins, as compared to M7824, is therefore surprising.

Further, as shown in Example 12, the instantly disclosed bifunctional proteins have better species specificity. Unlike M7824 which reacts with mouse and rat PD-L1 as well, the new bifunctional proteins bind to only human and cynomolgus PD-L1, in addition to its superior PD-L1 binding activity.

In one embodiment, therefore, the present disclosure provides a multifunctional molecules having at least an anti-PD-L1 unit and a TGF-β-targeting unit. The anti-PD-L1 unite can include an anti-PD-L1 antibody or fragment of the present disclosure. The TGF-β-targeting unit is preferably an extracellular domain of human transforming growth factor-β (TGF-β) receptor II (TGF-β RII or TGFBR2).

TGF-β RII has two isoforms. Isoform A (NP_001020018.1; SEQ ID NO:70) has a longer extracellular fragment than Isoform B (NP_003233.4; SEQ ID NO:71), but they share the same core ectodomain (SEQ ID NO:72). Their sequences are provided in Table A below.

TABLE A

Sequences related to TGF-β RII (underlined and bold: core ectodomain; underlined and italic: different residues between isoforms; underlined only: mutations)

| Name | Sequence | SEQ ID NO: |
|---|---|---|
| TGEBR2 isoform A | MGRGLLRGLWPLHIVLWTRIASTIPPHVQKS*DVEMEAQKDETICPSCNRT AHPLRHI*NNDMIVTDNNGAVKFPQLCKFCDVRFSTCDNQKSCMSNCSITS ICEKPQEVCVAVWRKNDENITLETVCHDPKLPYHDFILEDAASPKCIMKE KKKPGETFFMCSCSSDECNDNIIFSEEYNTSNPDLLLVIFQVTGISLLPP LGVAISVIIIFYCYRVNRQQKLSSTWETGKTRKLMEFSEHCAIILEDDRS DISSTCANNINHNTELLPIELDTLVGKGRFAEVYKAKLKQNTSEQFETVA VKIFPYEEYASWKTEKDIFSDINLKHENILQFLTAEERKTELGKQYWLIT AFHAKGNLQEYLTRHVISWEDLRKLGSSLARGIAHLSDHTPCGRPKMPI VHRDLKSSNILVKNDLTCCLCDFGLSLRLDPTLSVDDLANSGQVGTARYM APEVLESRMNLENVESFKQTDVYSMALVLWEMTSRCNAVGEVKDYEPPFG SKVREHPCVESMKDNVLRDRGRPEIPSFWLNHQGIQMVCETLTECWDHDP EARLTAQCVAERFSELEHLDRLSGRSCSEEKIPEDGSLNTTK | 70 |
| TGEBR2 isoform B | MGRGLLRGLWPLHIVLWTRIASTIPPHV*Q*KSVNNDMIVTDNNGAVKFPQL CKFCDVRFSTCDNQKSCMSNCSITSICEKPQEVCVAVWRKNDENITLETV CHDPKLPYHDFILEDAASPKCIMKEKKKPGETFFMCSCSSDECNDNIIFS EEYNTSNPDLLLVIFQVTGISLLPPLGVAISVIIIFYCYRVNRQQKLSST WETGKTRKLMEFSEHCAIILEDDRSDISSTCANNINHNTELLPIELDTLV GKGRFAEVYKAKLKQNTSEQFETVAVKIFPYEEYASWKTEKDIFSDINLK HENILQFLTAEERKTELGKQYWLITAFHAKGNLQEYLTRHVISWEDLRKL GSSLARGIAHLSDHTPCGRPKMPIVHRDLKSSNILVKNDLTCCLCDFGL SLRLDPTLSVDDLANSGQVGTARYMAPEVLESRMNLENVESFKQTDVYSM ALVLWEMTSRCNAVGEVKDYEPPFGSKVREHPCVESMKDNVLRDRGRPEI PSFWLNHQGIQMVCETLTECWDHDPEARLTAQCVAERFSELEHLDRLSGR SCSEEKIPEDGSLNTTK | 71 |
| Ectodomain | QLCKFCDVRFSTCDNQKSCMSNCSITSICEKPQEVCVAVWRKNDENITLE TVCHDPKLPYHDFILEDAASPKCIMKEKKKPGETFFMCSCSSDECNDNII FS | 72 |
| Variant 1 (Longer extracellular fragment) | IPPHVQKSVNNDMIVTDNNGAVKFPQLCKFCDVRFSTCDNQKSCMSNCSI TSICEKPQEVCVAVWRKNDENITLETVCHDPKLPYHDFILEDAASPKCIM KEKKKPGETFFMCSCSSDECNDNIIFSEEYNTSNPD | 61 |
| Variant 2 (N-terminal 25 amino acid truncation from variant 1) | QLCKFCDVRFSTCDNQKSCMSNCSITSICEKPQEVCVAVWRKNDENITLE TVCHDPKLPYHDFILEDAASPKCIMKEKKKPGETFFMCSCSSDECNDNII FSEEYNTSNPD | 73 |
| Variant 3 (removal of potential glycosylation sites from variant 1) | IPPHVQXXVNNDMIVTDNXGAVKFPQLCKFCDVRFSTCDNQKSCMSNCSI TSICEKPQEVCVAVWRKNDENITLETVCHDPKLPYHDFILEDAASPKCIM KEKKKPGETFFMCSCSSDECNDNIIFSEEYNTSNPD | 74 |
| Variant 4 (Longer peptides substitute) | TAGHTQTSTGGGAITTGTSGAGHGPQLCKFCDVRFSTCDNQKSCMSNCSI TSICEKPQEVCVAVWRKNDENITLETVCHDPKLPYHDFILEDAASPKCIM KEKKKPGETFFMCSCSSDECNDNIIFSEEYNTSNPD | 75 |
| Variant 5 (Longer peptides substitute and C terminal deletion) | TAGHTQTSTGGGAITTGTSGAGHGPQLCKFCDVRFSTCDNQKSCMSNCSI TSICEKPQEVCVAVWRKNDENITLETVCHDPKLPYHDFILEDAASPKCIM KEKKKPGETFFMCSCSSDECNDNIIFS | 76 |

TABLE A-continued

Sequences related to TGF-β RII (underlined and bold: core ectodomain; underlined and italic: different residues between isoforms; underlined only: mutations)

| Name | Sequence | SEQ ID NO: |
|---|---|---|
| Variant 6 (Shorter peptides substitute and C terminal deletion) | HYPQLCKFCDVRFSTCDNQKSCMSNCSITSICEKPQEVCVAVWRKNDENI TLETVCHDPKLPYHDFILEDAASPKCIMKEKKKPGETFFMCSCSSDECND NIIFS | 77 |
| Variant 7 (shorter peptides substitute) | HYPQLCKFCDVRFSTCDNQKSCMSNCSITSICEKPQEVCVAVWRKNDENI TLETVCHDPKLPYHDFILEDAASPKCIMKEKKKPGETFFMCSCSSDECND NIIFSEEYNTSNPD | 78 |
| Substitute N-terminal fragment of Variant 3 | IPPHVQXXVNNDMIVTDNXGAVKF | 88 |

In some embodiments, the TGF-β RII extracellular domain includes the core ectodomain (SEQ ID NO:72) as well as some flanking residues. For instance, Variant 1 (SEQ ID NO:61) which was tested in Examples 8-15 includes additional 25 residues at the N-terminal side and nine on the C-terminal side. Another variant, Variant 2 (SEQ ID NO:73) only includes the nine C-terminal flanking residues. Other variants such as Variants 4-7 (SEQ ID NO:75-78) include alternative linkers replacing part of the N-terminal sequences of SEQ ID NO:61.

In some embodiments, the TGF-β RII extracellular domain does not include the first 1, 2, 3, 4, 5, 6, 7, 8, 9, 10, 11, 12, 13, 14, 15, 16, 17, 18, 19, 20, 21, 22, 23, 24 or 25 amino acids of SEQ ID NO:61. In some embodiments, the TGF-β RII extracellular domain does not include the last 1, 2, 3, 4, 5, 6, 7, 8, or 9 amino acids of SEQ ID NO:61.

Yet another variant, Variant 3, is based on Variant 1 but includes at least an amino acid substitution at the X positions within the N-terminal portion (SEQ ID NO:88). These X positions are potential glycosylation sites. The substitution, therefore, is with an amino acid other than K, S, and N. Examples of substitutions are R, A, G, Q, I, L, D, or E, without limitation.

The ani-PD-L1 unit, in some embodiments, is comprised of an anti-PD-L1 antibody of fragment thereof as further described below. The antibody or fragment may take any antibody format, such as the conventional full IgG format, a Fab fragment, a single chain fragment, or a single domain antibody, without limitation. When the antibody or fragment thereof has a light chain and a separate heavy chain, the TGF-β RII extracellular domain can be fused to either the light chain or the heavy chain. When the antibody or fragment thereof has a light chain and a heavy chain on a single protein chain (e.g., scFv), the TGF-β RII extracellular domain can be fused to be closer to either the light chain or the heavy chain.

In some embodiments, the TGF-β RII extracellular domain is fused to the N-terminus of a chain of the anti-PD-L1 unit. In some embodiments, the TGF-β RII extracellular domain is fused to the C-terminus of a chain of the anti-PD-L1 unit. In a preferred embodiment, the TGF-β RII extracellular domain is fused to the C-terminus of the heavy chain of the anti-PD-L1 unit, optionally though a peptide linker (e.g., SEQ ID NO:60, or one, two, or three GGGGS (SEQ ID NO:86) repeats).

In some embodiments, the anti-PD-L1 unit includes a VH (heavy chain variable region) and a VL (light chain variable region). The VH and VL regions include VH CDR1, VH CDR2, VH CDR3, VL CDR1, VL CDR2, and VL CDR3, such as those illustrated in Tables 1A-1C.

In one embodiment, the VH CDR1, VH CDR2, VH CDR3, VL CDR1, VL CDR2, and VL CDR3 comprise the sequences of SDYAWN (SEQ ID NO:7), YIIYSGSTSYN-PSLKS (SEQ ID NO:8), STMIATNWFAY (SEQ ID NO:9), KASQDVSLAVA (SEQ ID NO:10), WASTRHT (SEQ ID NO:11), and QQHYITPWT (SEQ ID NO:12), respectively. Examples of such VH sequences are provided in SEQ ID NO:25 (mouse) and 26-28 (humanized). Examples of such VL sequences are provided in SEQ ID NO:29 (mouse) and 30 (humanized). Example humanized antibodies include those that have a VH of SEQ ID NO:26, or 27, or 28 and a VL of SEQ ID NO:30.

In one embodiment, the VH CDR1, VH CDR2, VH CDR3, VL CDR1, VL CDR2, and VL CDR3 comprise the sequences of DFWVS (SEQ ID NO:13), EIYPNSGVS-RYNEKFKG (SEQ ID NO:14), YFGYTYWFGY (SEQ ID NO:15), RASKSVSTYMH (SEQ ID NO:16), SASHLES (SEQ ID NO:17) and QQSNELPVT (SEQ ID NO:18), respectively. Examples of such VH sequences are provided in SEQ ID NO:31 (mouse) and 32-37 (humanized). Examples of such VL sequences are provided in SEQ ID NO:38 (mouse) and 39-43 (humanized). Example humanized antibodies include those that have a VH of SEQ ID NO:34 and a VL of SEQ ID NO:39, 40, or 43, have a VH of SEQ ID NO:35 and a VL of SEQ ID NO:39, or have a VH of SEQ ID NO:37 and VL of SEQ ID NO:39. In one embodiment, the humanized antibody includes a VH of SEQ ID NO:34 and a VL of SEQ ID NO:43.

In one embodiment, the VH CDR1, VH CDR2, VH CDR3, VL CDR1, VL CDR2, and VL CDR3 comprise the sequences of NYWMT (SEQ ID NO:19), SITNTGS-STFYPDSVKG (SEQ ID NO:20), DTTIAPFDY (SEQ ID NO:21), KASQNLNEYLN (SEQ ID NO:22), KTNTLQA (SEQ ID NO:23) and SQYNSGNT (SEQ ID NO:24), respectively. Alternatively, VH CDR2 can includes SITN-TGSSTFYPDAVKG (SEQ ID NO:91) or SITNTGS-STFYPESVKG (SEQ ID NO:92). Examples of such VH sequences are provided in SEQ ID NO:44 (mouse) and 45-49 (humanized) and 57-58 (humanized). Examples of such VL sequences are provided in SEQ ID NO:50 (mouse) and 51-55 (humanized) and 56 (humanized).

Example humanized antibodies include those that have a VH of SEQ ID NO:49 and a VL of SEQ ID NO:52 or 54, or have a VH of SEQ ID NO:48 and a VL of SEQ ID NO:53 or 54. In one embodiment, the humanized antibody includes a VH of SEQ ID NO:48 and a VL of SEQ ID NO:53. In one embodiment, the humanized antibody includes a VH of SEQ ID NO:48 and a VL of SEQ ID NO:56. In one embodiment, the humanized antibody includes a VH of SEQ ID NO:57 and a VL of SEQ ID NO:56. In one embodiment, the humanized antibody includes a VH of SEQ ID NO:58 and a VL of SEQ ID NO:56.

In some embodiments, the antibody or fragment thereof further a heavy chain constant region (e.g., CH1, CH2 and/or CH3) and/or a light chain constant region (e.g., CL). An example heavy chain constant region is provided in SEQ ID NO:59, and an example light chain constant region is provided in SEQ ID NO:67 (residues 108-214).

TGF-β RII x Antibody Fusions

Testing with different fusion protein designs (e.g., Table 15) demonstrated that only the core ectodomain (SEQ ID NO:72) of TGF-β RII is required for activity. Further, the extracellular domain of TGF-β RII should not be directly fused to the antibody. There should be a sufficient distance, provided by a peptide linker.

With reference to the ectodomain, the peptide linker (which may be entirely an artificial linker, or include part of extracellular fragment N-terminal to the ectodomain, SEQ ID NO:89) should have a minimum length. If the distance is too short, the fusion protein has reduced stability or activity. The minimum length, in some embodiment, is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residents. In some embodiments, the linker is not longer than 35, 40, 45, 50, 55, 60, 65, 70, 75, 80, 85, 90, 95, 100, 110, 120, 130, 140, 150, 170 or 200 amino acid residues.

Inclusion of a flexible linker, e.g., one or more G4S (SEQ ID NO:86) units and, in some embodiment, can be useful for the stability and/or activity of the multifunctional molecule. In some embodiments, the flexible linker includes at least 40%, 50%, 60%, 70% or 80% glycine. In some embodiments, the flexible linker includes one or more serine. In some embodiments, the flexible linker includes 1, 2, 3, 4, 5 or 6 G4S (SEQ ID NO:86) repeats.

It is shown that, in some embodiments, the natural N-terminal fragment (IPPHVQKSVNNDMIVTDNNGAVKFP; SEQ ID NO:89) can be relaced with a substitute peptide to increase stability, without sacrifice or even with improvement of activity. In some embodiments, the substitute peptide is different from SEQ ID NO:89 but has at least 30%, 40%, 50%, 60%, 70%, 80% or 90% sequence identity to SEQ ID NO:89.

An example substitute peptide is IPPHVQXXVNNDMIVTDNXGAVKFP (SEQ ID NO:88), wherein X is any amino acid except K, S, or N. In some embodiments, substitutions can be made to remove the rigid di-peptide PP, removal of potential cleavage sites QK, N and/or K, include multiple glycine residues to increase flexibility, and/or reduce hydrophobic residues. One such example is TAGHTQTSTGGGAITTGTSGAGHGP (SEQ ID NO:87) or a variant having at least 50%, 55%, 60%, 65%, 70%, 75%, 80%, 85%, 90%, or 95% sequence identity to SEQ ID NO:87. In some embodiments, the variant includes at least 4 G, no PP dipeptide, no more than 3 hydrophobic amino acid residues selected from the group consisting of I, L, M, F, V, W, Y and P. In some embodiments, the variant includes at least 5 G and no more than 1 hydrophobic amino acid residue selected from the group consisting of I, L, M, F, V, W, Y and P.

In some embodiments, the peptide linker between the antibody or fragment thereof and the ectodomain (SEQ ID NO:72) of TGF-β RII include a flexible linker. In some embodiments, the peptide linker includes a substitute peptide of SEQ ID NO:89. In some embodiments, the peptide linker includes both a flexible linker and a substitute peptide. In some embodiments, the flexible linker is N-terminal to the substitute peptide. In some embodiments, the flexible linker is C-terminal to the substitute peptide.

In some embodiments, the multifunctional molecule at least does not include the entire sequence of EEYNTSNPD (SEQ ID NO:90). The multifunctional molecule may have the entire SEQ ID NO:90 removed from the extracellular domain of TGF-β RII. In some embodiments, the multifunctional molecule does not include more than 1, 2, 3, 4, 5, 6, 7 or 8 amino acid residues of EEYNTSNPD (SEQ ID NO:90).

The antibody or antigen-binding fragment thereof of the multifunctional molecule may target any antigen. Non-limiting examples are PD-1, PD-L1, CTLA-4, LAG-3, CD28, CD122, 4-1BB, TIM3, OX-40, OX40L, CD40, CD40L, LIGHT, ICOS, ICOSL, GITR, GITRL, TIGIT, CD27, VISTA, B7H3, B7H4, BTLA, CD47 and CD73. They can also be any antibodies or fragments as disclosed herein.

The ectodomain of TGF-β RII may be fused to any part of the antibody or fragment. In some embodiments, the ectodomain is fused to the C-terminus of a heavy chain or a light chain of the antibody or fragment. In some embodiments, ectodomain is fused to the C-terminus of a Fc fragment of the antibody or fragment.

Anti-PD-L1 Antibodies and Fragments

Anti-PD-L1 antibodies and fragments are also provided, which can be used as an anti-PD-L1 unit in a multifunctional molecule, a bi- or multi-specific antibody, or alone in a monospecific antibody.

In some embodiments, the anti-PD-L1 antibody or fragment includes a VH (heavy chain variable region) and a VL (light chain variable region). The VH and VL regions include VH CDR1, VH CDR2, VH CDR3, VL CDR1, VL CDR2, and VL CDR3, such as those illustrated in Tables 1A-1C.

In one embodiment, the VH CDR1, VH CDR2, VH CDR3, VL CDR1, VL CDR2, and VL CDR3 comprise the sequences of SDYAWN (SEQ ID NO:7), YIIYSGSTSYNPSLKS (SEQ ID NO:8), STMIATNWFAY (SEQ ID NO:9), KASQDVSLAVA (SEQ ID NO:10), WASTRHT (SEQ ID NO:11), and QQHYITPWT (SEQ ID NO:12), respectively. Examples of such VH sequences are provided in SEQ ID NO:25 (mouse) and 26-28 (humanized). Examples of such VL sequences are provided in SEQ ID NO:29 (mouse) and 30 (humanized). Example humanized antibodies include those that have a VH of SEQ ID NO:26, or 27, or 28 and a VL of SEQ ID NO:30.

In one embodiment, the VH CDR1, VH CDR2, VH CDR3, VL CDR1, VL CDR2, and VL CDR3 comprise the sequences of DFWVS (SEQ ID NO:13), EIYPNSGVSRYNEKFKG (SEQ ID NO:14), YFGYTYWFGY (SEQ ID NO:15), RASKSVSTYMH (SEQ ID NO:16), SASHLES (SEQ ID NO:17) and QQSNELPVT (SEQ ID NO:18), respectively. Examples of such VH sequences are provided in SEQ ID NO:31 (mouse) and 32-37 (humanized). Examples of such VL sequences are provided in SEQ ID NO:38 (mouse) and 39-43 (humanized). Example humanized antibodies include those that have a VH of SEQ ID NO:34 and a VL of SEQ ID NO:39, 40, or 43, have a VH of SEQ ID NO:35 and a VL of SEQ ID NO:39, or have a VH of SEQ ID NO:37 and VL of SEQ ID NO:39. In one embodiment, the humanized antibody includes a VH of SEQ ID NO:34 and a VL of SEQ ID NO:43.

In one embodiment, the VH CDR1, VH CDR2, VH CDR3, VL CDR1, VL CDR2, and VL CDR3 comprise the sequences of NYWMT (SEQ ID NO:19), SITNTGSSTFYPDSVKG (SEQ ID NO:20), DTTIAPFDY (SEQ ID NO:21), KASQNLNEYLN (SEQ ID NO:22), KTNTLQA (SEQ ID NO:23) and SQYNSGNT (SEQ ID NO:24), respectively. Alternatively, VH CDR2 can includes SITNTGSSTFYPDAVKG (SEQ ID NO:91) or SITNTGSSTFYPESVKG (SEQ ID NO:92). Examples of such VH sequences are provided in SEQ ID NO:44 (mouse) and 45-49 (humanized) and 57-58 (humanized). Examples of such VL sequences are provided in SEQ ID NO:50 (mouse) and 51-55 (humanized) and 56 (humanized).

Example humanized antibodies include those that have a VH of SEQ ID NO:49 and a VL of SEQ ID NO:52 or 54, or have a VH of SEQ ID NO:48 and a VL of SEQ ID NO:53 or 54. In one embodiment, the humanized antibody includes a VH of SEQ ID NO:48 and a VL of SEQ ID NO:53. In one embodiment, the humanized antibody includes a VH of SEQ ID NO:48 and a VL of SEQ ID NO:56. In one embodiment, the humanized antibody includes a VH of SEQ ID NO:57 and a VL of SEQ ID NO:56. In one embodiment, the humanized antibody includes a VH of SEQ ID NO:58 and a VL of SEQ ID NO:56.

In some embodiments, the antibody or fragment thereof further a heavy chain constant region (e.g., CH1, CH2 and/or CH3) and/or a light chain constant region (e.g., CL). An example heavy chain constant region is provided in SEQ ID NO:59, and an example light chain constant region is provided in SEQ ID NO:67 (residues 108-214).

It is contemplated that small changes (e.g., one amino acid addition, deletion or substitution) can be designed among these CDR sequences that can retain the antibodies' activities or even improve them. Such modified CDR sequences are referred to as CDR variants. It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence. In some embodiments, the modified antibody or fragment retains the designate CDR sequences.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Polynucleotides Encoding the Proteins and Methods of Preparing the Proteins

The present disclosure also provides isolated polynucleotides or nucleic acid molecules encoding the multifunctional proteins, antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Cancer Treatment

As described herein, the antibodies, variants or derivatives of the present disclosure may be used in certain treatment and diagnostic methods.

The present disclosure is further directed to multifunctional molecule- or antibody-based therapies which involve administering the multifunctional molecules or the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. PD-L1 can be overexpressed in tumor cells. Tumor-derived PD-L1 can bind to PD-1 on immune cells thereby limiting antitumor T-cell immunity. Results with small molecule inhibitors, or monoclonal antibodies targeting PD-L1 in murine tumor models, indicate that targeted PD-L1 therapy is an important alternative and realistic approach to effective control of tumor growth. As demonstrated in the experimental examples, the anti-PD-L1 antibodies activated the adaptive immune response machinery, which can lead to improved survival in cancer patients.

Accordingly, in some embodiments, provided are methods for treating a cancer in a patient in need thereof. The method, in one embodiment, entails administering to the patient an effective amount of a multifunctional molecule or an antibody of the present disclosure. In some embodiments, at least one of the cancer cells (e.g., stromal cells) in the patient expresses, over-express, or is induced to express PD-L1. Induction of PD-L1 expression, for instance, can be done by administration of a tumor vaccine or radiotherapy.

Tumors that express the PD-L1 protein include those of bladder cancer, non-small cell lung cancer, renal cancer, breast cancer, urethral cancer, colorectal cancer, head and neck cancer, squamous cell cancer, Merkel cell carcinoma, gastrointestinal cancer, stomach cancer, oesophageal cancer, ovarian cancer, renal cancer, and small cell lung cancer. Accordingly, the presently disclosed antibodies can be used for treating any one or more such cancers.

Cellular therapies, such as chimeric antigen receptor (CAR) T-cell therapies, are also provided in the present disclosure. A suitable cell can be used, that is put in contact with an anti-PD-L1 antibody of the present disclosure (or alternatively engineered to express an anti-PD-L1 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

EXAMPLES

Example 1: Generation of Mouse Monoclonal Antibodies Against Human PD-L1

This example describes anti-human-PD-L1 mouse monoclonal antibodies generated using the hybridoma technology.

Antigen: human PDL1-Fc protein and human PD-L1 highly expressed on the CHOK1 cell line (PDL1-CHOK1 cell line).

Immunization: To generate mouse monoclonal antibodies to human PD-L1, Balb/c mice and Wistar Rat were firstly immunized with PD-L1-Fc protein. The immunized mice and Rat were subsequently boosted with the fusion PD-L1-Fc protein, CHO-K1/PD-L1 stable cells and PD-L1-Fc protein. To select mice or rat producing antibodies that bound PD-L1 protein, the serum of immunized mice was subjected to the antibody titer evaluation by ELISA. Briefly, microtiter plates were coated with human PD-L1 protein at 0.5 µg/ml in ELISA coating buffer, 100 µl/well at 4° C. overnight, then blocked with 150 µl/well of 1% BSA. Dilutions of serum from immunized mice were added to each well and incubated for 1-2 hours at 37° C. The plates were washed with PBS/Tween and then incubate with anti-mouse IgG antibody conjugated with Horse Radish Peroxidase (HRP) or anti-rat IgG antibody conjugated with HRP for 1 hour at 37° C. After washing, the plates were developed with TMB substrate and analyzed by spectrophotometer at OD 450 nm. Post 3 rounds of immunization, Immune response will also be tested by serum ELISA against rhPD-L1 protein and FACS against CHO-K1/PDL-1 stable cell line while CHO-K1 parental cell line served as negative control. Mice with sufficient titers of anti-PDL1 IgG were boosted with 25 μg human PDL1-Fc protein after 4 rounds of immunization. The resulting mice were used for fusions. The hybridoma supernatants were tested for anti-PD-L1 IgGs by ELISA.

Cell fusion: Fusion was performed by electro fusion. Fused cells were plated into 50 96-well plates for each fusion.

Screening: The supernatants were screened by ELISA against recombinant human (rh) PD-L1 Fc protein and counter screening antigen. Then, positive supernatants underwent confirmative screening from primary screening with receptor blocking FACS against CHO-K1/PD-L1 stable cell line and rhPD1-Fc protein.

Subcloning and screening: positive primary clones from each fusion were subcloned by limiting dilution to ensure that the subclones were derived from a single parental cell. Subcloning were screened the same as primary clones and culture supernatant of positive clones underwent additional confirmative screening by affinity ranking.

Hybridoma clones 47C6A3, 67F3G7 and 89C10H8 were selected for further analysis. The amino acid sequences of the variable regions of 47C6A3, 67F3G7 and 89C10H8 are provided in Table 1 below.

TABLE 1

Sequences of the variable regions of 47C6A3, 67F3G7 and 89C10H8

| Name | Sequence | SEQ ID NO: |
|---|---|---|
| 47C6A3 VH | DVQLQESGPGLVKPSQSLSLTCTVTGYSITSDYAWNWIRQFPGNKLEWMGYIIYSGSTS YNPSLKSRISITRDTSKNQFFLQLNSVTTEDTATYYCARSTMIATNWFAYWGQGTLVTV SA | 1 |
| 47C6A3 VL | DIVMTQSHKFMSTSVVDRVSITCKASQDVSLAVAWYQQKPGQSPKLLIYWASTRHTGVP DRFTGSGSGTDFALTISSVQAEDLALYYCQQHYITPWTFGGGTKLEIK | 2 |
| 67F3G7 VH | QVKLLQSGAALVKPGASVKMSCKASGYIFTDFWVSWVKQSHEKSLEWIGEIYPNSGVSR YNEKFKGRATMTVDKSTSTAYLELSRLTSEDSAIYYCTKYFGYTYWFGYWGQGTLVTVS S | 3 |
| 67F3G7 VL | DTVLTQSPALAVSLGQRITISCRASKSVSTYMHWYQQRSGLQPKLLIYSASHLESGVPS RFSGSGSGTDFTLTIDPVEADDIANYYCQQSNELPVTFGSGTKLEIK | 4 |
| 89C10H8 VH | EVQLVESGGGLVQPGRSLTLSCVASGFTFSNYWMTWIRQAPGKGLEWVASITNTGSSTF YPDSVKGRFTISRDNTRSTLFLQINSLRSEDTATYYCTRDTTIAPFDYWGQGVMVTVSS | 5 |
| 89C10H8 VL | DIQMTQSPSFLSASVGDRVTITCKASQNLNEYLNWYQQKLGEAPKRLIYKTNTLQAGIP SRFSGSGSGIDYTLTISSLQPEDVATYFCSQYNSGNTFGAGTKLELK | 6 |

Table 1A. CDR sequences of 47C6A3

| 47C6A3 | Sequence | SEQ ID NO: |
|---|---|---|
| CDRH1 | SDYAWN | 7 |
| CDRH2 | YIIYSGSTSYNPSLKS | 8 |
| CDRH3 | STMIATNWFAY | 9 |
| CDRL1 | KASQDVSLAVA | 10 |
| CDRL2 | WASTRHT | 11 |
| CDRL3 | QQHYITPWT | 12 |

Table IB. CDR sequences of 67F3G7

| 67F3G7 | Sequence | SEQ ID NO: |
|---|---|---|
| CDRH1 | DFWVS | 13 |
| CDRH2 | EIYPNSGVSRYNEKFKG | 14 |
| CDRH3 | YFGYTYWFGY | 15 |
| CDRL1 | RASKSVSTYMH | 16 |
| CDRL2 | SASHLES | 17 |
| CDRL3 | QQSNELPVT | 18 |

TABLE 1-continued

Sequences of the variable regions of 47C6A3, 67F3G7 and 89C10H8

Table IC. CDR sequences of 89C10H8

| 89C10H8 | Sequence | SEQ ID NO: |
|---|---|---|
| CDRH1 | NYWMT | 19 |
| CDRH2 | SITNTGSSTFYPDSVKG | 20 |
| ver DA | SITNTGSSTFYPDAVKG | 91 |
| ver ES | SITNTGSSTFYPESVKG | 92 |
| CDRH3 | DTTIAPFDY | 21 |
| CDRL1 | KASQNLNEYLN | 22 |
| CDRL2 | KTNTLQA | 23 |
| CDRL3 | SQYNSGNT | 24 |

Example 2: The Binding Activity to PD-L1 Antigen

ELISA Testing

To evaluate the binding activity of hybridoma clones 47C6A3, 67F3G7 and 89C10H8, the chimeric mAb from these clones were subjected to ELISA test.

Briefly, microtiter plates were coated with human PD-L1-Fc protein at 0.5 µg/ml in PBS, 100 µl/well at 4° C. overnight, then blocked with 150 µl/well of 1% BSA. Three-fold dilutions of 47C6A3, 67F3G7 and 89C10H8 antibodies starting from 10 µg/ml were added to each well and incubated for 1 hour at 37° C. The plates were washed with PBS/Tween and then incubated with Mouse-anti-human IgG Fab antibody conjugated with Horse Radish Peroxidase (HRP) for 30 mins at 37° C. After washing, the plates were developed with TMB substrate and analyzed by spectrophotometer at OD 450 nm. As shown in FIG. 1, 47C6A3, 67F3G7 and 89C10H8 bound to human PD-L1 with high affinity ($EC_{50}$=10.24 ng/ml for 47C6A3, $EC_{50}$=10.76 ng/ml for 67F3G7, $EC_{50}$=8.112 ng/ml for 89C10H8).

Cell-based binding: FACS was used to evaluate the binding activity of 47C6A3, 67F3G7 and 89C10H8 chimeric mAbs on human PD-L1 over-expressed CHOK1 cells.

Briefly, PDL1-CHOK1 cells were firstly incubated with 3-fold serially diluted 47C6A3, 67F3G7 and 89C10H8 chimeric mAbs starting at 100 nM at 4° C. for 40 mins. After washing by PBS, Alexa Fluor® 647 AffiniPure Goat Anti-Human IgG (H+L) were added to each well and incubated at 4° C. for 30 mins. Samples were twice washed with FACS buffer. The mean florescence intensity (MFI) of Alexa Fluor® 647 were evaluated by FACSCanto. As shown in FIG. 2, 47C6A3, 67F3G7 and 89C10H8 bound to PDL1-CHOK1 cells with high affinity ($EC_{50}$=0.1476 nM for 47C6A3, $EC_{50}$=0.1035 nM for 67F3G7, $EC_{50}$=0.1696 nM for 89C10H8).

Cross Species Activity

ELISA testing was carried out to evaluate the binding of chimeric antibodies to human PD-L1, mouse PD-L1, rat PD-L1, and cynomolgus PD-L1, respectively.

Figure 3:
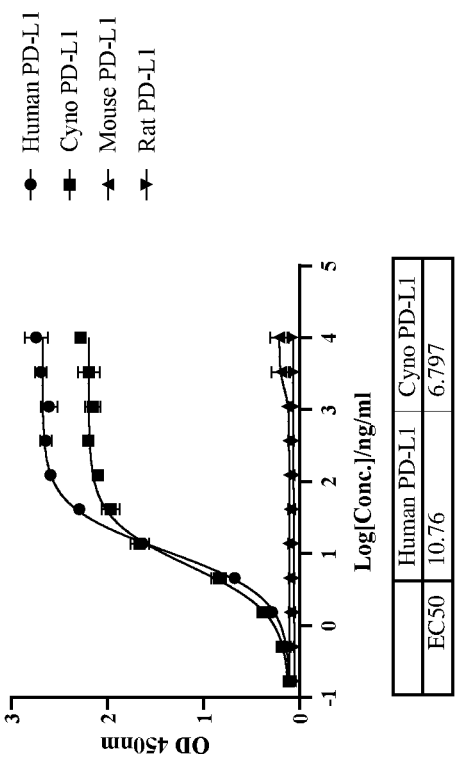
FIG. 3 shows that 47C6A3, 67F3G7 and 89C10H8 antibodies can bind to cynomolgus PD-L1 with high affinity and cannot bind to rat or mouse PD-L1.
Figure 3:
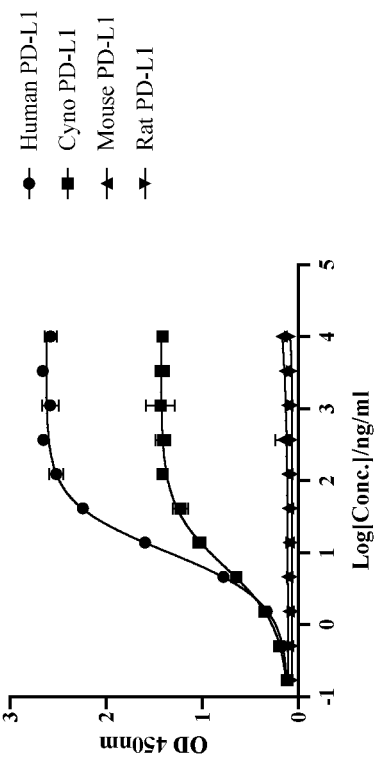
Figure 3:
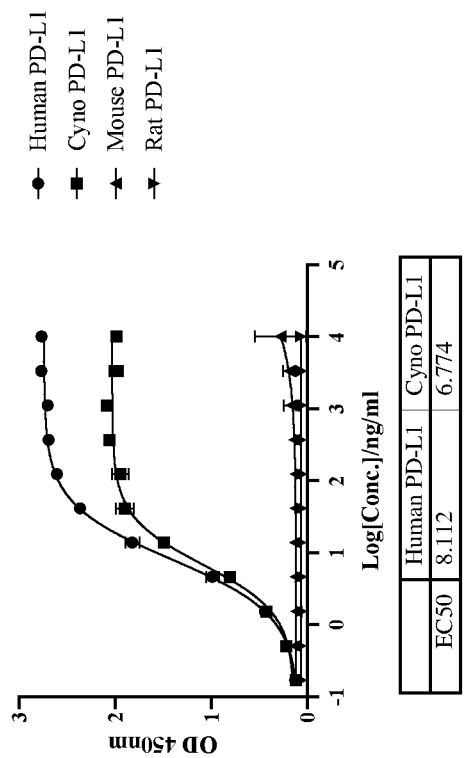
Figure 4:
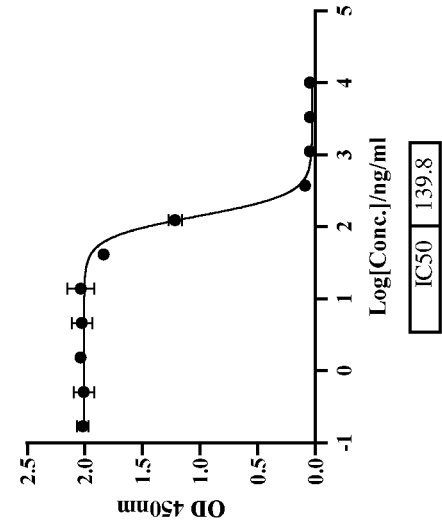
FIG. 4 shows that 47C6A3, 67F3G7 and 89C10H8 can efficiently inhibit the binding of human PD-L1 to human PD1.
Figure 4:
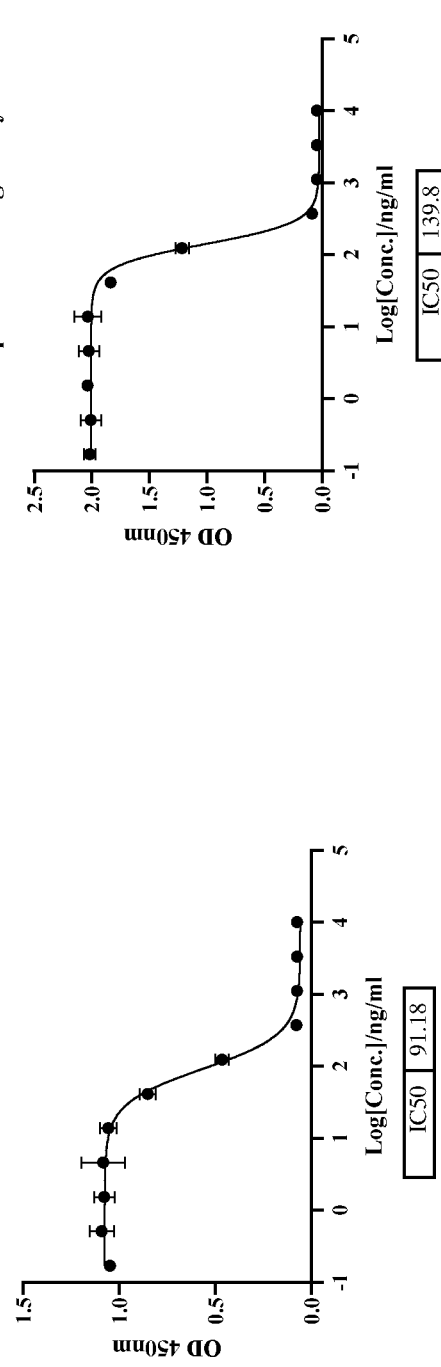
Figure 4:
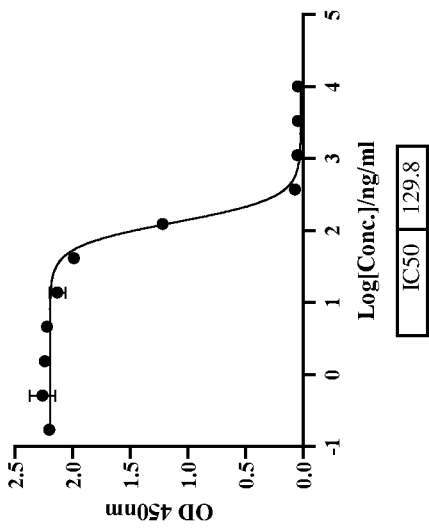

Briefly, microtiter plates were coated with human, mouse, rat and cynomolgus PD-L1 proteins at 0.5 µg/ml in PBS, 100 µl/well at 4° C. overnight, then blocked with 150 µl/well of 1% BSA. Three-fold dilutions of chimeric antibodies starting from 10 µg/ml were added to each well and incubated for 1 hour at 37° C. The plates were washed with PBS/Tween and then incubate with mouse-anti-human IgG Fab antibody conjugated with Horse Radish Peroxidase (HRP) for 30 mins at 37° C. After washing, the plates were developed with TMB substrate and analyzed by spectrophotometer at OD 450 nm. 47C6A3, 67F3G7 and 89C10H8 antibodies bound to cynomolgus PD-L1 and did not bind to rat and mouse PD-L1 (FIG. 3 and Table 2).

TABLE 2

Cross species activity of 47C6A3, 67F3G7 and 89C10H8

| | Human | Cynomolgus | Rat | Mouse |
|---|---|---|---|---|
| EC50 of 47C6A3 | 10.24 ng/ml | 6.336 ng/ml | No binding | No binding |
| EC50 of 67F3G7 | 10.76 ng/ml | 6.797 ng/ml | No binding | No binding |
| EC50 of 89C10H8 | 8.112 ng/ml | 6.774 ng/ml | No binding | No binding |

Example 3. Blockade of PD-L1 Binding to PD-1 by Antibodies

To evaluate the blocking effects of 47C6A3, 67F3G7 and 89C10H8 chimeric mAbs on recombinant human PD-L1 to bind to its receptor PD-1, the ELISA based receptor blocking assay was employed.

Briefly, microtiter plates were coated with human PD-L1-Fc protein at 0.5 µg/ml in PBS, 100 µl/well at 4° C. overnight, then blocked with 150 µl/well of 1% BSA. 50 µl biotin-labeled human PD-1-Fc protein and 3-fold dilutions of 47C6A3, 67F3G7 and 89C10H8 antibodies starting from 10 µg/ml at 50 µl were added to each well and incubated for 1 hour at 37° C. The plates were washed with PBS/Tween and then incubated with Streptavidin-HRP for 10 mins at 37° C. After washing, the plates were developed with TMB substrate and analyzed by spectrophotometer at OD 450 nm. As shown in FIG. 4, 47C6A3, 67F3G7 and 89C10H8 efficiently inhibited the binding of human PD-L1 to human PD1 at $IC_{50}$=91.18 ng/ml, 139.8 ng/ml, 129.8 ng/ml, respectively.

Example 4: Binding Affinity of mAbs

Figure 5:
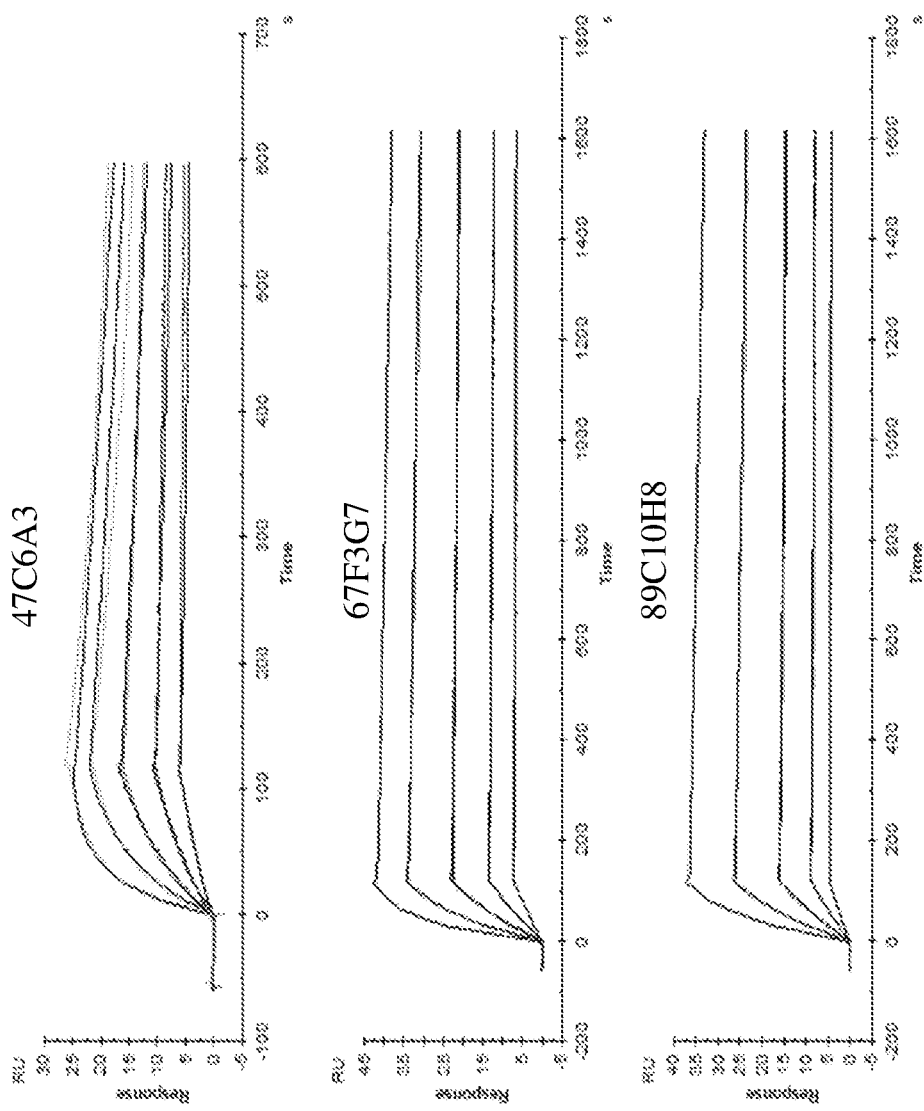
FIG. 5 shows the binding kinetics of 47C6A3, 67F3G7 and 89C10H8 to recombinant PD-L1.
Figure 6A:
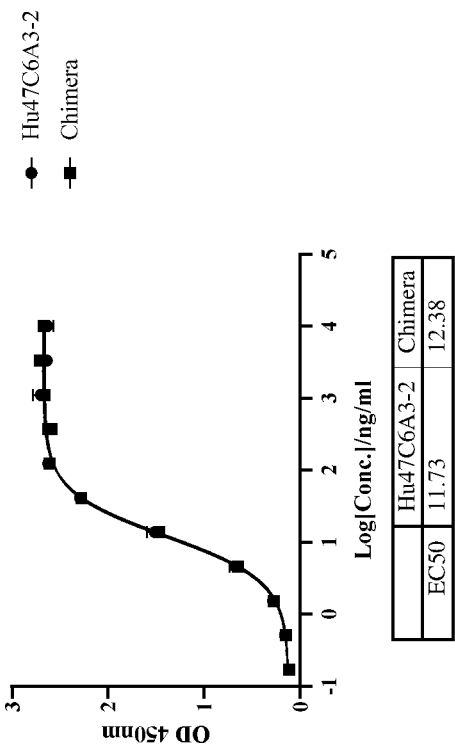
FIG. 6A-C show that all tested humanized antibodies had comparable binding efficacy to human PD-L1 in contact to chimeric antibody.
Figure 6A:
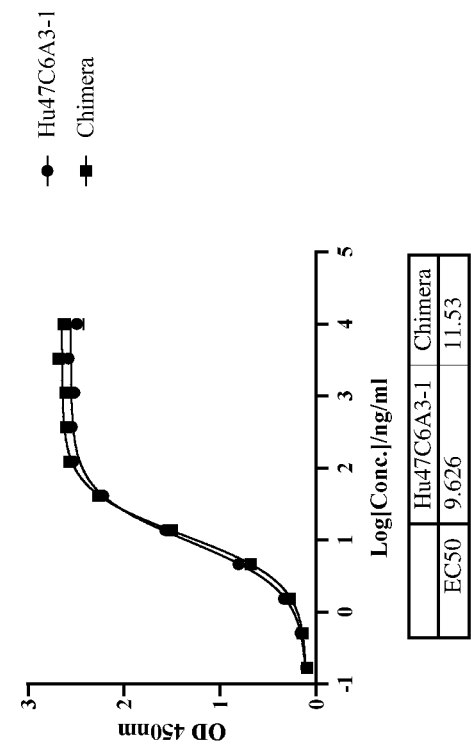
Figure 6A:
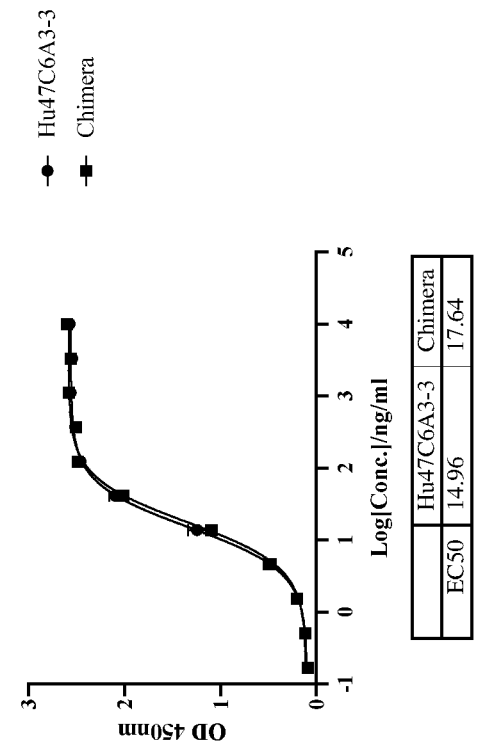
Figure 6B:
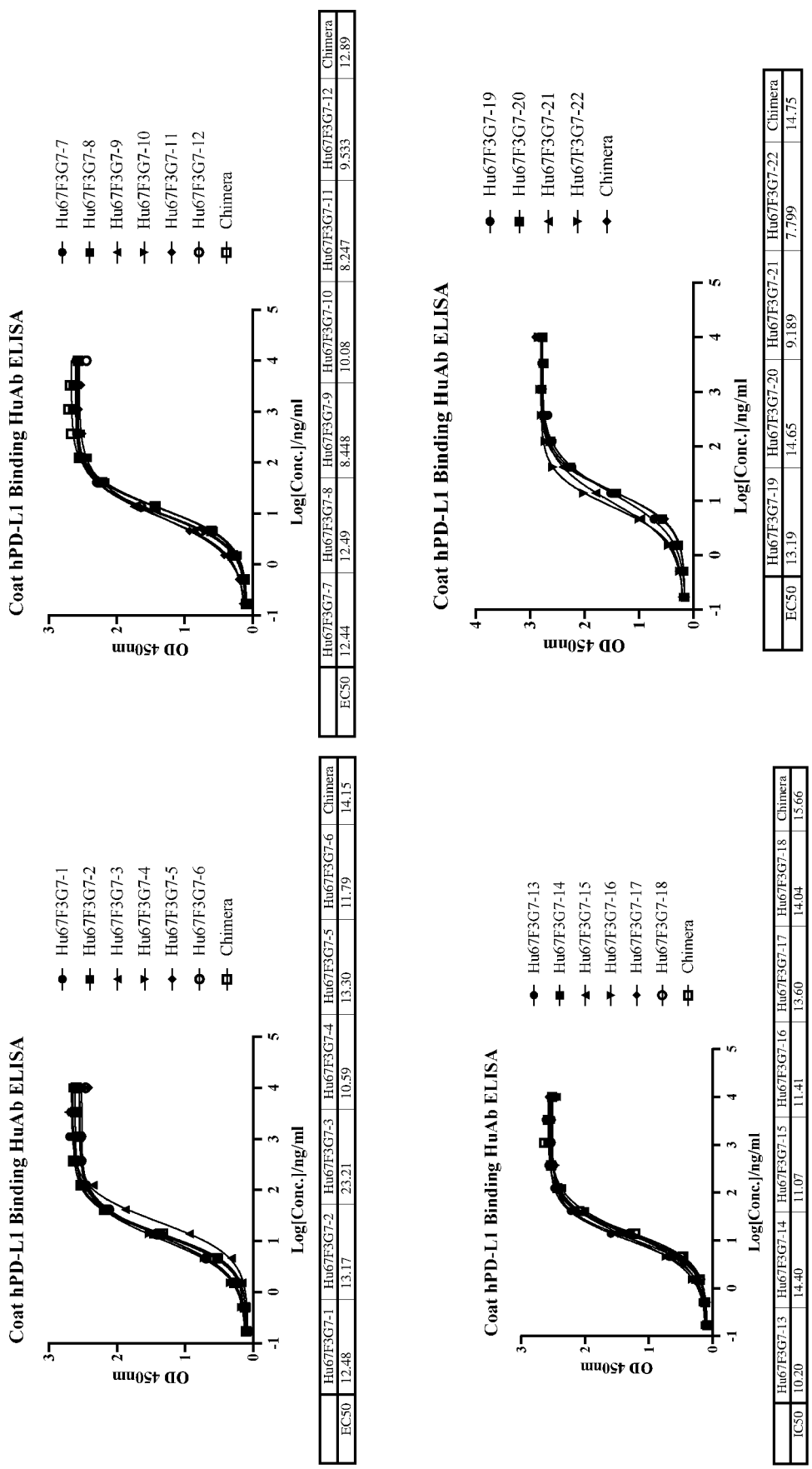
Figure 6C:
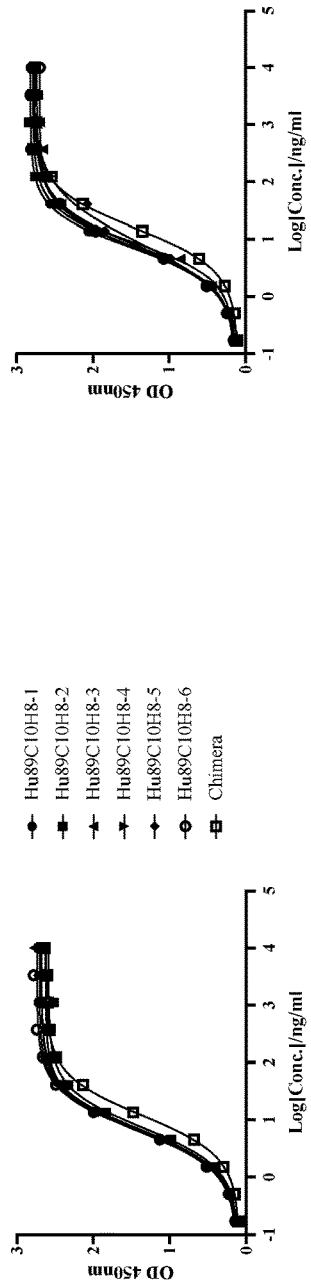
Figure 6C:
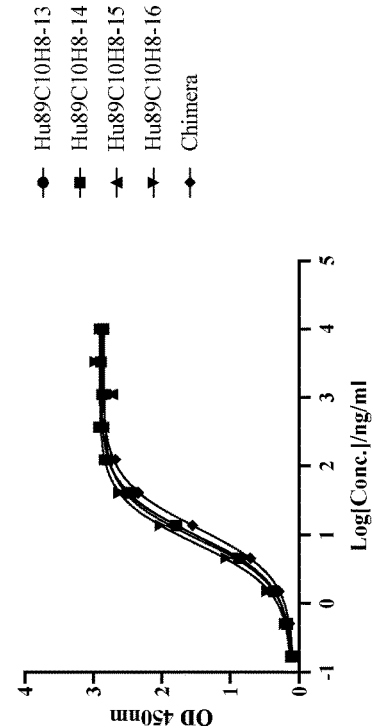

The binding of the 47C6A3, 67F3G7 and 89C10H8 antibodies to recombinant PD-L1 protein (human PD-L1-his tag) was tested with Biacore® using a capture method. The 47C6A3, 67F3G7 and 89C10H8 mAbs was captured using Protein A chip. A serial dilution of human PD-L1-his tag protein was injected over captured antibody for 2 mins at a flow rate of 30 µl/min. The antigen was allowed to dissociate for 480-1500 s. All the experiment were carried out on a Biacore T200. Data analysis was carried out using Biacore T200 evaluation software. The results are shown in FIG. 5 and Table 3 below.

TABLE 3

Affinity measured by biacore

| | PDL1-His | | |
|---|---|---|---|
| Abs | ka (1/Ms) | kd (1/s) | KD (M) |
| 47C6A3 | 1.851E+6 | 6.785E−4 | 3.665E−10 |
| 67F3G7 | 2.538E+6 | 6.193E−5 | 2.441E−11 |
| 89C10H8 | 1.597E+6 | 6.636E−5 | 4.154E−11 |

Example 5. Humanization of the Mouse Antibodies

The 47C6A3, 67F3G7, and 89C10H8 variable region genes were employed to create a humanized mAb. In the first step of this process, the amino acid sequences of the VH and VL or VK of 47C6A3, 67F3G7, and 89C10H8 were compared against the available database of human Ig gene sequences to find the overall best-matching human germline Ig gene sequences. For the light chain of 47C6A3, human Vk1-4 was the best fit germline, and for the heavy chain, human VH1-2 was chosen as the backbone. For the light chain of 67F3G7, the closest human match was the Vk1-39/JK4 gene, and for the heavy chain the closest human match was the VH1-2/JH4-FW4 gene. For the light chain of 89C10H8, the closest human match was the Vk1-17/JK2 gene, and for the heavy chain the closest human match was the VH3-21/JH3 gene.

For the VL of 47C6A3, human Vk1-4 was the best fit germline, and for VH of 47C6A3, human VH1-2 was chosen as the backbone. Humanized variable domain sequences of 47C6A3 were then designed where the CDRL1, L2, and L3 were grafted onto framework sequences of the Vk1-4 gene, and the CDRH1, H2, and H3 onto framework sequences of the VH1-2 gene. A 3D model was then generated to determine if there were any framework positions where replacing the mouse amino acid to the human amino acid could affect binding and/or CDR conformation. In the case of the heavy chain, R, M, and I in the framework was involved in back-mutations.

Humanized variable domain sequences of 67F3G7 were then designed where the CDRL1, L2 and L3 were grafted onto framework sequences of the Vk1-39/JK4 gene, and the CDRH1, H2, and H3 onto framework sequences of the VH1-2/JH4-FW4 gene. A 3D model was then generated to determine if there were any framework positions where replacing the mouse amino acid to the human amino acid could affect binding and/or CDR conformation. In the case of the heavy chain, V, K, T, and I in the framework was involved in back-mutations. In the case of the light chain, T, V, L, and Q in the framework was involved in back-mutations.

Humanized variable domain sequences of 89C10H8 were then designed where the CDRL1, L2 and L3 were grafted onto framework sequences of the Vk1-17/JK2 gene, and the CDRH1, H2, and H3 onto framework sequences of the VH3-21/JH3 gene. A 3D model was then generated to determine if there were any framework positions where replacing the mouse amino acid to the human amino acid could affect binding and/or CDR conformation. In the case of the heavy chain, A, T, I, and S in the framework was involved in back-mutations. In the case of the light chain, Y, I, E, and F in the framework was involved in back-mutations.

The amino acid and nucleotide sequences of some of the humanized antibody are listed in Table 4 below.

TABLE 4

Humanized antibody sequences (underlining indicates CDR; bold/italic indicates back mutations)

| 47C6A3 | Sequence | SEQ ID NO: |
|---|---|---|
| VH mouse | DVQLQESGPGLVKPSQSLSLTCTVTGYSITSDYAWNWIRQFPGNKLEWMGYIIYSGST SYNPSLKSRISITRDTSKNQFFLQLNSVTTEDTATYYCARSTMIATNWFAYWGQGTLV TVSA | 25 |
| VH-V0 | QVQLQESGPGLVKPSETLSLTCTVSGYSITSDYAWNWIRQPPGKGLEWIGYIIYSGST SYNPSLKSRVTISVDTSKNQFSLKLSSVTAADTAVYYCARSTMIATNWFAYWGQGTLV TVSS | 26 |
| VH-V1 | QVQLQESGPGLVKPSETLSLTCTVSGYSITSDYAWNWIRQPPGKGLEWIGYIIYSGST SYNPSLKS*R*VTISRDTSKNQFSLKLSSVTAADTAVYYCARSTMIATNWFAYWGQGTLV TVSS | 27 |
| VH-V2 | QVQLQESGPGLVKPSETLSLTCTVSGYSITSDYAWNWIRQPPGKGLEW*M*GYIIYSGST SYNPSLKS*R*ITISRDTSKNQFSLKLSSVTAADTAVYYCARSTMIATNWFAYWGQGTLV TVSS | 28 |
| VL mouse | DIVMTQSHKFMSTSVVDRVSITCKASQDVSLAVAWYQQKPGQSPKLLIYWASTRHTGV PDRFTGSGSGTDFALTISSVQAEDLALYYCQQHYITPWTFGGGTKLEIK | 29 |
| VL V0 | DIQMTQSPSSLSASVGDRVTITCKASQDVSLAVAWYQQKPGKAPKLLIYWASTRHTGV PSRFSGSGSGTDFTLTISSLQPEDFATYYCQQHYITPWTFGGGTKVEIK | 30 |

TABLE 4-continued

Humanized antibody sequences (underlining indicates CDR; bold/italic indicates back mutations)

| 67F3G7 | Sequence | SEQ ID NO: |
|---|---|---|
| VH mouse | QVKLLQSGAALVKPGASVKMSCKASGYIFT<u>DFWVS</u>WVKQSHEKSLEWIG<u>EIYPNSGVS RYNEKFKG</u>RATMTVDKSTSTAYLELSRLTSEDSAIYYCTK<u>YFGYTYWFGY</u>WGQGTLVT VSS | 31 |
| VH V0 | EVQLVQSGAEVKKPGASVKVSCKASGYTFT<u>DFWVS</u>WVRQAPGQGLEWMG<u>EIYPNSGVS RYNEKFKG</u>RVTMTRDTSISTAYMELSRLRSDDTAVYYCAR<u>YFGYTYWFGY</u>WGQGTLVT VSS | 32 |
| VH V1 | EVQLVQSGAEVKKPGASVKVSCKASGYTFT<u>DFWVS</u>WVRQAPGQGLEWMG<u>EIYPNSGVS RYNEKFKG</u>RVTMTVDKSISTAYMELSRLRSDDTAVYYCAR<u>YFGYTYWFGY</u>WGQGTLVT VSS | 33 |
| VH V2 | EVQLVQSGAEVKKPGASVKVSCKASGYTFT<u>DFWVS</u>WVRQAPGQGLEWMG<u>EIYPNSGVS RYNEKFKG</u>RVTMTVDKSISTAYMELSRLRSDDTAVYYC*TK*<u>YFGYTYWFGY</u>WGQGTLVT VSS | 34 |
| VH V3 | EVQLVQSGAEVKKPGASVKVSCKASGY*I*FT<u>DFWVS</u>WVRQAPGQGLEWIG<u>EIYPNSGVS RYNEKFKG</u>RVTMTVDKSISTAYMELSRLRSDDTAVYYC*TK*<u>YFGYTYWFGY</u>WGQGTLVT VSS | 35 |
| VH V4 | EVQLVQSGAEVKKPGASVKVSCKASGY*I*FT<u>DFWVS</u>WVRQAPGQGLEWIG<u>EIYPNSGVS RYNEKFKG</u>RVTMTVDKSISTAYMELSRLRSDDTAVYYCAR<u>YFGYTYWFGY</u>WGQGTLVT VSS | 36 |
| VH V5 | EVQLVQSGAEVKKPGASVKVSCKASGY*I*FT<u>DFWVS</u>WVRQAPG*K*GLEWIG<u>EIYPNSGVS RYNEKFKG</u>RVTMTVDKSISTAYMELSRLRSDDTAVYYC*TK*<u>YFGYTYWFGY</u>WGQGTLVT VSS | 37 |
| VL mouse | DTVLTQSPALAVSLGQRITISC<u>RASKSVSTYMH</u>WYQQRSGLQPKLLIY<u>SASHLES</u>GV PSRFSGSGSGTDFTLTIDPVEADDIANYYC<u>QQSNELPVT</u>FGSGTKLEIK | 38 |
| VL V0 | DIQMTQSPSSLSASVGDRVTITC<u>RASKSVSTYMH</u>WYQQKPGKAPKLLIY<u>SASHLES</u>GV PSRFSGSGSGTDFTLTISSLQPEDFATYYC<u>QQSNELPVT</u>FGGGTKVEIK | 39 |
| VL V1 | DTVLTQSPSSLSASVGDRVTITC<u>RASKSVSTYMH</u>WYQQKPGKAPKLLIY<u>SASHLES</u>GV PSRFSGSGSGTDFTLTISSLQPEDFATYYC<u>QQSNELPVT</u>FGGGTKVEIK | 40 |
| VL V2 | DTVLTQSPSSLSASVGDRVTITC<u>RASKSVSTYMH</u>WYQQKPGKQPKLLIY<u>SASHLES</u>GV PSRFSGSGSGTDFTLTISSLQPEDFATYYC<u>QQSNELPVT</u>FGGGTKVEIK | 41 |
| VL V3 | DTVLTQSPSLSASVGDRVTITC<u>RASKSVSTYMH</u>WYQQKPGKQPKLLIY<u>SASHLES</u>GV PSRFSGSGSGTDFTLTISSLQPEDFATYYC<u>QQSNELPVT</u>FGGGTKVEIK | 42 |
| VL V4 | DIQMTQSPSSLSASVGDRVTITC<u>RASKSVSTYMH</u>WYQQKPGKQPKLLIY<u>SASHLES</u>GV PSRFSGSGSGTDFTLTISSLQPEDFATYYC<u>QQSNELPVT</u>FGGGTKVEIK | 43 |

| 89C10H8 | Sequence | SEQ ID NO: |
|---|---|---|
| VH mouse | EVQLVESGGGLVQPGRSLTLSCVASGFTFS<u>NYWMT</u>WIRQAPGKGLEWVA<u>SITNTGSST FYPDSVKG</u>RFTISRDNTRSTLFLQINSLRSEDTATYYCTR<u>DTTIAPFDY</u>WGQGVMVTV SS | 44 |
| VH V0 | EVQLVESGGGLVKPGGSLRLSCAASGFTFS<u>NYWMT</u>WVRQAPGKGLEWVS<u>SITNTGSST FYPDSVKG</u>RFTISRDNAKNSLYLQMNSLRAEDTAVYYCAR<u>DTTIAPFDY</u>WGQGTMVTV SS | 45 |
| VH V1 | EVQLVESGGGLVKPGGSLRLSCAASGFTFS<u>NYWMT</u>WVRQAPGKGLEWVA<u>SITNTGSST FYPDSVKG</u>RFTISRDNAKNSLYLQMNSLRAEDTAVYYCAR<u>DTTIAPFDY</u>WGQGTMVTV SS | 46 |
| VH V2 | EVQLVESGGGLVKPGGSLRLSCAASGFTFS<u>NYWMT</u>WVRQAPGKGLEWVA<u>SITNTGSST FYPDSVKG</u>RFTISRDNAKNSLYLQMNSLRAEDTAVYYCTR<u>DTTIAPFDY</u>WGQGTMVTV SS | 47 |
| VH V3 | EVQLVESGGGLVKPGGSLRLSCAASGFTFS<u>NYWMT</u>W*I*RQAPGKGLEWVA<u>SITNTGSST FYPDSVKG</u>RFTISRDNAKNSLYLQMNSLRAEDTAVYYCTR<u>DTTIAPFDY</u>WGQGTMVTV SS | 48 |
| VH V4 | EVQLVESGGGLVKPGGSLRLSCAASGFTFS<u>NYWMT</u>W*I*RQAPGKGLEWVA<u>SITNTGSST FYPDSVKG</u>RFTISRDNAKSSLYLQMNSLRAEDTAVYYCTR<u>DTTIAPFDY</u>WGQGTMVTV SS | 49 |

TABLE 4-continued

Humanized antibody sequences (underlining indicates CDR; bold/italic indicates back mutations)

| | | |
|---|---|---|
| VL mouse | DIQMTQSPSFLSASVGDRVTITC<u>KASQNLNEYLN</u>WYQQKLGEAPKRLIY<u>KTNTLQAGI</u>PSRFSGSGSGIDYTLTISSLQPEDVATYFC<u>SQYNSGNT</u>FGAGTKLELK | 50 |
| VL V0 | DIQMTQSPSSLSASVGDRVTITC<u>KASQNLNEYLN</u>WYQQKPGKAPKRLIY<u>KTNTLQAGV</u>PSRFSGSGSGTDFTLTISSLQPEDFATYYC<u>SQYNSGNT</u>FGQGTKLEIK | 51 |
| VL V1 | DIQMTQSPSSLSASVGDRVTITC<u>KASQNLNEYLN</u>WYQQKPGKAPKRLIY<u>KTNTLQAGV</u>PSRFSGSGSGTDYTLTISSLQPEDFATYYC<u>SQYNSGNT</u>FGQGTKLEIK | 52 |
| VL V2 | DIQMTQSPSSLSASVGDRVTITC<u>KASONLNEYLN</u>WYQQKPGKAPKRLIY<u>KTNTLQAGI</u>PSRFSGSGSGTDYTLTISSLQPEDFATYYC<u>SQYNSGNT</u>FGQGTKLEIK | 53 |
| VL V3 | DIQMTQSPSSLSASVGDRVTITC<u>KASQNLNEYLN</u>WYQQKPGKAPKRLIY<u>KTNTLQAGI</u>PSRFSGSGSGIDYTLTISSLQPEDFATYYC<u>SQYNSGNT</u>FGQGTKLEIK | 54 |
| VL V4 | DIQMTQSPSSLSASVGDRVTITC<u>KASQNLNEYLN</u>WYQQKLGEAPKRLIY<u>KTNTLQAGI</u>PSRFSGSGSGIDYTLTISSLQPEDFATYFC<u>SQYNSGNT</u>FGQGTKLEIK | 55 |

The genes were cloned in pcDNA 3.4 vector and transfected into 293F cells. The antibodies were produced according to the following table.

The humanized VH and VL genes were produced synthetically and then respectively cloned into vectors containing the human gamma 1 and human kappa constant domains. The pairing of the human VH and the human VL created the 41 humanized antibodies (see Table 5).

TABLE 5

Humanized antibodies with their VH an VL regions

A. 47C6A3

| VH VL | 47C6A3 VL | 47C6A3 VL-V0 |
|---|---|---|
| 47C6A3 VH | 47C6A3-chimera | |
| 47C6A3 VH.V0 | | Hu47C6A3-1 |
| 47C6A3 VH.V1 | | Hu47C6A3-2 |
| 47C6A3 VH.V2 | | Hu47C6A3-3 |

B. 67F3G7

| VH VL | 67F3G7 VL.V0 | 67F3G7 VL.V1 | 67F3G7 VL.V2 | 67F3G7 VL.V3 | 67F3G7 VL.V4 | 67F3G7 VL |
|---|---|---|---|---|---|---|
| 67F3G7 VH.V1 | Hu 67F3G7-1 | Hu 67F3G7-6 | Hu 67F3G7-11 | Hu 67F3G7-16 | Hu 67F3G7-21 | |
| 67F3G7 VH.V2 | Hu 67F3G7-2 | Hu 67F3G7-7 | Hu 67F3G7-12 | Hu 67F3G7-17 | Hu 67F3G7-22 | |
| 67F3G7 VH.V3 | Hu 67F3G7-3 | Hu 67F3G7-8 | Hu 67F3G7-13 | Hu 67F3G7-18 | | |
| 67F3G7 VH.V4 | Hu 67F3G7-4 | Hu 67F3G7-9 | Hu 67F3G7-14 | Hu 67F3G7-19 | | |
| 67F3G7 VH.V5 | Hu 67F3G7-5 | Hu 67F3G7-10 | Hu 67F3G7-15 | Hu 67F3G7-20 | | |
| 67F3G7 VH | | | | | | 67F3G7-chimera |

C. 89C10H8

| VH VL | 89C10H8 VL.V1 | 89C10H8 VL.V2 | 89C10H8 VL.V3 | 89C10H8 VL.V4 | 89C10H8 VL |
|---|---|---|---|---|---|
| 89C10H8 VH.V1 | Hu 89C10H8-1 | Hu 89C10H8-5 | Hu 89C10H8-9 | Hu 89C10H8-13 | |
| 89C10H8 VH.V2 | Hu 89C10H8-2 | Hu 89C10H8-6 | Hu 89C10H8-10 | Hu 89C10H8-14 | |
| 89C10H8 VH.V3 | Hu 89C10H8-3 | Hu 89C10H8-7 | Hu 89C10H8-11 | Hu 89C10H8-15 | |
| 89C10H8 VH.V4 | Hu 89C10H8-4 | Hu 89C10H8-8 | Hu 89C10H8-12 | Hu 89C10H8-16 | |
| 89C10H8 VH | | | | | 89C10H8-chimera |

Example 6: Antigen Binding Properties of the Humanized Antibodies

Binding to Recombinant Human PD-L1

To evaluate antigen binding activity, the humanized antibodies were subjected to ELISA test. Briefly, microtiter plates were coated with human PD-L1-Fc protein at 0.5 µg/ml in PBS, 100 µl/well at 4° C. overnight, then blocked with 200 µl/well of 1% BSA. Three-fold dilutions of humanized antibodies starting from 10 µg/ml were added to each well and incubated for 1 hour at 37° C. The plates were washed with PBS/Tween and then incubate with mouse-anti-human IgG Fab antibody conjugated with Horse Radish Peroxidase (HRP) for 1 hour at 37° C. After washing, the plates were developed with TMB substrate and analyzed by spectrophotometer at OD 450 nm. As shown in FIG. 6, all the humanized antibodies showed comparable binding efficacy to human PD-L1 to the chimeric antibody.

To explore the binding kinetics of the humanized antibody, this example performed the affinity ranking by using Biacore®. As shown in Table 6, Hu67F3G7-2, Hu67F3-G7-3, Hu67F3G7-5, Hu67F3G7-7, Hu67F3G7-22, Hu89C10H8-4, Hu89C10H8-7, Hu89C10H8-11, and Hu89C10H8-12 showed high affinity, which is comparable to chimeric antibody.

TABLE 6

Affinity ranking of humanized antibodies

| Abs | PDL1-His | | |
|---|---|---|---|
| | ka (1/Ms) | kd (1/s) | KD (M) |
| Hu67F3G7-1 | 1.855E+6 | 1.214E-4 | 6.548E-11 |
| Hu67F3G7-2 | 2.569E+6 | 9.748E-5 | 3.795E-11 |
| Hu67F3G7-3 | 2.803E+6 | 9.716E-5 | 3.466E-11 |
| Hu67F3G7-4 | 1.883E+6 | 1.031E-4 | 5.477E-11 |
| Hu67F3G7-5 | 2.621E+6 | 9.711E-5 | 3.704E-11 |
| Hu67F3G7-6 | 2.006E+6 | 1.177E-4 | 5.867E-11 |
| Hu67F3G7-7 | 2.687E+6 | 9.493E-5 | 3.533E-11 |
| Hu67F3G7-8 | 2.765E+6 | 9.844E-5 | 3.560E-11 |
| Hu67F3G7-9 | 2.214E+6 | 1.004E-4 | 4.535E-11 |
| Hu67F3G7-10 | 2.383E+6 | 9.335E-5 | 3.918E-11 |
| Hu67F3G7-11 | 5.114E+6 | 1.643E-4 | 3.213E-11 |
| Hu67F3G7-12 | 2.565E+6 | 9.013E-5 | 3.513E-11 |
| Hu67F3G7-13 | 2.798E+6 | 9.535E-5 | 3.408E-11 |
| Hu67F3G7-14 | 2.092E+6 | 1.086E-4 | 5.191E-11 |
| Hu67F3G7-15 | 2.610E+6 | 9.688E-5 | 3.712E-11 |
| Hu67F3G7-16 | 1.478E+6 | 1.114E-4 | 7.537E-11 |
| Hu67F3G7-17 | 2.741E+6 | 1.014E-4 | 3.698E-11 |
| Hu67F3G7-18 | 2.876E+6 | 9.511E-5 | 3.307E-11 |
| Hu67F3G7-19 | 1.970E+6 | 1.074E-4 | 5.451E-11 |
| Hu67F3G7-20 | 2.698E+6 | 9.363E-5 | 3.471E-11 |
| Hu67F3G7-21 | 5.399E+5 | 8.425E-5 | 1.560E-10 |
| Hu67F3G7-22 | 1.669E+6 | 7.261E-5 | 4.351E-11 |
| Hu89C10H8-1 | 7.541E+5 | 4.654E-4 | 6.172E-10 |
| Hu89C10H8-2 | 6.411E+5 | 8.506E-5 | 1.327E-10 |
| Hu89C10H8-3 | 7.375E+5 | 5.793E-5 | 7.855E-11 |
| Hu89C10H8-4 | 6.230E+5 | 5.944E-5 | 9.542E-11 |
| Hu89C10H8-5 | 6.707E+5 | 4.939E-4 | 7.364E-10 |
| Hu89C10H8-6 | 7.010E+5 | 8.560E-5 | 1.221E-10 |
| Hu89C10H8-7 | 6.150E+5 | 6.613E-5 | 1.075E-10 |
| Hu89C10H8-8 | 6.550E+5 | 6.663E-5 | 1.017E-10 |
| Hu89C10H8-9 | 6.712E+5 | 4.784E-4 | 7.127E-10 |
| Hu89C10H8-10 | 5.950E+5 | 8.988E-5 | 1.511E-10 |
| Hu89C10H8-11 | 7.001E+5 | 6.732E-5 | 9.615E-11 |
| Hu89C10H8-12 | 7.269E+5 | 7.036E-5 | 9.680E-11 |
| Hu89C10H8-13 | 7.644E+5 | 4.327E-4 | 5.611E-10 |
| Hu89C10H8-14 | 7.125E+5 | 9.752E-5 | 1.369E-10 |
| Hu89C10H8-15 | 7.814E+5 | 7.170E-5 | 9.176E-11 |
| Hu89C10H8-16 | 6.671E+5 | 6.537E-5 | 9.799E-11 |

Binding to Human PD-L1 Overexpressed on Mammalian Cells

Figure 7:
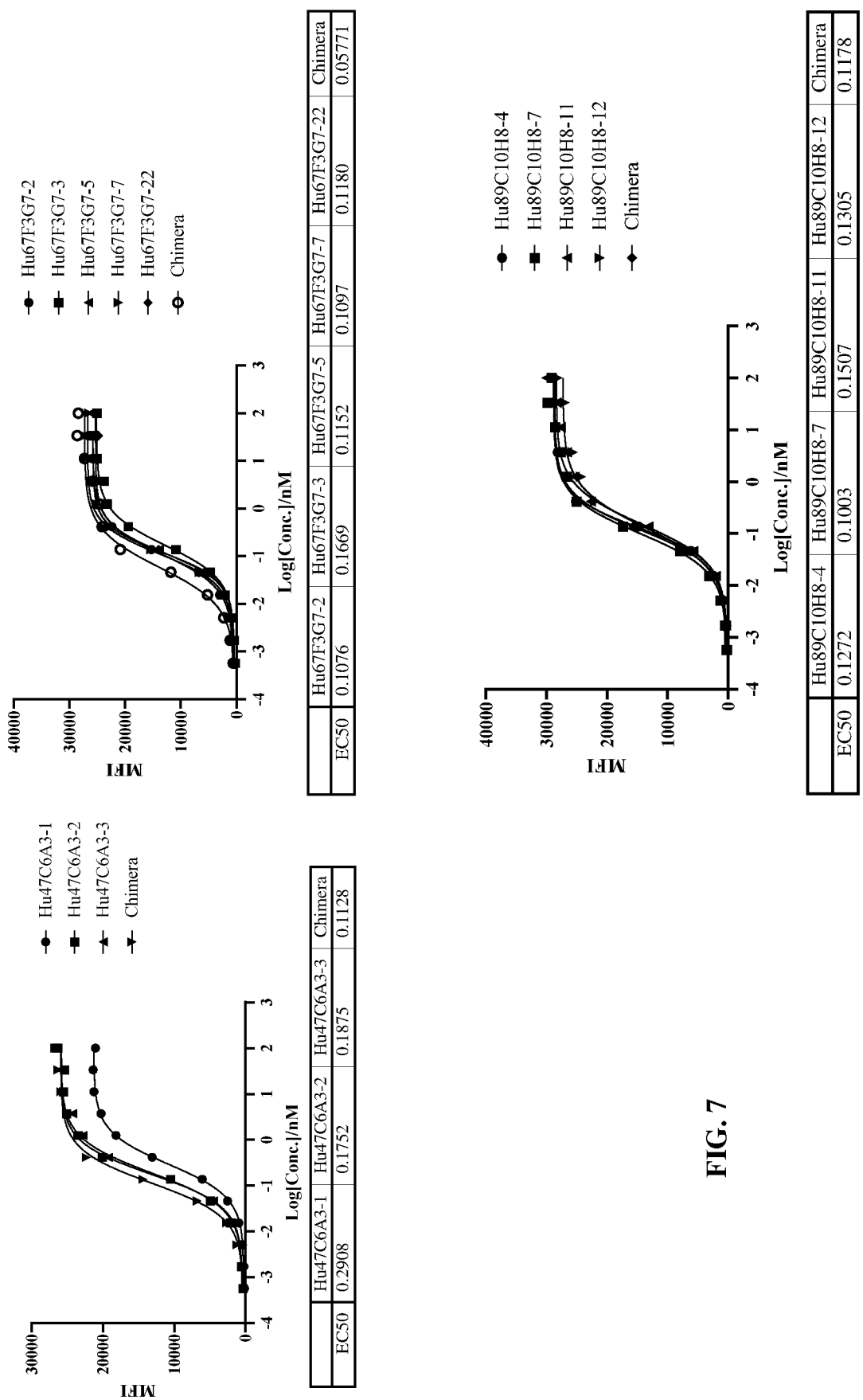
FIG. 7 shows that tested humanized antibodies can high efficiently bind to PD-L1 expressed on mammalian cells, comparable with chimeric antibody.
Figure 8A:
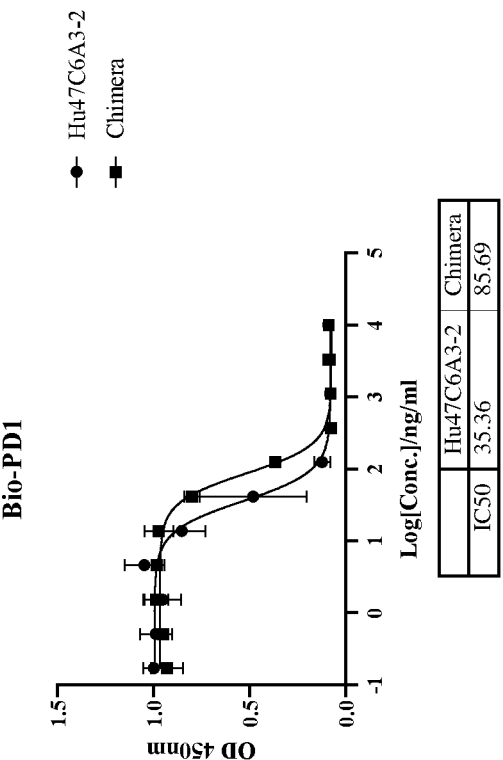
FIG. 8A-C show that some humanized antibodies can efficiently inhibit the binding of human PD-L1 to human PD1.
Figure 8A:
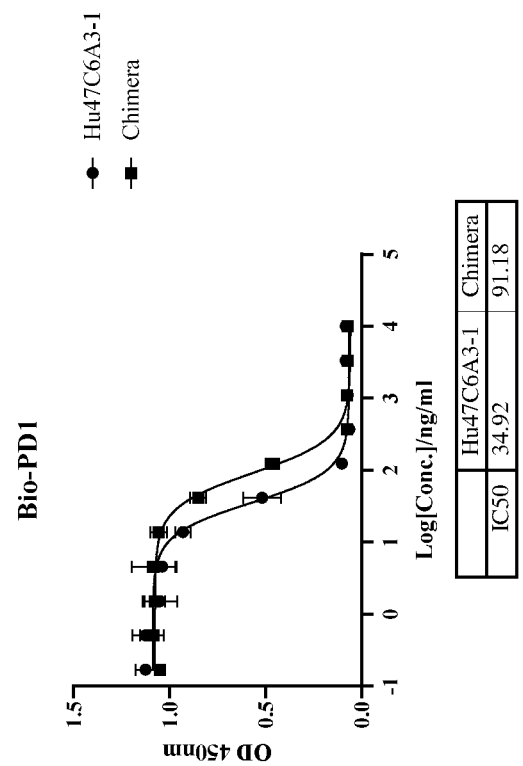
Figure 8A:
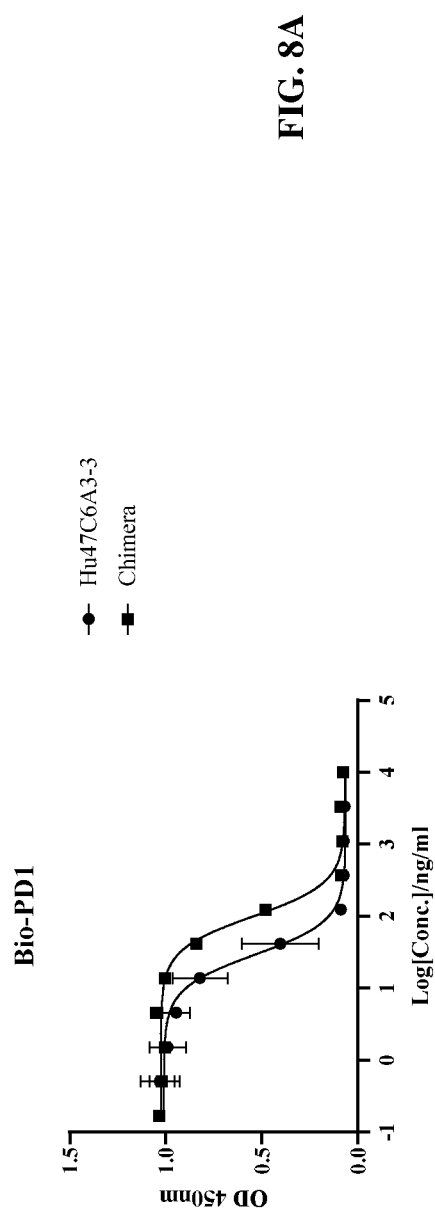
Figure 8B:
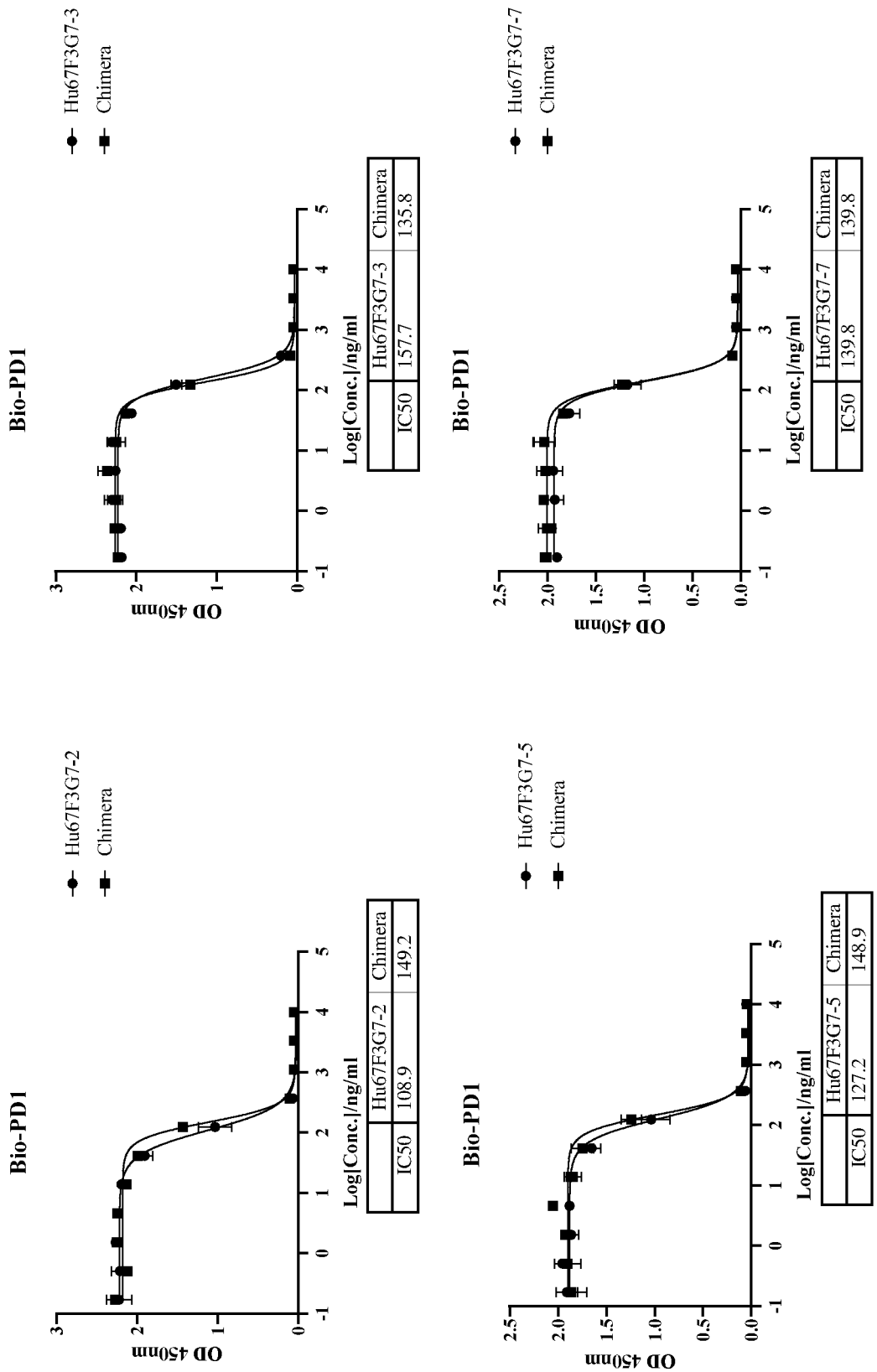
Figure 8B:
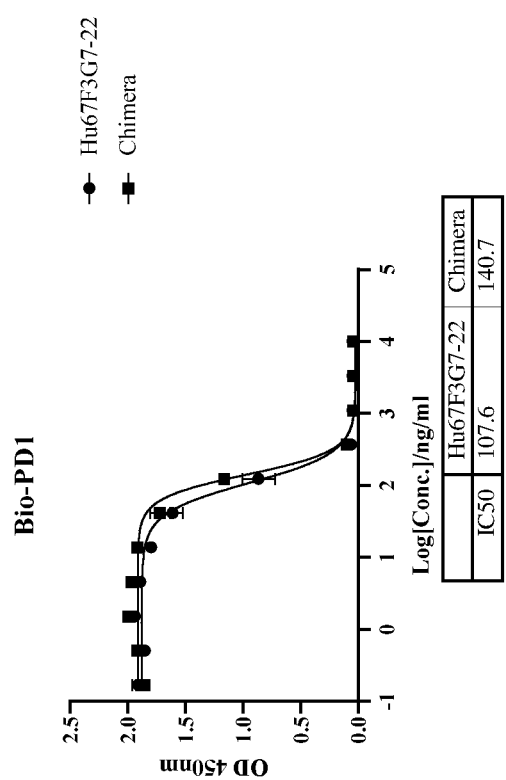
Figure 8C:
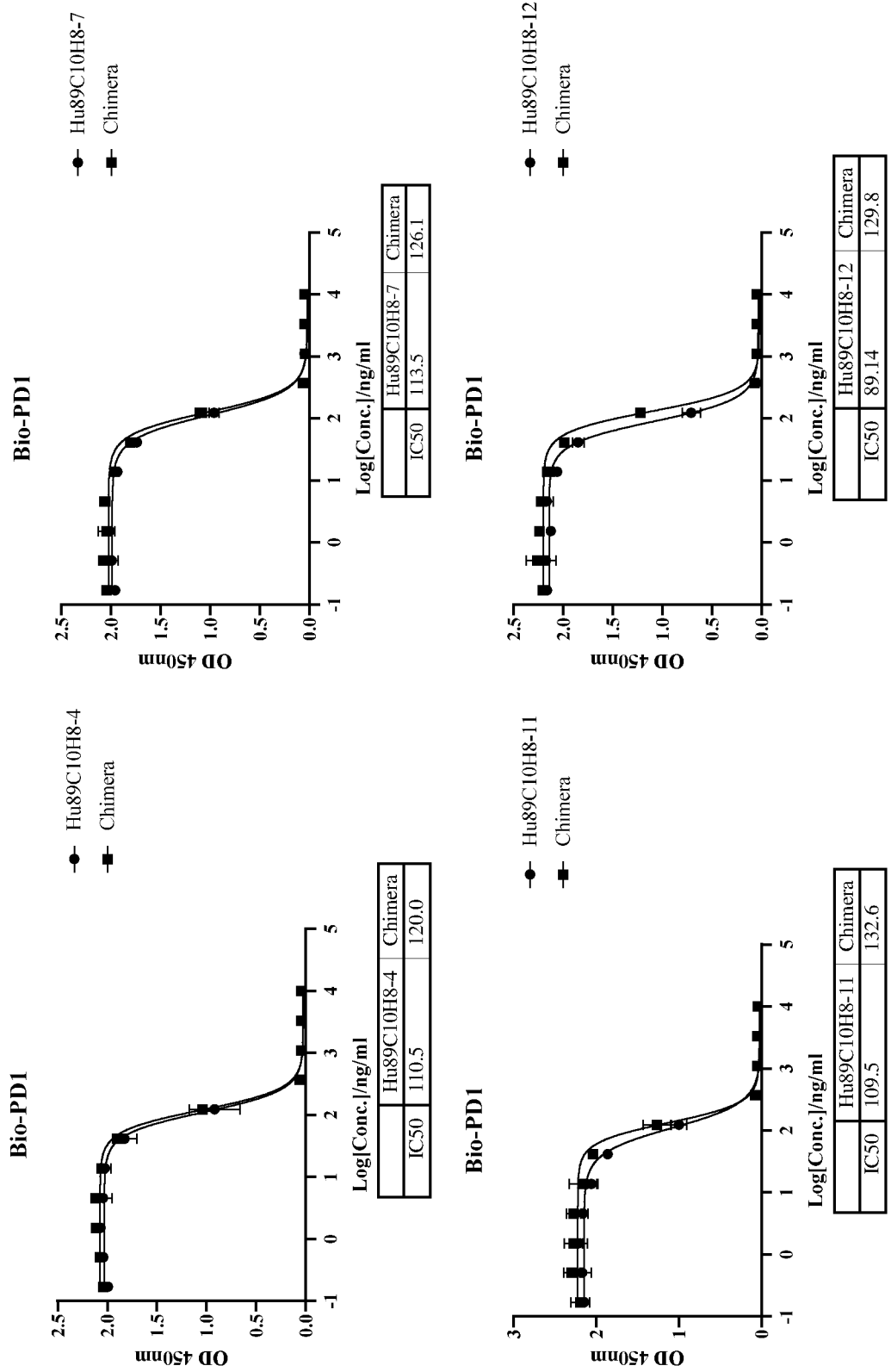
Figure 9A:
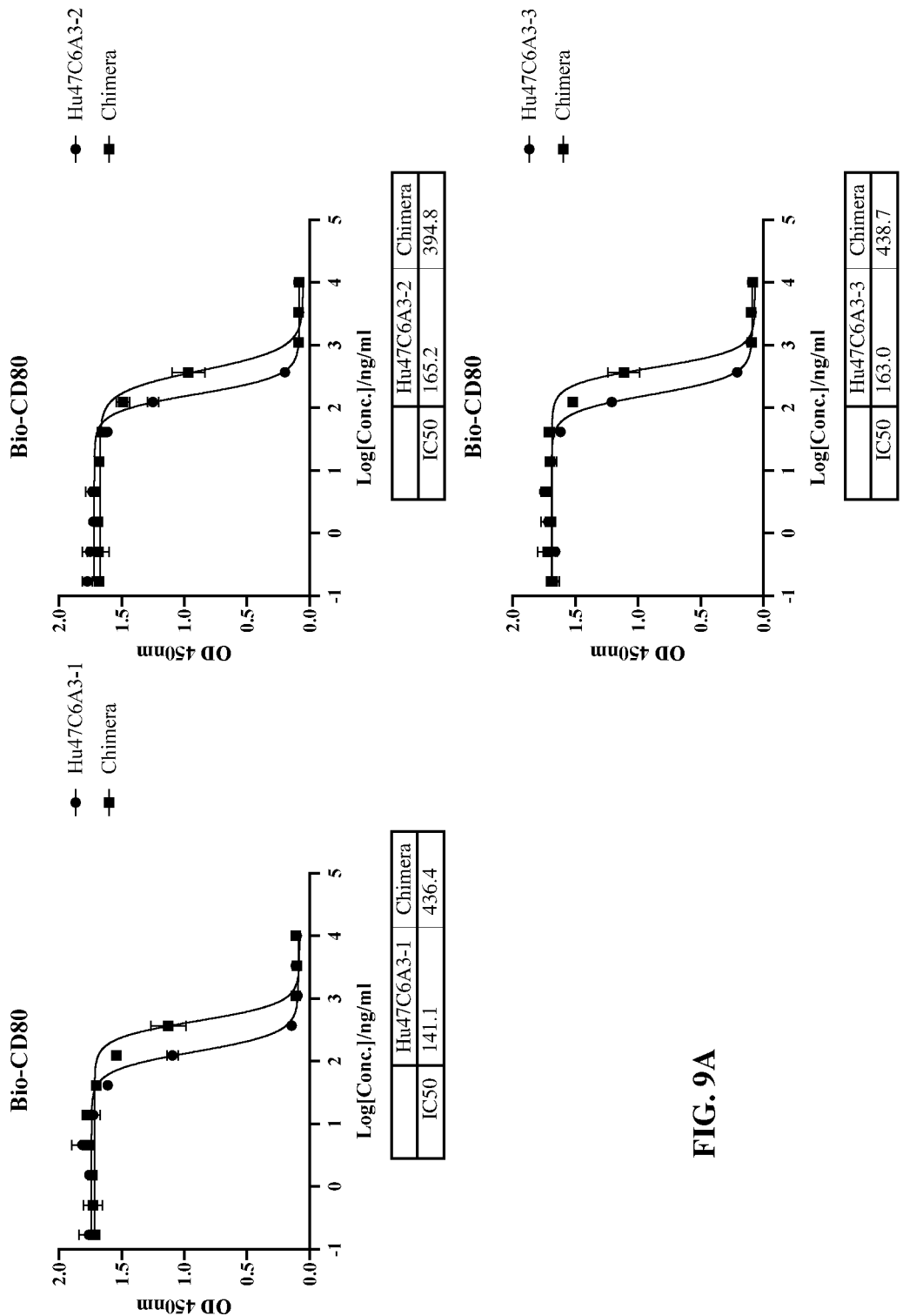
FIG. 9A-C show that some humanized antibodies can efficiently inhibit the binding of human PD-L1 to human CD80.
Figure 9B:
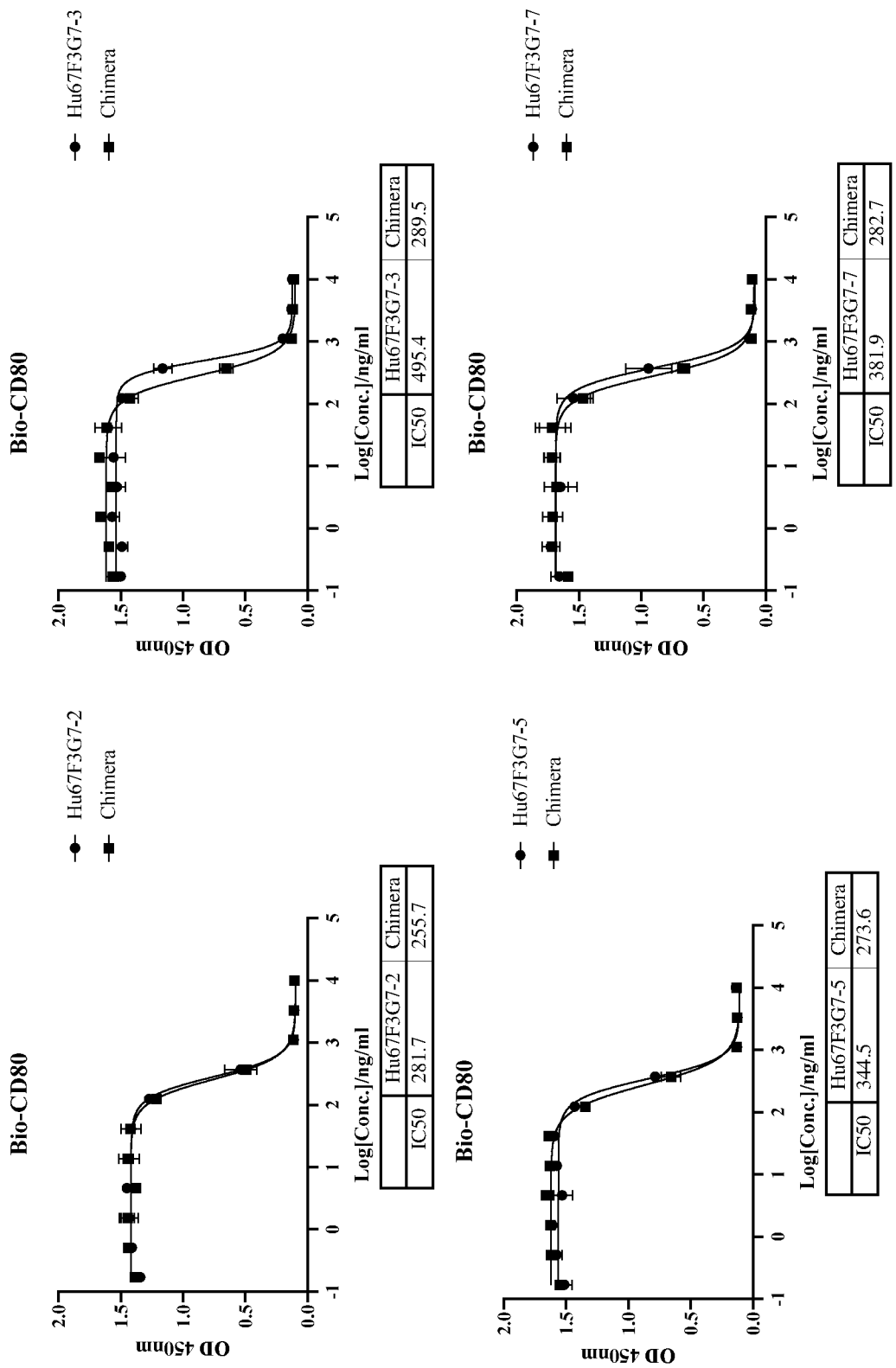
Figure 9B:
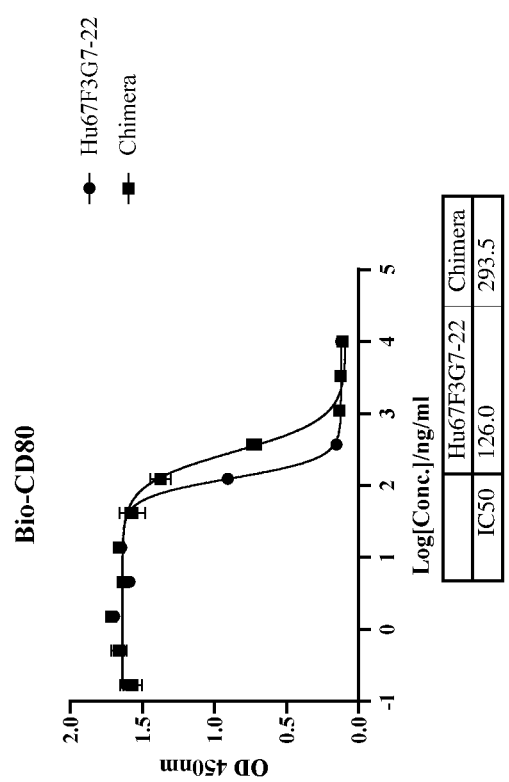
Figure 9C:
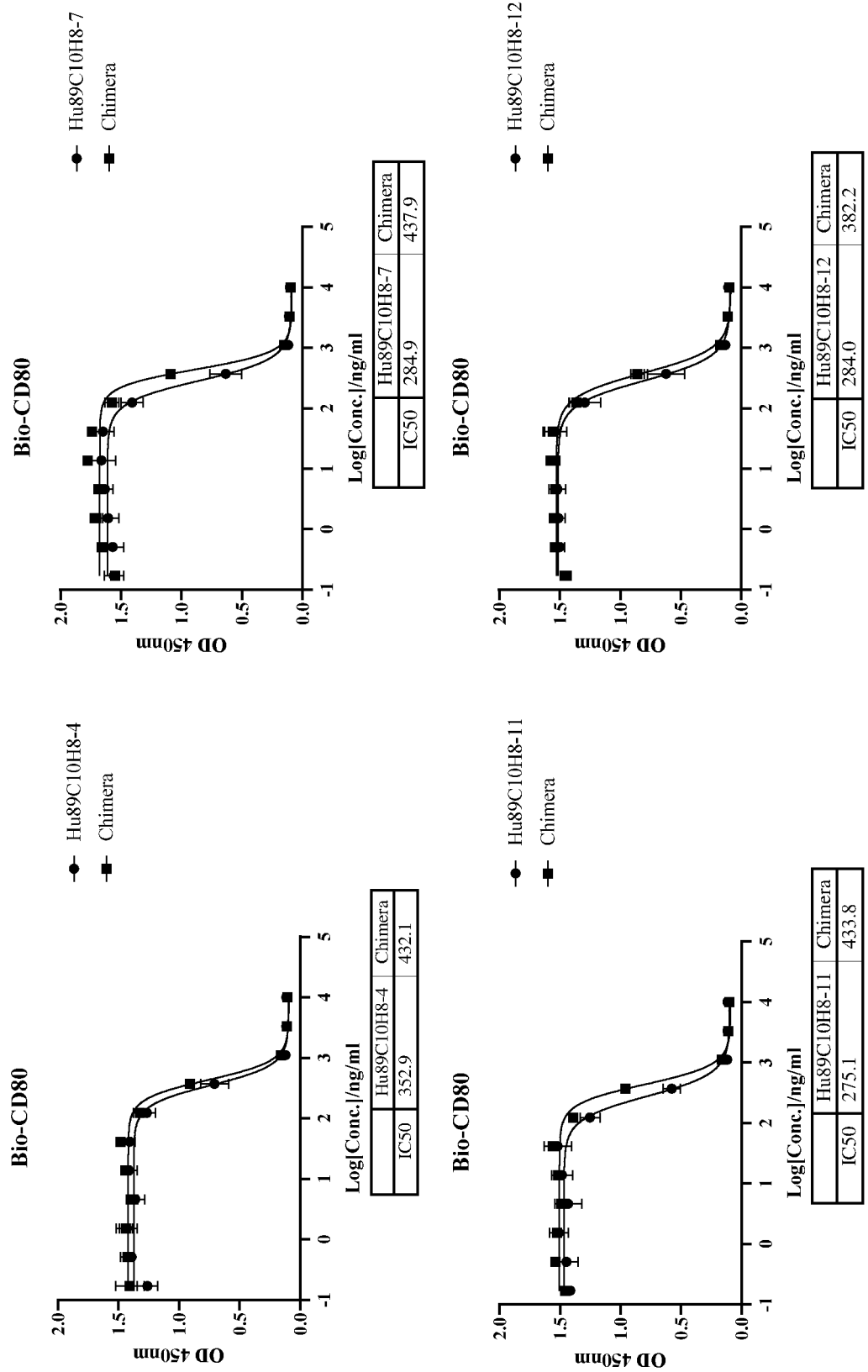

To evaluate the antigen binding property, the humanized antibodies were analyzed for their binding to PD-L1 overexpressed on mammalian cells by FACS. Briefly, PDL1-CHOK1 cells were firstly incubated with 3-fold serious diluted humanized antibodies starting at 15 µg/ml at 4° C. for 40 mins. After wash by PBS, the Alexa Fluor® 647 AffiniPure Goat Anti-Human IgG (H+L) antibody was added to each well and incubated at 4° C. for 30 mins. The MFI of Alexa Fluor® 647 were evaluated by FACSCanto. As shown in FIG. 7, all the humanized antibodies can high efficiently bind to PD-L1 expressed on mammalian cells.

Full Kinetic Affinity of Humanized Antibodies by Biacore®

The binding of the humanized antibodies to recombinant PD-L1 protein (human PD-L1-his tag) was tested by Biacore® using a capture method. Hu47C6A3-1, Hu47C6A3-2, Hu47C6A3-3, Hu67F3G7-2, Hu67F3G7-3, Hu67F3G7-5, Hu67F3G7-7, Hu67F3G7-22, Hu89C10H8-4, Hu89C10H8-7, Hu89C10H8-11, and Hu89C10H8-12 mAbs were captured using Protein A chip. A serial dilution of human PD-L1-his tag protein was injected over captured antibody for 2 mins at a flow rate of 30 µl/min. The antigen was allowed to dissociate for 1500 s. All the experiment were carried out on a Biacore T200. Data analysis was carried out using Biacore T200 evaluation software and is shown in Table 7 below.

TABLE 7

Affinity by Biacore

| Abs | PDL1-His | | |
|---|---|---|---|
| | ka (1/Ms) | kd (1/s) | KD (M) |
| HSP209-chi | 1.851E+6 | 6.785E-4 | 3.665E-10 |
| Hu47C6A3-1 | 1.235E+6 | 5.933E-4 | 4.805E-10 |
| Hu47C6A3-2 | 2.451E+6 | 9.000E-4 | 3.672E-10 |
| Hu47C6A3-3 | 2.176E+6 | 9.661E-4 | 4.440E-10 |
| Hu67F3G7-2 | 1.915E+6 | 7.032E-5 | 3.672E-11 |
| Hu67F3G7-3 | 2.088E+6 | 7.737E-5 | 3.706E-11 |
| Hu67F3G7-5 | 1.838E+6 | 7.920E-5 | 4.310E-11 |
| Hu67F3G7-7 | 2.211E+6 | 7.252E-5 | 3.280E-11 |
| Hu67F3G7-22 | 1.779E+6 | 5.791E-5 | 3.256E-11 |
| Hu89C10H8-4 | 5.623E+5 | 5.408E-5 | 9.618E-11 |
| Hu89C10H8-7 | 5.685E+5 | 5.313E-5 | 9.346E-11 |
| Hu89C10H8-11 | 5.640E+5 | 5.542E-5 | 9.826E-11 |
| Hu89C10H8-12 | 5.867E+5 | 5.587E-5 | 9.522E-11 |

Example 7: Blockade the Binding of PDL1 to PD1 by Humanized Antibodies

Receptor Blocking Assay by Using Recombinant Human PD-L1

There are two receptors, PD-1 and CD80, for human PD-L1. To explore the blocking property of humanized PD-L1 antibody to these two proteins, protein based receptor blocking assay was employed here.

Briefly, microtiter plates were coated with human PD-L1-Fc protein at 0.5 µg/ml in PBS, 100 µl/well at 4° C. overnight, then blocked with 150 µl/well of 1% BSA at 37° C. for 2 hours. 50 µl biotin-labeled human PD-1-Fc or CD80-Fc protein and 3-fold dilutions of PD-L1 antibodies starting from 10 µg/ml at 50 µl were added to each well and incubated for 1 hour at 37° C. The plates were washed with PBS/Tween and then incubated with Streptavidin-HRP for 10 mins at 37° C. After washing, the plates were developed with TMB substrate and analyzed by spectrophotometer at OD 450 nm. As shown in FIG. 8, Hu47C6A3-1, Hu47C6A3-2, Hu47C6A3-3, Hu67F3G7-2, Hu67F3G7-3, Hu67F3G7-5, Hu67F3G7-7, Hu67F3G7-22, Hu89C10H8-4, Hu89C10H8-7, Hu89C10H8-11, and Hu89C10H8-12 efficiently inhibited the binding of human PD-L1 to human PD1. Moreover, Hu47C6A3-1, Hu47C6A3-2, Hu47C6A3-3, Hu67F3G7-2, Hu67F3G7-3, Hu67F3G7-5, Hu67F3G7-7, Hu67F3G7-22, Hu89C10H8-4, Hu89C10H8-7, Hu89C10H8-11, and Hu89C10H8-12 efficiently inhibited the binding of human PD-L1 to human B7-1 dose dependently (FIG. 9).

Example 8. Bifunctional Protein Targeting for Both PD-L1 and TGF-β Pathways

Bifunctional recombinant anti-PD-L1 antibody and TGF-β RII fusion proteins were prepared and tested in this example.

The light chain of the molecule is the light chain of an anti-PDL1 mAb. The heavy chain is a fusion of the heavy chain of the anti-PDL1 mAb, via a flexible (Gly$_4$Ser)$_4$Gly linker, to the N-terminus of the soluble extracellular domain of TGF-β RII. At the fusion junction, the C-terminal lysine residue of the antibody heavy chain was mutated to alanine to reduce potential proteolytic cleavage.

In some examples, potential modification sites in the CDRs were mutated to similar amino acids. The sequences of the anti-PD-L1 portion are shown in Table 8 below.

TABLE 8

Sequences of the variable regions of antibody portion in the bifunctional molecules

| Name | Sequence | SEQ ID NO: |
|---|---|---|
| 02 VH (67F3G7 VH V2) | EVQLVQSGAEVKKPGASVKVSCKASGYTFTDFWVSWVRQAPGQGLEWMGE IYPNSGVSRYNEKFKGRVTMTVDKSISTAYMELSRLRSDDTAVYYCTKYF GYTYWFGYWGQGTLVTVSS | 34 |
| 02 VL (67F3G7 VL V4) | DIQMTQSPSSLSASVGDRVTITCRASKSVSTYMHWYQQKPGKQPKLLIYS ASHLESGVPSRFSGSGSGTDFTLTISSLQPEDFATYYCQQSNELPVTFGG GTKVEIK | 43 |
| 06 VH (89C10H8 VH V3) | EVQLVESGGGLVKPGGSLRLSCAASGFTFSNYWMTWIRQAPGKGLEWVAS ITNTGSSTFYPDSVKGRFTISRDNAKNSLYLQMNSLRAEDTAVYYCTRDT TIAPFDYWGQGTMVTVSS | 48 |
| 06 VL (89C10H8 VLV2) | DIQMTQSPSSLSASVGDRVTITCKASQNLNEYLNWYQQKPGKAPKRLIYK TNTLQAGIPSRFSGSGSGTDYTLTISSLQPEDFATYYCSQYNSGNTFGQ GTKLEIK | 53 |
| 06a VH (89C10H8 VH V3) | EVQLVESGGGLVKPGGSLRLSCAASGFTFSNYWMTWIRQAPGKGLEWVAS ITNTGSSTFYPDSVKGRFTISRDNAKNSLYLQMNSLRAEDTAVYYCTRDT TIAPFDYWGQGTMVTVSS | 48 |
| 06a VL | DIQMTQSPSSLSASVGDRVTITCKASQNLNEYLNWYQQKPGKAPKRLIYK TNTLQAGIPSRFSGSGSGTDYTLTISSLQPEDFATYYCSQYQSGNTFGQ GTKLEIK | 56 |
| 06a-DA VH | EVQLVESGGGLVKPGGSLRLSCAASGFTFSNYWMTWIRQAPGKGLEWVAS ITNTGSSTFYPDAVKGRFTISRDNAKNSLYLQMNSLRAEDTAVYYCTRDT TIAPFDYWGQGTMVTVSS | 57 |
| 06a-ES VH | EVQLVESGGGLVKPGGSLRLSCAASGFTFSNYWMTWIRQAPGKGLEWVAS ITNTGSSTFYPESVKGRFTISRDNAKNSLYLQMNSLRAEDTAVYYCTRDT TIAPFDYWGQGTMVTVSS | 58 |
| 89C10H8 CDRH2 DA | SITNTGSSTFYPDAVKG | 91 |
| 89C10H8 CDRH2 ES | SITNTGSSTFYPESVKG | 92 |

TABLE 9

VH/VL of the bifunctional molecules

| Bifunctional molecule | VH | VL |
|---|---|---|
| LP008-02 | 02 VH | 02 VL |
| LP008-06 | 06 VH | 06 VL |
| LP008-06a | 06a VH | 06a VL |
| LP008-06a-DA | 06a-DA VH | 06a VL |
| LP008-06a-ES | 06a-ES VH | 06a VL |

Besides the VH, the heavy chain of the bifunctional molecule further includes constant regions (with C-terminal K mutated to A), the (Gly₄Ser)₄Gly linker, and the N-terminus of the soluble extracellular domain of TGF-β RII. Their sequences are shown in Table 10.

TABLE 10

Additional sequences of the heavy chain, and entire heavy/ light chains

| Name | Sequence | SEQ ID NO: |
|---|---|---|
| Heavy chain constant regions | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEP KSCDKTHTCPPCPAPELLGGPSVFLFPPKPKDTLMISRTPEVICVVVDVS HEDPEVKFNWYVDGVEVHNAKTKPREEQYNSTYRVVSVLTVLHQDWLNGK | 59 |

TABLE 10-continued

Additional sequences of the heavy chain, and entire heavy/light chains

| Name | Sequence | SEQ ID NO: |
|---|---|---|
| | EYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGA | |
| $(Gly_4Ser)_4Gly$ linker | GGGGSGGGGSGGGGSGGGGSG | 60 |
| TGF-β RII extracellular domain | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 61 |
| LP008-02 heavy chain | EVQLVQSGAEVKKPGASVKVSCKASGYTFTDFWVSWVRQAPGQGLEWMGEIYPNSGVSRYNEKFKGRVTMTVDKSISTAYMELSRLRSDDTAVYYCTKYFGYTYWFGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDILMISRTPEVICVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGAGGGGSGGGGSGGGGSGGGGSGIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 62 |
| LP008-06 heavy chain | EVQLVESGGGLVKPGGSLRLSCAASGFTFSNYWMTWIRQAPGKGLEWVASITNTGSSTFYPDSVKGRFTISRDNAKNSLYLQMNSLRAEDTAVYYCTRDTTIAPFDYWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVICVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGAGGGGSGGGGSGGGGSGGGGSGIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 63 |
| LP008-06a heavy chain | EVQLVESGGGLVKPGGSLRLSCAASGFTFSNYWMTWIRQAPGKGLEWVASITNTGSSTFYPDSVKGRFTISRDNAKNSLYLQMNSLRAEDTAVYYCTRDTTIAPFDYWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVICVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGAGGGGSGGGGSGGGGSGGGGSGIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 64 |
| LP008-06a-DA heavy chain | EVQLVESGGGLVKPGGSLRLSCAASGFTFSNYWMTWIRQAPGKGLEWVASITNTGSSTFYPDAVKGRFTISRDNAKNSLYLQMNSLRAEDTAVYYCTRDTTIAPFDYWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVICVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGAGGGGSGGGGSGGGGSGGGGSGIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 65 |
| LP008-06a-ES heavy chain | EVQLVESGGGLVKPGGSLRLSCAASGFTFSNYWMTWIRQAPGKGLEWVASITNTGSSTFYPESVKGRFTISRDNAKNSLYLQMNSLRAEDTAVYYCTRDTTIAPFDYWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVICVVVDVSHEDPEVKFNWYVDGVEVHNAKTKPREEQYNSTYRVVSVLTVLHQDWLNGKEYKCKVSNKALPAPIEKTISKAKGQPREPQVY | 66 |

TABLE 10-continued

Additional sequences of the heavy chain, and entire heavy/light chains

| Name | Sequence | SEQ ID NO: |
|---|---|---|
| | TLPPSREEMTKNQVSLTCLVKGFYPSDIAVEWESNGQPENNYKTTPPVLD SDGSFFLYSKLTVDKSRWQQGNVFSCSVMHEALHNHYTQKSLSLSPGAGG GGSGGGGSGGGGSGGGGSGIPPHVQKSVNNDMIVTDNNGAVKFPQLCKFC DVRFSTCDNQKSCMSNCSITSICEKPQEVCVAVWRKNDENITLETVCHDP KLPYHDFILEDAASPKCIMKEKKKPGETFFMCSCSSDECNDNIIFSEEYN TSNPD | |
| LP008-02 light chain | DIQMTQSPSSLSASVGDRVTITCRASKSVSTYMHWYQQKPGKQPKLLIYS ASHLESGVPSRFSGSGSGTDFTLTISSLQPEDFATYYCQQSNELPVTFGG GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 67 |
| LP008-06 light chain | DIQMTQSPSSLSASVGDRVTITCKASQNLNEYLNWYQQKPGKAPKRLIYK TNTLQAGIPSRFSGSGSGTDYTLTISSLQPEDFATYYCSQYNSGNTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 68 |
| LP008-06a (& DA/ES) light chain | DIQMTQSPSSLSASVGDRVTITCKASQNLNEYLNWYQQKPGKAPKRLIYK TNTLQAGIPSRFSGSGSGTDYTLTISSLQPEDFATYYCSQYQS-GNTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC | 69 |

Example 9: The Binding Affinity of the Bifunctional Molecules

The binding of the LP008-06, LP008-06a, LP008-06a-DA, and LP008-06a-ES bifunctional molecules to recombinant PD-L1 protein (human PD-L1-his tag) was tested with Biacore® using a capture method.

Figure 10:
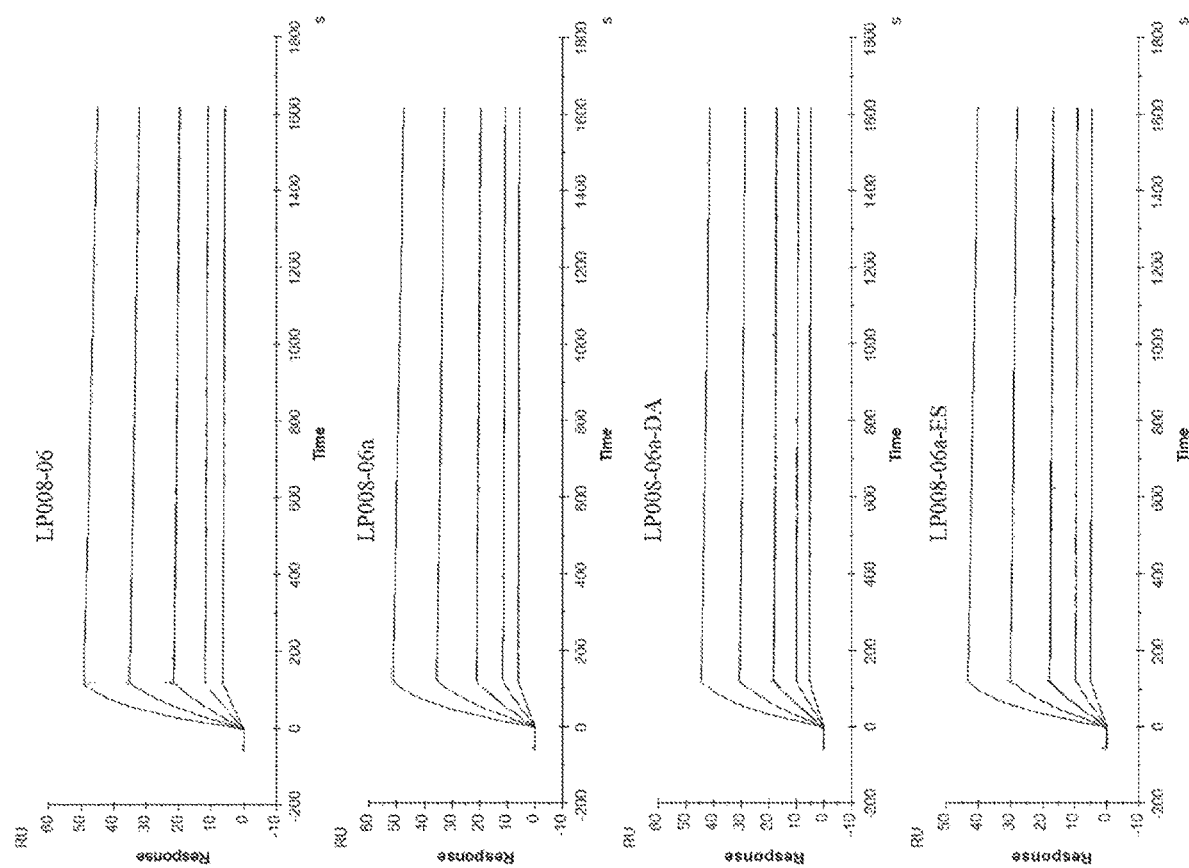
FIG. 10 shows the binding kinetics of LP008-06, LP008-06a, LP008-06a-DA and LP008-06a-ES to recombinant PD-L1.

The bifunctional molecules were captured using Protein A chip. A serial dilution of human PD-L1-his tag protein was injected over captured antibody for 2 mins at a flow rate of 30 µl/min. The antigen was allowed to dissociate for 1500 s. All the experiments were carried out on a Biacore® T200. Data analysis was carried out using Biacore® T200 evaluation software. The results are shown in FIG. 10 and Table 11 below.

TABLE 11

Affinity testing by Biacore ®

Human PD-L1

| Abs | ka (1/Ms) | kd (1/s) | KD (M) |
|---|---|---|---|
| LP008-06 | 7.832E+5 | 5.918E−5 | 7.556E−11 |
| LP008-06a | 6.865E+5 | 5.276E−5 | 7.684E−11 |
| LP008-06a-DA | 6.613E+5 | 4.795E−5 | 7.252E−11 |
| LP008-06a-ES | 8.404E+5 | 5.300E−5 | 6.307E−11 |

The binding of the LP008-02 to recombinant PD-L1 protein and human TGF-β1 was tested with Biacore® using a capture method.

Figure 11:
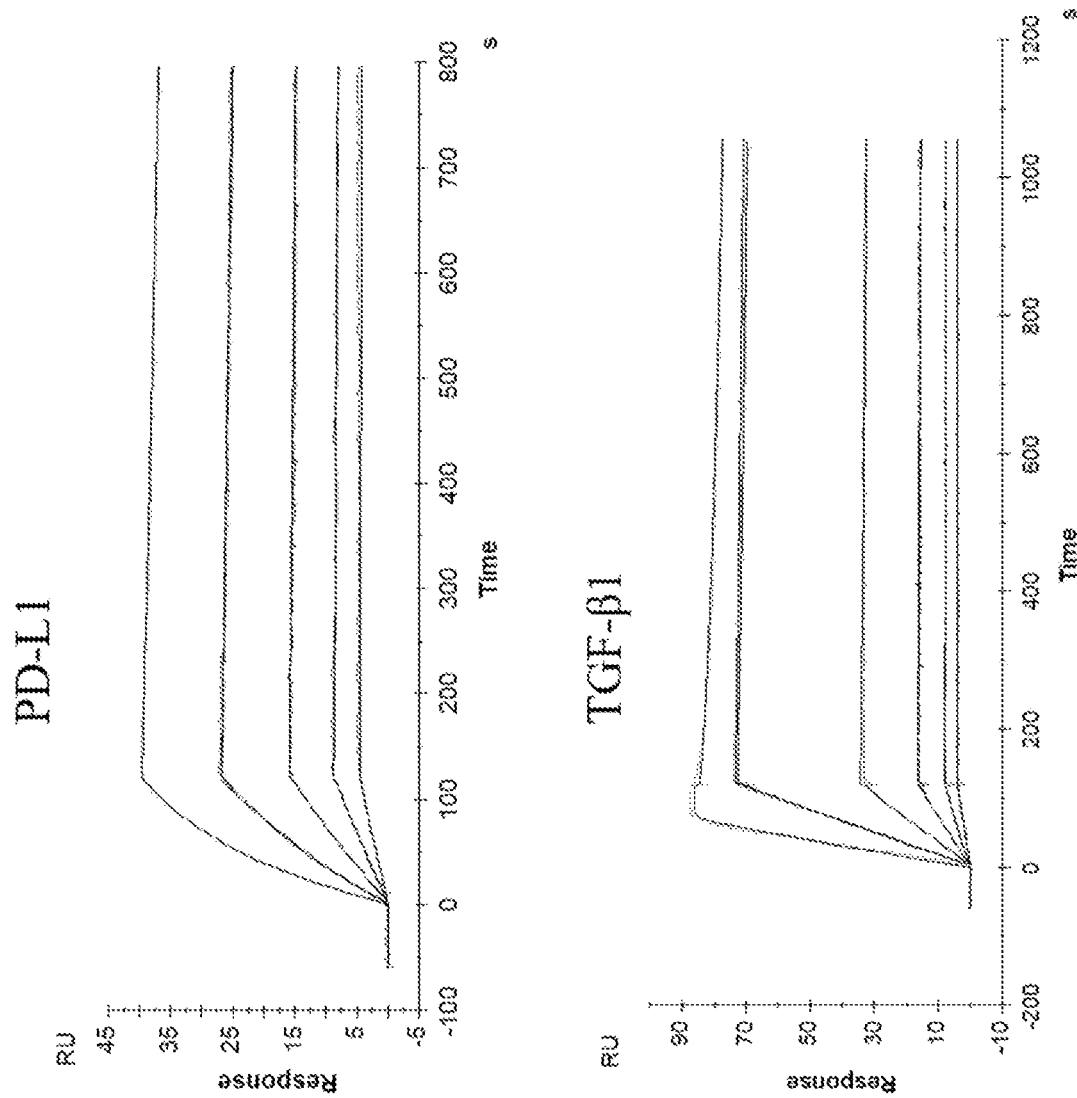
FIG. 11 shows the binding kinetics of LP008-02 to PD-L1 and TGF-0.

LP008-02 was captured using Protein A chip. A serial dilution of human PD-L1-his tag protein and human TGF-β1 was injected over captured antibody for 2 mins at a flow rate of 30 µl/min. PD-L1 was allowed to dissociate for 680 s, and TGF-β1 was allowed to dissociate for 1000 s. All the experiments were carried out on a Biacore T200. Data analysis was carried out using Biacore T200 evaluation software. The result are shown in FIG. 11 and Table 12 below.

TABLE 12

Affinity testing by Biacore ®

LP008-02

| | ka (1/Ms) | kd (1/s) | KD (M) |
|---|---|---|---|
| PD-L1 | 2.528E+6 | 1.044E−4 | 4.130E−11 |
| TGF-β1 | 1.294E+8 | 2.716E−4 | 2.099E−12 |

Example 10: Functional Assay for PD-1/PD-L1 Blockade

The activities of the bifunctional molecules in blocking PD1/PD-L1 interaction were measured with a bioluminescent cell-based assay in this example.

In this assay, when PD1 effector cells and PD-L1 target cells are co-cultured, the PD-1/PD-L1 interaction inhibits TCR signaling and NFAT-RE-mediated luminescence. Addition of either an anti-PD-1 or anti-PD-L1 antibody that blocks the PD-1/PD-L1 interaction releases the inhibitory signal and results in TCR activation and NFAT-RE-mediated luminescence.

Figure 12:
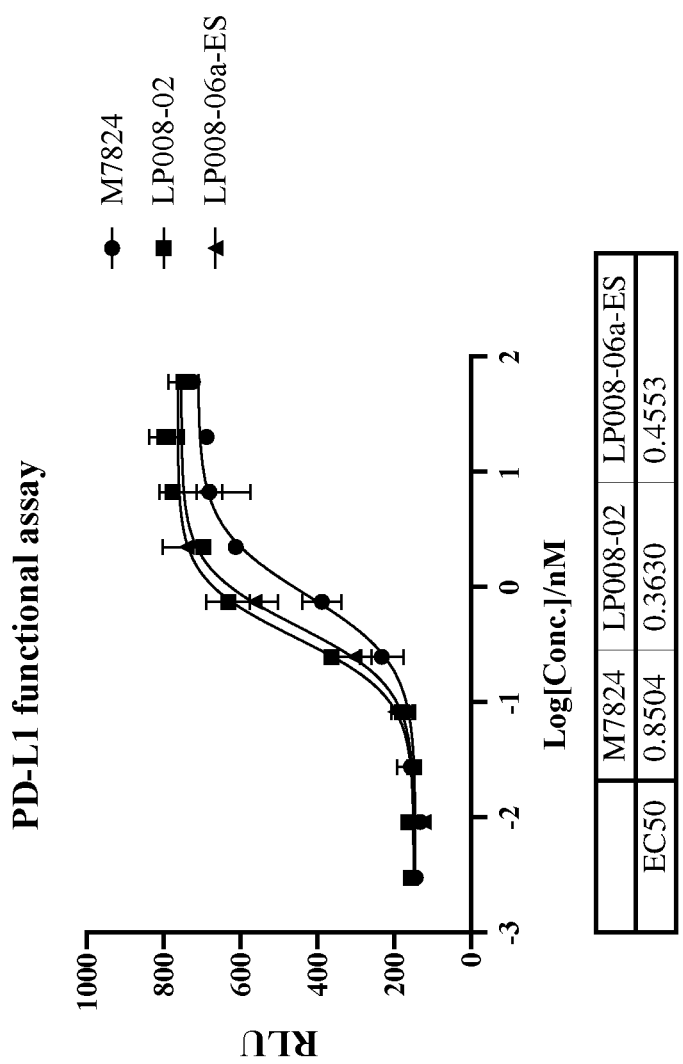
FIG. 12 shows that LP008-02 and LP008-06a-ES can blockade PD1 and PD-L1 interact with higher affinity.

As shown in FIG. 12, LP008-02 and LP008-06a-ES blockaded PD1 and PD-L1 interaction with considerably higher activity than M7824 (M7824 $EC_{50}$=0.8504 nM, LP008-02 $EC_{50}$=0.3630 nM, LP008-06a-ES $EC_{50}$=0.4553 nM).

Example 11: Functional Assay for TGF-β

This example used luciferase assay to evaluate the effect of LP008-02 and LP008-06a-ES on canonical TGF-β signaling.

Serial dilutions of M7824 (bifunctional anti-PD-L1/TGFβ Trap fusion protein, see, e.g., Knudson et al., Oncoimmunology. 2018; 7(5): e1426519), LP008-02 or LP008-06a-ES were incubated with SMAD luciferase reporter-transfected 293 cells for about 20 hours in the presence of recombinant human TGF-β.

Figure 13:
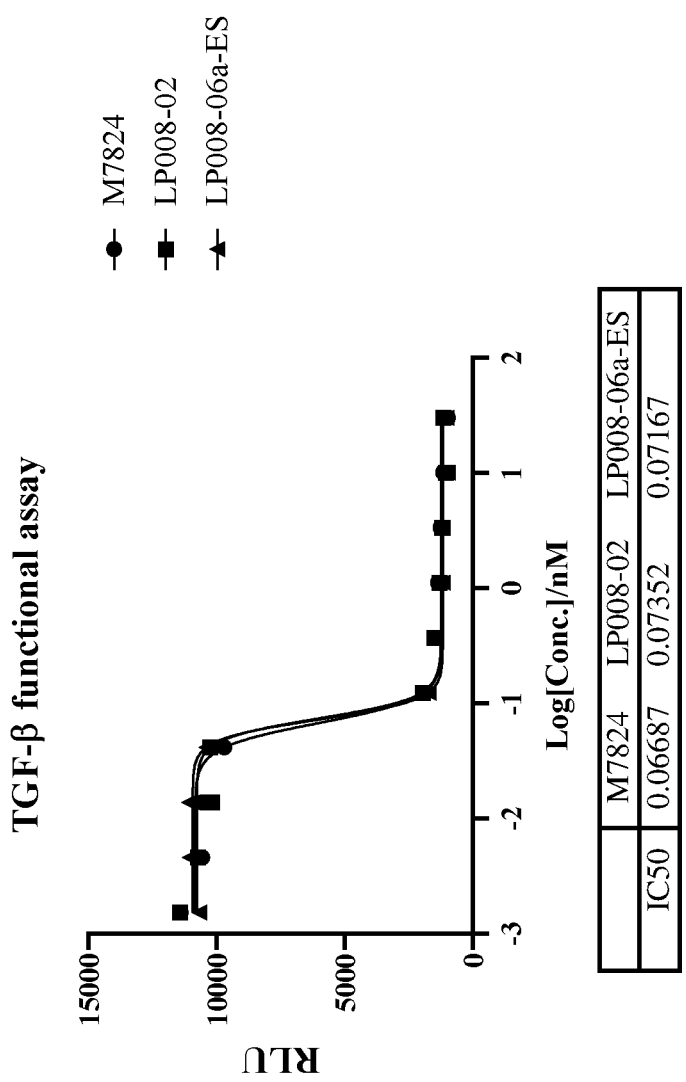
FIG. 13 shows the M7824, LP008-02 and LP008-06a-ES can effectively blocked TGF-β canonical signaling.

As shown in FIG. 13, M7824, LP008-02 and LP008-06a-ES blocked TGF-β canonical signaling (IC50=0.06687 nM, IC50=0.07352 nM, IC50=0.07167 nM) in a TGF-β SMAD luciferase reporter assay in transfected 293 cells.

Example 12: Binding Activity to Human PD-L1

ELISA with Recombinant Human PD-L1

To evaluate the binding activity of M7824, LP008-02, and LP008-06a-ES, the bifunctional molecules were subjected to ELISA test.

Briefly, microtiter plates were coated with human PD-L1-His protein at 0.5 µg/ml in PBS, 100 µl/well at 4° C. overnight, then blocked with 150 µl/well of 1% BSA. Three-fold dilutions of M7824, LP008-02, and LP008-06a-ES starting from 1 µg/ml were added to each well and incubated for 1 hour at 37° C. The plates were washed with PBS/Tween and then incubate with Goat-anti-human IgG antibody conjugated with Horse Radish Peroxidase (HRP) for 30 mins at 37° C. After washing, the plates were developed with TMB substrate and analyzed by spectrophotometer at OD 450 nm.

Figure 14:
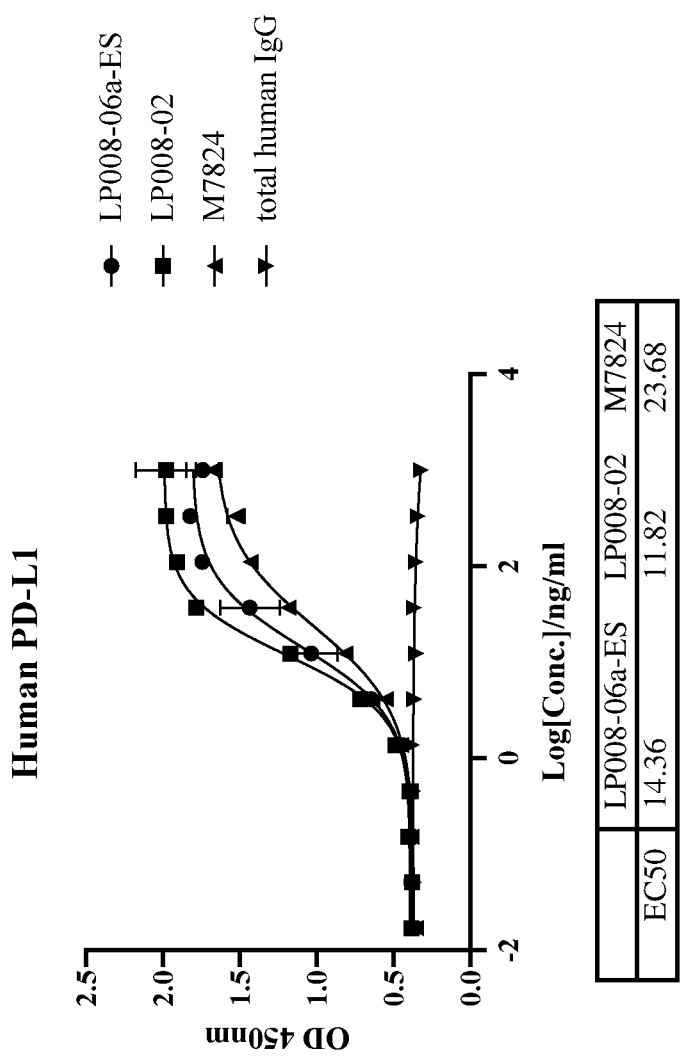
FIG. 14 shows that LP008-02 and LP008-06a-ES bind to human PD-L1 with high affinity.

As shown in FIG. 14, LP008-02 and LP008-06a-ES bound to human PD-L1 with considerably higher activity than M7824 ($EC_{50}$=11.82 ng/ml, and $EC_{50}$=14.36 ng/ml vs. $EC_{50}$=23.68 ng/ml).

Cross Species Activity

To evaluate the binding of bispecific antibodies to Mouse PD-L1, Rat PD-L1, Cynomolgus PD-L1, the antibodies were tested with ELISA.

Briefly, microtiter plates were coated with mouse, rat and cynomolgus PD-L1 protein at 0.5 µg/ml in PBS, 100 µl/well at 4° C. overnight, then blocked with 150 µl/well of 1% BSA. Three-fold dilutions of bispecific antibodies starting from 1 µg/ml were added to each well and incubated for 1 hour at 37° C. The plates were washed with PBS/Tween and then incubate with Goat-anti-human IgG antibody conjugated with Horse Radish Peroxidase (HRP) for 30 mins at 37° C. After washing, the plates were developed with TMB substrate and analyzed by spectrophotometer at OD 450 nm.

Figure 15:
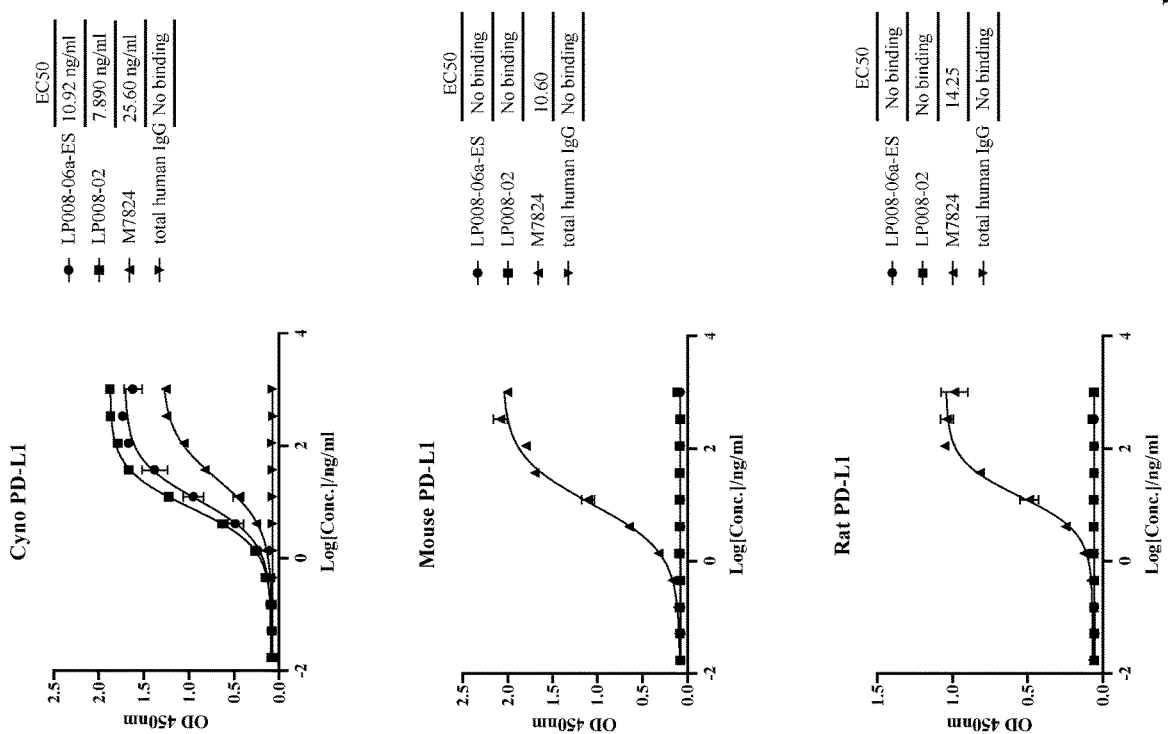
FIG. 15 shows that LP008-02 and LP008-06a-ES can bind to cynomolgus PD-L1 with higher affinity but cannot bind to rat PD-L1 or mouse PD-L1.

LP008-02 and LP008-06a-ES were able to bind to cynomolgus PD-L1 with higher affinity, but only M7824 bound to rat and mouse PD-L1 (FIG. 15 and Table 13).

TABLE 13

| Cross species activity of M7824, CZ010-02, and CZ010-06a-ES | | | |
|---|---|---|---|
| EC50 | Cynomolgus | Rat | Mouse |
| M7824 | 25.60 ng/ml | 14.25 ng/ml | 10.60 ng/ml |
| LP008-02 | 7.890 ng/ml | No binding | No binding |
| LP008-06a-ES | 10.92 ng/ml | No binding | No binding |

Example 13: Binding Activity to Human TGF-β

ELISA by Using Recombinant Human TGF-β

To evaluate the binding activity of M7824, LP008-02, and LP008-06a-ES, these bifunctional molecules were subjected to ELISA test.

Briefly, microtiter plates were coated with human TGF-β protein at 1 µg/ml in PBS, 100 µl/well at 4° C. overnight, then blocked with 150 µl/well of 1% BSA. Three-fold dilutions of the M7824, LP008-02, and LP008-06a-ES bifunctional molecules starting from 10 µg/ml were added to each well and incubated for 1 hour at 37° C. The plates were washed with PBS/Tween and then incubate with Goat-anti-human IgG antibody conjugated with Horse Radish Peroxidase (HRP) for 30 mins at 37° C. After washing, the plates were developed with TMB substrate and analyzed by spectrophotometer at OD 450 nm.

Figure 16:
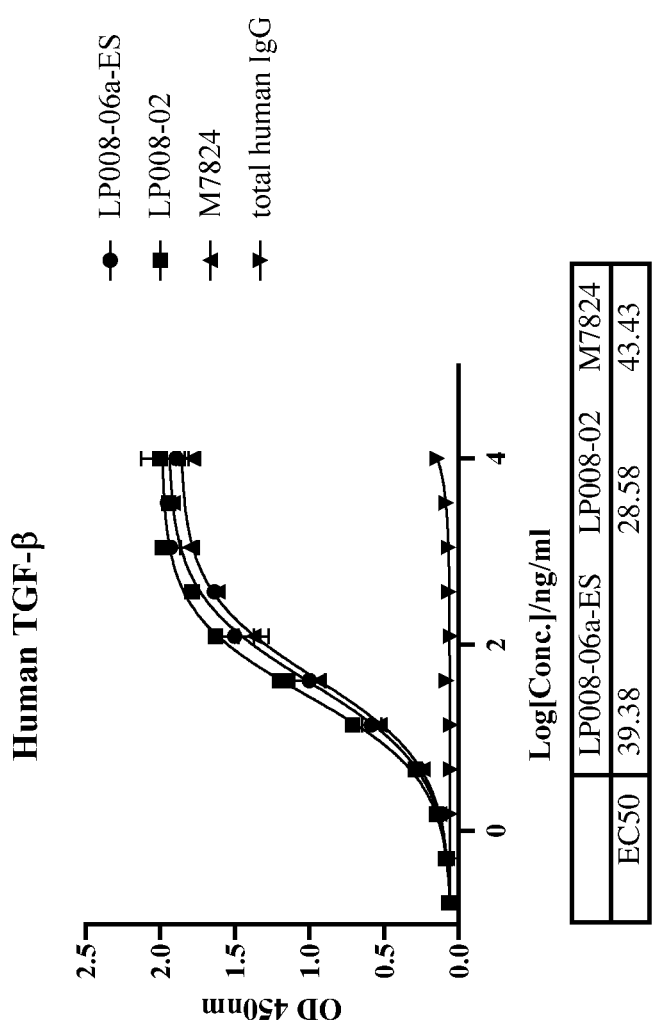
FIG. 16 shows that LP008-02 and LP008-06a-ES had comparable binding efficacy to human TGF-β in contrast to M7824.

As shown in FIG. 16, all of M7824, LP008-02, and LP008-06a-ES bound to human TGF-β with high activity ($EC_{50}$=43.43 ng/ml, $EC_{50}$=28.58 ng/ml, $EC_{50}$=39.38 ng/ml).

Cross Species Activity

To evaluate the binding of bispecific antibodies to Mouse TGF-β, Rat TGF-β, Cynomolgus TGF-β, the bifunctional molecules were performed for the ELISA test.

Briefly, microtiter plates were coated with mouse, rat and cynomolgus TGF-β protein at 1 µg/ml in PBS, 100 µl/well at 4° C. overnight, then blocked with 150 µl/well of 1% BSA. Three-fold dilutions of bispecific antibodies starting from 10 µg/ml were added to each well and incubated for 1 hour at 37° C. The plates were washed with PBS/Tween and then incubate with Goat-anti-human IgG antibody conjugated with Horse Radish Peroxidase (HRP) for 30 mins at 37° C. After washing, the plates were developed with TMB substrate and analyzed by spectrophotometer at OD 450 nm.

Figure 17:
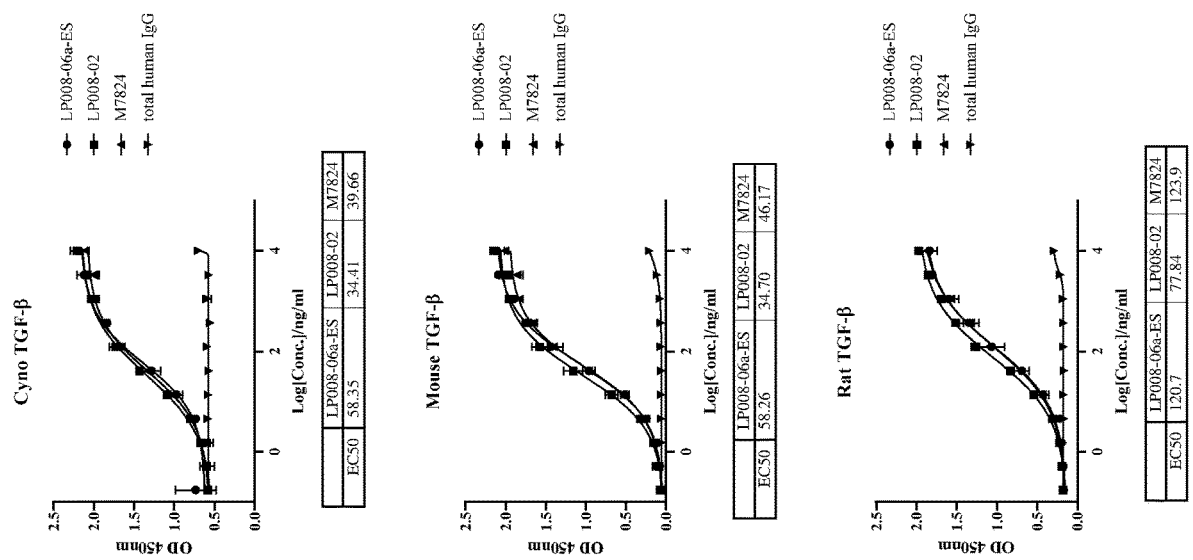
FIG. 17 shows that LP008-02 and LP008-06a-ES had comparable binding efficacy to cynomolgus TGF-β, mouse TGF-β, and rat TGF-β in contrast to M7824.

All of the tested bifunctional molecules bound to cynomolgus, rat, and mouse TGF-β with high affinity (FIG. 17 and Table 14).

TABLE 14

| Cross species activity of M7824, LP008-02, and LP008-06a-ES | | | |
|---|---|---|---|
| EC50 | Cynomolgus | Rat | Mouse |
| M7824 | 39.66 ng/ml | 123.9 ng/ml | 46.17 ng/ml |
| LP008-02 | 34.41 ng/ml | 77.84 ng/ml | 34.70 ng/ml |
| LP008-06a-ES | 58.35 ng/ml | 120.7 ng/ml | 58.26 ng/ml |

Example 14: Efficacy in a MC38 Tumor Mouse Model

This example used a tumor mouse model to test the in vivo efficacy of the bifunctional molecules.

MC38 cells expressing human PD-L1 resuspended in PBS were seeded subcutaneously into right skin of B-hPD-L1 humanized mice at a concentration of $5 \times 10^5$ cells in a volume of 0.2 mL. When the average tumor volume reached approximately 50 mm³, 24 mice with an appropriate individual tumor volume were selected for the group, and the animals were randomly assigned to 4 experimental groups according to the tumor volume, with 6 animals in each group. On the 3rd days after anti-mCD20 mAbs injection, total human IgG, M7824, LP008-02 and LP008-06a-ES were administered 3 times a week by intraperitoneal injection. The dose was calculated based on the experimental animal's body weight at 10 µg/g. Mice weight and tumor size were tested twice a week.

Figure 18A:
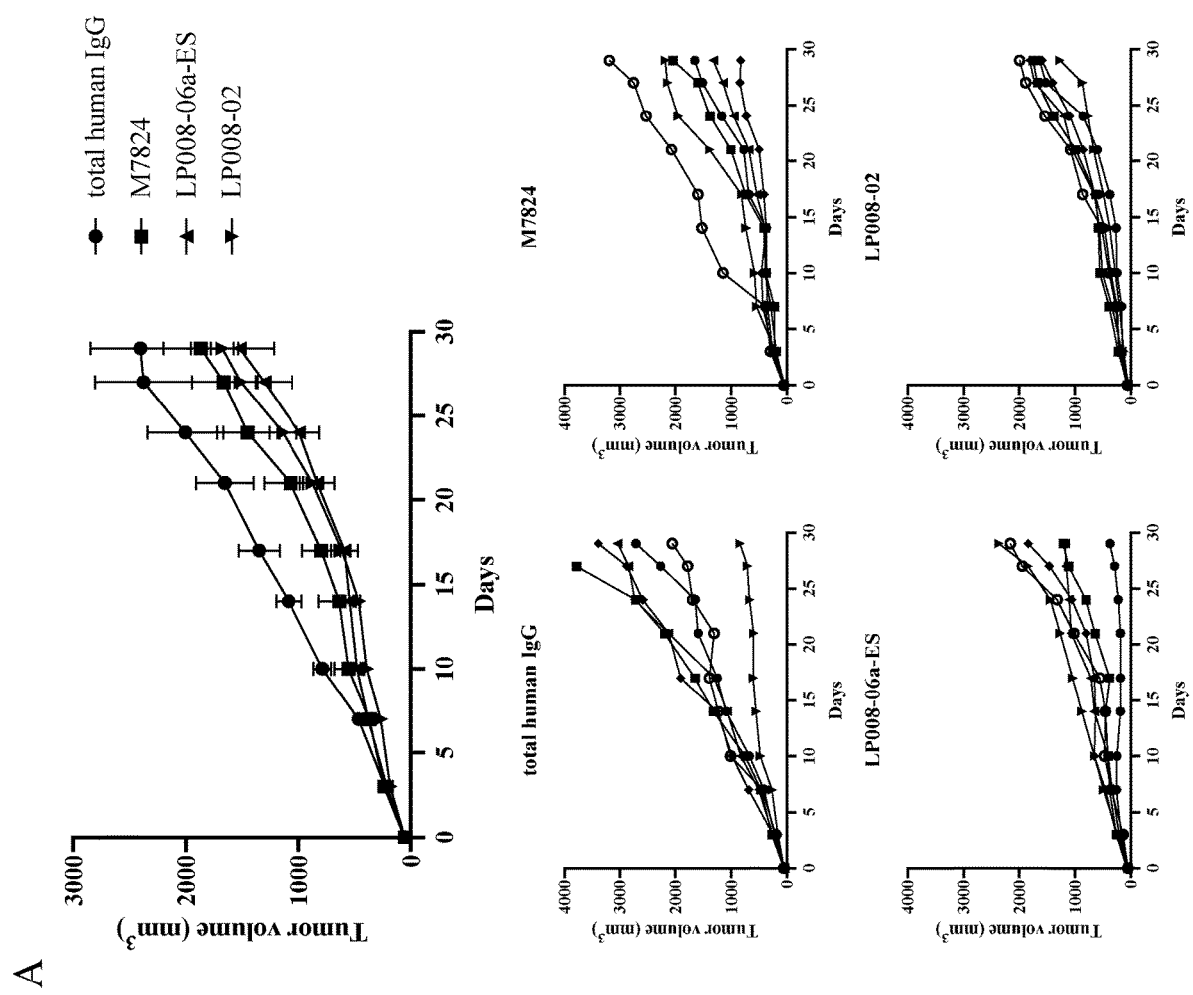
FIG. 18A-B show the drug effects of LP008-02 and LP008-06a-ES in animal models.
Figure 18B:
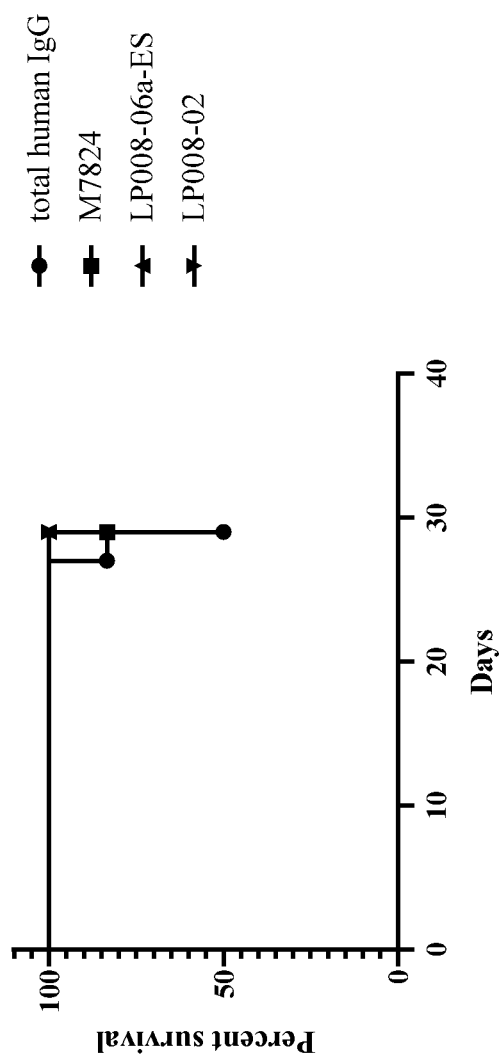

The results are shown in FIG. 18. Bifunctional molecules LP008-02 and LP008-06a-ES exhibited better efficacy than M7824 in these animal models in terms of tumor growth inhibition. Furthermore, animal deaths were observed in both the IgG and M7824 groups, but not in the LP008-02 and LP008-06a-ES groups, demonstrating the greater safety profiles of the new bifunctional molecules.

Example 15. Modification of Bifunctional Molecules

This example tested certain modified bifunctional molecules (Table 15) for their in vivo efficacy of functional assay for TGF-β. Some of them included a linker sequence of TAGHTQTSTGGGAITTGTSGAGHGP (SEQ ID NO:87), HYP, and/or G4S (SEQ ID NO:86) repeats. These molecules are referred to as LP008-02-1 to LP008-02-7, respectively.

TABLE 15

Modified sequences design of linker and TGF-β RII

| Name | Sequences (not showing the antibody portion) | SEQ ID NO: |
|---|---|---|
| 1 | *GGGGSGGGGSGGGGSGGGGSGGGGS*IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 79 |
| 2 | *GGGG*TAGHTQTSTGGGAITTGTSGAGHGPLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 80 |
| 3 | *GGGGSGGGGSGGGGSGGGGSGGGGS*TAGHTQTSTGGGAITTGTSGAGHGPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 81 |
| 4 | *GGGGSGGGGSGGGGSGGGGSGGGGS*TAGHTQTSTGGGAITTGTSGAGHGPQLCKFCDVRFSTCDNQKSCMSNCSITSICEKNEVCVAVWRKNDENITLETVCHDPKLPYHDFILEDAASPKCIMKEKKKPGETFFMCSCSSDECNDNIIFS | 82 |
| 5 | *SGGGGSGGGGSGGGGSGGGGSGGGGS*HYPQLCKFCDVRFSTCDNQKSCMSNCSITSICEKNEVCVAVWRKNDENITLETVCHDPKLPYHDFILEDAASPKCIMKEKKKPGETFFMCSCSSDECNDNIIFS | 83 |
| 6 | *SGGGGSGGGGSGGGGSGGGGSGGGGS*HYPQLCKFCDVRFSTCDNQKSCMSNCSITSICEKNEVCVAVWRKNDENITLETVCHDPKLPYHDFILEDAASPKCIMKEKKKPGETFFMCSCSSDECNDNIIFSEEYNTSNPD | 84 |
| 7 | *GGGGSGGGGSGGGGS*HYPQLCKFCDVRFSTCDNQKSCMSNCSITSICEKNEVCVAVWRKNDENITLETVCHDPKLPYHDFILEDAASPKCIMKEKKKPGETFFMCSCSSDECNDNIIFSEEYNTSNPD | 85 |

ELISA with Recombinant Human TGF-β1

To evaluate the binding activity of modified LP008-02 bifunctional molecules, these bifunctional molecules were tested with ELISA.

Briefly, microtiter plates were coated with human TGF-β1 protein (Acro, TG1-H4212) at 1 µg/ml in PBS, 100 µl/well at 4° C. overnight, then blocked with 150 µl/well of 1% BSA. Three-fold dilutions of modified LP008-02 bifunctional molecules starting from 30 nM were added to each well and incubated for 1 hour at 37° C. The plates were washed with PBS/Tween and then incubate with Goat-anti-human IgG (H+L) antibody conjugated with Horse Radish Peroxidase (HRP) for 30 mins at 37° C. After washing, the plates were developed with TMB substrate and analyzed by spectrophotometer at OD 450 nm.

Figure 19:
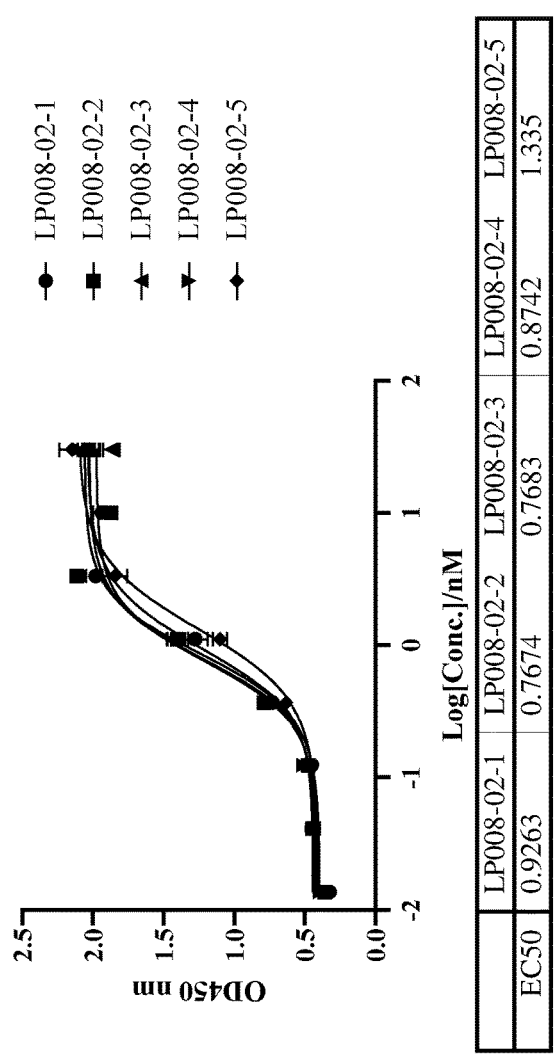
FIG. 19 shows that all tested modified bifunctional molecules had comparable binding efficacy to human TGF-β in contact to LP008-02-1.
Figure 19:
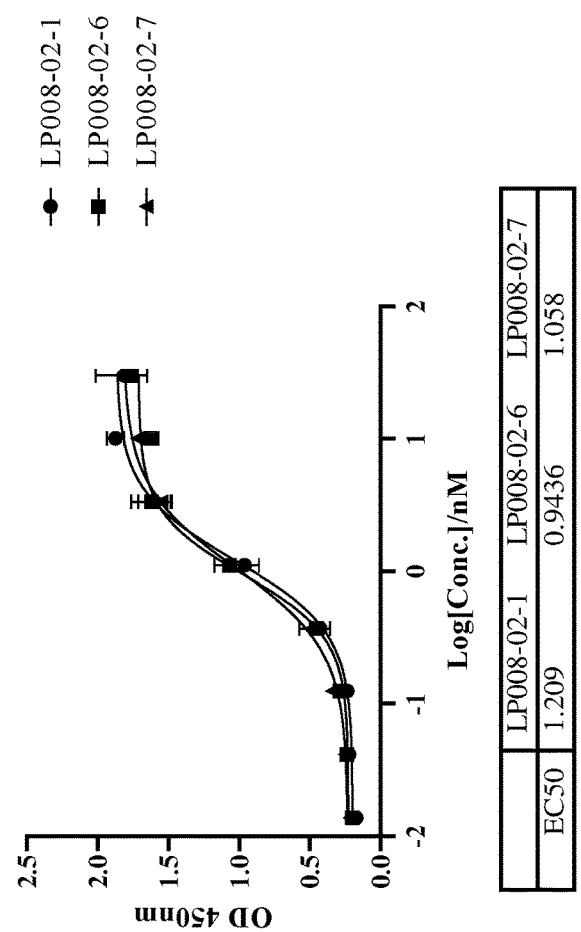

As shown in FIG. 19, all of modified LP008-02 bifunctional molecules bound to human TGF-β1 with high activity, comparable to LP008-02-1.

TGF-β Functional Assay

Serial dilutions of modified LP008-02 bifunctional molecules were incubated with SMAD luciferase reporter-transfected 293 cells for about 22 hours in the presence of recombinant human TGF-β1.

Figure 20:
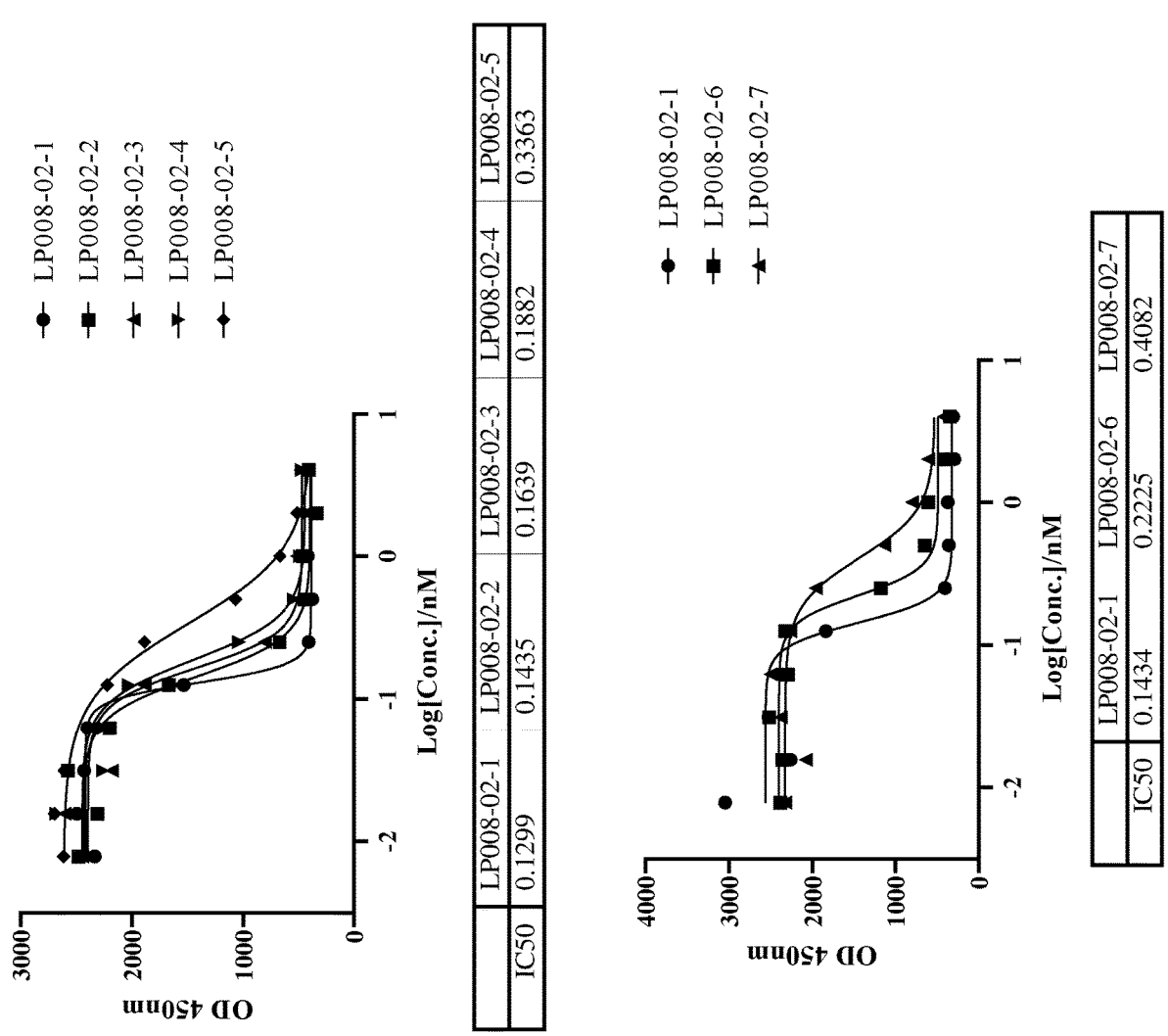
FIG. 20 shows that all tested modified bifunctional molecules can effectively block TGF-β canonical signaling.

As shown in FIG. 20, LP008-02-2, LP008-02-3, and LP008-02-4 effectively blocked TGF-β canonical signaling (IC50=0.1435 nM, IC50=0.1639 nM, IC50=0.1732 nM) in a TGF-β SMAD luciferase reporter assay in transfected 293 cells, which was compared with LP008-02-1.

Example 16. Comparison of the Bifunctional Molecules

The molecules 1-7 of Table 15 included different sequences at the N- and C-terminal ends of the ectodomain (SEQ ID NO:72). They were tested for stability and activity to evaluate the impact of these sequences.

Molecule 1 included the entire excellular portion of the protein (SEQ ID NO:61), which contained 25 amino acids (IPPHVQKSVNNDMIVTDNNGAVKFP, SEQ ID NO:89, or amino acids 24-48 of isoform B, SEQ ID NO:71) from the N-terminus of the extracellular domain, and the C-terminal fragment (EEYNTSNPD, SEQ ID NO:90). In addition, this molecules added a few G4S (SEQ ID NO:86) repeats in the linker.

Molecule 2, compared to Molecule 1, replaced the N-terminal portion (amino acids 24-48 of isoform B, SEQ ID NO:89) of the extracellular domain with an artificial linker TAGHTQTSTGGGAITTGTSGAGHGP (SEQ ID NO:87). This linker was modeled based on SEQ ID NO:89. The changes included (i) removal of the rigid di-peptide PP, (ii) removal of potential cleavage sites QK, N and K, (iii) inclusion of multiple glycine residues to increase flexibility, (iv) partial removal of hydrophobic residues (e.g., retaining only one I). These changes are illustrated in the table below. Molecule 2 also included a single G4S unit at the N-terminus.

```
Original   IPPHVQKSVNNDMIVTDNNGAVKFP   SEQ ID NO: 89

Modified   TAGHTQTSTGGGAITTGTSGAGHGP   SEQ ID NO: 87
```

Molecule 3 included a longer G4S linker than Molecule 2. On top of Molecule 3, Molecule 4 had a deletion of the C-terminal fragment, EEYNTSNPD (SEQ ID NO:90). Molecule 5 replaced the artificial linker, SEQ ID NO:87, with a short linker HYP. Molecules 6 and 7 included different lengths of the G4S linker at the N-terminal side of the HYP linker.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A multifunctional molecule, comprising an anti-PD-L1 (programmed death-ligand 1) antibody or fragment thereof and an extracellular domain of human TGF-β RII (TGF-beta receptor type-2),
wherein the anti-PD-L1 antibody or fragment thereof has specificity to the human PD-L1 protein and comprises a heavy chain variable region (VH) comprising a VH CDR1, a VH CDR2 and a VH CDR3, and a light chain variable region (VL) comprising a VL CDR1, a VL CDR2, and a VL CDR3,
wherein the VH CDR1, VH CDR2, VH CDR3, VL CDR1, VL CDR2, and VL CDR3, respectively, comprise the amino acid sequences of
SEQ ID NO:13-18,
wherein the human TGF-β RII extracellular domain comprises the amino acid sequence of SEQ ID NO:72 and is fused to the anti-PD-L1 antibody or fragment thereof.

2. The multifunctional molecule of claim 1, wherein anti-PD-L1 antibody or fragment thereof comprises a heavy chain that comprises the VH and a separate light chain comprising the VL.

3. The multifunctional molecule of claim 2, wherein the TGF-β RII extracellular domain is fused to the heavy chain of the anti-PD-L1 antibody or fragment thereof.

4. The multifunctional molecule of claim 3, wherein the TGF-β RII extracellular domain is fused to the C-terminus of the heavy chain of the anti-PD-L1 antibody or fragment thereof.

5. The multifunctional molecule of claim 3, wherein the TGF-β RII extracellular domain is fused to the heavy chain of the anti-PD-L1 antibody or fragment thereof through a peptide linker.

6. The multifunctional molecule of claim 1, wherein the TGF-β RII extracellular domain comprises SEQ ID NO:72 and includes at least a partial deletion of amino acid residues 24-48 of SEQ ID NO:71.

7. The multifunctional molecule of claim 1, wherein the TGF-β RII extracellular domain comprises an amino acid sequence selected from the group consisting of SEQ ID NO:61, and 73-78, wherein for SEQ ID NO:74, X is any amino acid except K, S, or N.

8. The multifunctional molecule of claim 1, which includes at least 30 amino acid residues between SEQ ID NO:72 and the anti-PD-L1 antibody or fragment thereof.

9. The multifunctional molecule of claim 1, which includes an alpha helix motif between SEQ ID NO:72 and the anti-PD-L1 antibody or fragment thereof.

10. The multifunctional molecule of claim 1, wherein the VH comprises an amino acid sequence selected from the group consisting of SEQ ID NO:31-37, and the VL comprises an amino acid sequence selected from the group consisting of SEQ ID NO:38-43.

11. The multifunctional molecule of claim 10, wherein the VH comprises the amino acid sequence of SEQ ID NO:34, and the VL comprises the amino acid sequence of SEQ ID NO:43.

12. The multifunctional molecule of claim 1, which comprises a light chain comprising the VL and a light chain constant region, and a heavy chain comprising the VH, a heavy chain constant region, a peptide linker, and the TGF-β RII extracellular domain.

13. The multifunctional molecule of claim 12, wherein the heavy chain constant region comprises the amino acid sequence of SEQ ID NO:59.

14. A method for treating cancer in a patient in need thereof, comprising administering to the patient an effective amount of the multifunctional molecule of claim 1.

15. The method of claim 14, wherein the cancer is a solid tumor.

16. The method of claim 14, wherein the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

* * * * *

SEQUENCE LISTING

```
<160> NUMBER OF SEQ ID NOS: 92

<210> SEQ ID NO 1
<211> LENGTH: 120
<212> TYPE: PRT
<213> ORGANISM: Artificial Sequence
<220> FEATURE:
<223> OTHER INFORMATION: Synthetic

<400> SEQUENCE: 1

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ile Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Thr Met Ile Ala Thr Asn Trp Phe Ala Tyr Trp Gly Gln
            100                 105                 110

Gly Thr Leu Val Thr Val Ser Ala
        115                 120

<210> SEQ ID NO 2
<211> LENGTH: 107
<212> TYPE: PRT
<213> ORGANISM: Artificial Sequence
<220> FEATURE:
<223> OTHER INFORMATION: Synthetic

<400> SEQUENCE: 2

Asp Ile Val Met Thr Gln Ser His Lys Phe Met Ser Thr Ser Val Val
1               5                   10                  15

Asp Arg Val Ser Ile Thr Cys Lys Ala Ser Gln Asp Val Ser Leu Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Ala Leu Thr Ile Ser Ser Val Gln Ala
65                  70                  75                  80

Glu Asp Leu Ala Leu Tyr Tyr Cys Gln Gln His Tyr Ile Thr Pro Trp
                85                  90                  95
```

```
Thr Phe Gly Gly Gly Thr Lys Leu Glu Ile Lys
            100                 105
```

<210> SEQ ID NO 3
<211> LENGTH: 119
<212> TYPE: PRT
<213> ORGANISM: Artificial Sequence
<220> FEATURE:
<223> OTHER INFORMATION: Synthetic

<400> SEQUENCE: 3

```
Gln Val Lys Leu Leu Gln Ser Gly Ala Ala Leu Val Lys Pro Gly Ala
1               5                   10                  15

Ser Val Lys Met Ser Cys Lys Ala Ser Gly Tyr Ile Phe Thr Asp Phe
            20                  25                  30

Trp Val Ser Trp Val Lys Gln Ser His Glu Lys Ser Leu Glu Trp Ile
        35                  40                  45

Gly Glu Ile Tyr Pro Asn Ser Gly Val Ser Arg Tyr Asn Glu Lys Phe
    50                  55                  60

Lys Gly Arg Ala Thr Met Thr Val Asp Lys Ser Thr Ser Thr Ala Tyr
65                  70                  75                  80

Leu Glu Leu Ser Arg Leu Thr Ser Glu Asp Ser Ala Ile Tyr Tyr Cys
                85                  90                  95

Thr Lys Tyr Phe Gly Tyr Thr Tyr Trp Phe Gly Tyr Trp Gly Gln Gly
            100                 105                 110

Thr Leu Val Thr Val Ser Ser
        115
```

<210> SEQ ID NO 4
<211> LENGTH: 106
<212> TYPE: PRT
<213> ORGANISM: Artificial Sequence
<220> FEATURE:
<223> OTHER INFORMATION: Synthetic

<400> SEQUENCE: 4

```
Asp Thr Val Leu Thr Gln Ser Pro Ala Leu Ala Val Ser Leu Gly Gln
1               5                   10                  15

Arg Ile Thr Ile Ser Cys Arg Ala Ser Lys Ser Val Ser Thr Tyr Met
            20                  25                  30

His Trp Tyr Gln Gln Arg Ser Gly Leu Gln Pro Lys Leu Leu Ile Tyr
        35                  40                  45

Ser Ala Ser His Leu Glu Ser Gly Val Pro Ser Arg Phe Ser Gly Ser
    50                  55                  60

Gly Ser Gly Thr Asp Phe Thr Leu Thr Ile Asp Pro Val Glu Ala Asp
65                  70                  75                  80

Asp Ile Ala Asn Tyr Tyr Cys Gln Gln Ser Asn Glu Leu Pro Val Thr
                85                  90                  95

Phe Gly Ser Gly Thr Lys Leu Glu Ile Lys
            100                 105
```

<210> SEQ ID NO 5
<211> LENGTH: 118
<212> TYPE: PRT
<213> ORGANISM: Artificial Sequence
<220> FEATURE:
<223> OTHER INFORMATION: Synthetic

<400> SEQUENCE: 5

```
Glu Val Gln Leu Val Glu Ser Gly Gly Gly Leu Val Gln Pro Gly Arg
```

```
            1               5                  10                 15
        Ser Leu Thr Leu Ser Cys Val Ala Ser Gly Phe Thr Phe Ser Asn Tyr
                        20                  25                 30
        Trp Met Thr Trp Ile Arg Gln Ala Pro Gly Lys Gly Leu Glu Trp Val
                        35                  40                 45
        Ala Ser Ile Thr Asn Thr Gly Ser Ser Thr Phe Tyr Pro Asp Ser Val
                        50                  55                 60
        Lys Gly Arg Phe Thr Ile Ser Arg Asp Asn Thr Arg Ser Thr Leu Phe
        65                      70                  75                 80
        Leu Gln Ile Asn Ser Leu Arg Ser Glu Asp Thr Ala Thr Tyr Tyr Cys
                        85                  90                 95
        Thr Arg Asp Thr Thr Ile Ala Pro Phe Asp Tyr Trp Gly Gln Gly Val
                        100                 105                110
        Met Val Thr Val Ser Ser
                115

<210> SEQ ID NO 6
<211> LENGTH: 106
<212> TYPE: PRT
<213> ORGANISM: Artificial Sequence
<220> FEATURE:
<223> OTHER INFORMATION: Synthetic

<400> SEQUENCE: 6

Asp Ile Gln Met Thr Gln Ser Pro Ser Phe Leu Ser Ala Ser Val Gly
        1               5                  10                 15
        Asp Arg Val Thr Ile Thr Cys Lys Ala Ser Gln Asn Leu Asn Glu Tyr
                        20                  25                 30
        Leu Asn Trp Tyr Gln Gln Lys Leu Gly Glu Ala Pro Lys Arg Leu Ile
                        35                  40                 45
        Tyr Lys Thr Asn Thr Leu Gln Ala Gly Ile Pro Ser Arg Phe Ser Gly
                        50                  55                 60
        Ser Gly Ser Gly Ile Asp Tyr Thr Leu Thr Ile Ser Ser Leu Gln Pro
        65                      70                  75                 80
        Glu Asp Val Ala Thr Tyr Phe Cys Ser Gln Tyr Asn Ser Gly Asn Thr
                        85                  90                 95
        Phe Gly Ala Gly Thr Lys Leu Glu Leu Lys
                        100                 105

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Ser Asp Tyr Ala Trp Asn
        1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic

<400> SEQUENCE: 8

Tyr Ile Ile Tyr Ser Gly Ser Thr Ser Tyr Asn Pro Ser Leu Lys Ser
        1               5                  10                 15
```

<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Ser Thr Met Ile Ala Thr Asn Trp Phe Ala Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Lys Ala Ser Gln Asp Val Ser Leu Ala Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Trp Ala Ser Thr Arg His Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Gln Gln His Tyr Ile Thr Pro Trp Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Asp Phe Trp Val Ser
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Glu Ile Tyr Pro Asn Ser Gly Val Ser Arg Tyr Asn Glu Lys Phe Lys
1               5                   10                  15

Gly

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Tyr Phe Gly Tyr Thr Tyr Trp Phe Gly Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Arg Ala Ser Lys Ser Val Ser Thr Tyr Met His
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Ser Ala Ser His Leu Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Gln Gln Ser Asn Glu Leu Pro Val Thr
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Asn Tyr Trp Met Thr
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic

<400> SEQUENCE: 20

Ser Ile Thr Asn Thr Gly Ser Ser Thr Phe Tyr Pro Asp Ser Val Lys
1               5                   10                  15

Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Asp Thr Thr Ile Ala Pro Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Lys Ala Ser Gln Asn Leu Asn Glu Tyr Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Lys Thr Asn Thr Leu Gln Ala
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Ser Gln Tyr Asn Ser Gly Asn Thr
1               5

<210> SEQ ID NO 25
<211> LENGTH: 120
<212> TYPE: PRT
<213> ORGANISM: Artificial Sequence
<220> FEATURE:
<223> OTHER INFORMATION: Synthetic

<400> SEQUENCE: 25

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ile Tyr Ser Gly Ser Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Glu Asp Thr Ala Thr Tyr Tyr Cys
                85                  90                  95

Ala Arg Ser Thr Met Ile Ala Thr Asn Trp Phe Ala Tyr Trp Gly Gln
            100                 105                 110

Gly Thr Leu Val Thr Val Ser Ala
        115                 120

<210> SEQ ID NO 26
<211> LENGTH: 120
<212> TYPE: PRT
<213> ORGANISM: Artificial Sequence
<220> FEATURE:
<223> OTHER INFORMATION: Synthetic

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ile Tyr Ser Gly Ser Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Met Ile Ala Thr Asn Trp Phe Ala Tyr Trp Gly Gln
            100                 105                 110

Gly Thr Leu Val Thr Val Ser Ser
        115                 120

<210> SEQ ID NO 27
<211> LENGTH: 120
<212> TYPE: PRT
<213> ORGANISM: Artificial Sequence
<220> FEATURE:
<223> OTHER INFORMATION: Synthetic

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Ile Tyr Ser Gly Ser Thr Ser Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Met Ile Ala Thr Asn Trp Phe Ala Tyr Trp Gly Gln
            100                 105                 110

Gly Thr Leu Val Thr Val Ser Ser
        115                 120

```
<210> SEQ ID NO 28
<211> LENGTH: 120
<212> TYPE: PRT
<213> ORGANISM: Artificial Sequence
<220> FEATURE:
<223> OTHER INFORMATION: Synthetic

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Tyr Ile Ile Tyr Ser Gly Ser Thr Ser Tyr Asn Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Met Ile Ala Thr Asn Trp Phe Ala Tyr Trp Gly Gln
            100                 105                 110

Gly Thr Leu Val Thr Val Ser Ser
        115                 120

<210> SEQ ID NO 29
<211> LENGTH: 107
<212> TYPE: PRT
<213> ORGANISM: Artificial Sequence
<220> FEATURE:
<223> OTHER INFORMATION: Synthetic

<400> SEQUENCE: 29

Asp Ile Val Met Thr Gln Ser His Lys Phe Met Ser Thr Ser Val Val
1               5                   10                  15

Asp Arg Val Ser Ile Thr Cys Lys Ala Ser Gln Asp Val Ser Leu Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Ala Leu Thr Ile Ser Ser Val Gln Ala
65                  70                  75                  80

Glu Asp Leu Ala Leu Tyr Tyr Cys Gln Gln His Tyr Ile Thr Pro Trp
                85                  90                  95

Thr Phe Gly Gly Gly Thr Lys Leu Glu Ile Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: Synthetic

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Leu Ala
            20                  25                  30
```

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ile Thr Pro Trp
                85                  90                  95

Thr Phe Gly Gly Gly Thr Lys Val Glu Ile Lys
            100                 105

<210> SEQ ID NO 31
<211> LENGTH: 119
<212> TYPE: PRT
<213> ORGANISM: Artificial Sequence
<220> FEATURE:
<223> OTHER INFORMATION: Synthetic

<400> SEQUENCE: 31

Gln Val Lys Leu Leu Gln Ser Gly Ala Ala Leu Val Lys Pro Gly Ala
1               5                   10                  15

Ser Val Lys Met Ser Cys Lys Ala Ser Gly Tyr Ile Phe Thr Asp Phe
            20                  25                  30

Trp Val Ser Trp Val Lys Gln Ser His Glu Lys Ser Leu Glu Trp Ile
        35                  40                  45

Gly Glu Ile Tyr Pro Asn Ser Gly Val Ser Arg Tyr Asn Glu Lys Phe
    50                  55                  60

Lys Gly Arg Ala Thr Met Thr Val Asp Lys Ser Thr Ser Thr Ala Tyr
65                  70                  75                  80

Leu Glu Leu Ser Arg Leu Thr Ser Glu Asp Ser Ala Ile Tyr Tyr Cys
                85                  90                  95

Thr Lys Tyr Phe Gly Tyr Thr Tyr Trp Phe Gly Tyr Trp Gly Gln Gly
            100                 105                 110

Thr Leu Val Thr Val Ser Ser
        115

<210> SEQ ID NO 32
<211> LENGTH: 119
<212> TYPE: PRT
<213> ORGANISM: Artificial Sequence
<220> FEATURE:
<223> OTHER INFORMATION: Synthetic

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Trp Val Ser Trp Val Arg Gln Ala Pro Gly Gln Gly Leu Glu Trp Met
        35                  40                  45

Gly Glu Ile Tyr Pro Asn Ser Gly Val Ser Arg Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Phe Gly Tyr Thr Tyr Trp Phe Gly Tyr Trp Gly Gln Gly

Thr Leu Val Thr Val Ser Ser
        115

<210> SEQ ID NO 33
<211> LENGTH: 119
<212> TYPE: PRT
<213> ORGANISM: Artificial Sequence
<220> FEATURE:
<223> OTHER INFORMATION: Synthetic

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Trp Val Ser Trp Val Arg Gln Ala Pro Gly Gln Gly Leu Glu Trp Met
        35                  40                  45

Gly Glu Ile Tyr Pro Asn Ser Gly Val Ser Arg Tyr Asn Glu Lys Phe
    50                  55                  60

Lys Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Phe Gly Tyr Thr Tyr Trp Phe Gly Tyr Trp Gly Gln Gly
            100                 105                 110

Thr Leu Val Thr Val Ser Ser
        115

<210> SEQ ID NO 34
<211> LENGTH: 119
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Trp Val Ser Trp Val Arg Gln Ala Pro Gly Gln Gly Leu Glu Trp Met
        35                  40                  45

Gly Glu Ile Tyr Pro Asn Ser Gly Val Ser Arg Tyr Asn Glu Lys Phe
    50                  55                  60

Lys Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Lys Tyr Phe Gly Tyr Thr Tyr Trp Phe Gly Tyr Trp Gly Gln Gly
            100                 105                 110

Thr Leu Val Thr Val Ser Ser
        115

<210> SEQ ID NO 35
<211> LENGTH: 119
<212> TYPE: PRT
<213> ORGANISM: Artificial Sequence
<220> FEATURE:

-continued

<223> OTHER INFORMATION: Synthetic

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Phe
            20                  25                  30

Trp Val Ser Trp Val Arg Gln Ala Pro Gly Gln Gly Leu Glu Trp Ile
        35                  40                  45

Gly Glu Ile Tyr Pro Asn Ser Gly Val Ser Arg Tyr Asn Glu Lys Phe
    50                  55                  60

Lys Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Lys Tyr Phe Gly Tyr Thr Tyr Trp Phe Gly Tyr Trp Gly Gln Gly
            100                 105                 110

Thr Leu Val Thr Val Ser Ser
        115

<210> SEQ ID NO 36
<211> LENGTH: 119
<212> TYPE: PRT
<213> ORGANISM: Artificial Sequence
<220> FEATURE:
<223> OTHER INFORMATION: Synthetic

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Phe
            20                  25                  30

Trp Val Ser Trp Val Arg Gln Ala Pro Gly Gln Gly Leu Glu Trp Ile
        35                  40                  45

Gly Glu Ile Tyr Pro Asn Ser Gly Val Ser Arg Tyr Asn Glu Lys Phe
    50                  55                  60

Lys Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Phe Gly Tyr Thr Tyr Trp Phe Gly Tyr Trp Gly Gln Gly
            100                 105                 110

Thr Leu Val Thr Val Ser Ser
        115

<210> SEQ ID NO 37
<211> LENGTH: 119
<212> TYPE: PRT
<213> ORGANISM: Artificial Sequence
<220> FEATURE:
<223> OTHER INFORMATION: Synthetic

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Phe
            20                  25                  30

Trp Val Ser Trp Val Arg Gln Ala Pro Gly Lys Gly Leu Glu Trp Ile

```
                35                  40                  45
Gly Glu Ile Tyr Pro Asn Ser Gly Val Ser Arg Tyr Asn Glu Lys Phe
 50                  55                  60

Lys Gly Arg Val Thr Met Thr Val Asp Lys Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Lys Tyr Phe Gly Tyr Thr Tyr Trp Phe Gly Tyr Trp Gly Gln Gly
                100                 105                 110

Thr Leu Val Thr Val Ser Ser
        115

<210> SEQ ID NO 38
<211> LENGTH: 106
<212> TYPE: PRT
<213> ORGANISM: Artificial Sequence
<220> FEATURE:
<223> OTHER INFORMATION: Synthetic

<400> SEQUENCE: 38

Asp Thr Val Leu Thr Gln Ser Pro Ala Leu Ala Val Ser Leu Gly Gln
 1                5                  10                  15

Arg Ile Thr Ile Ser Cys Arg Ala Ser Lys Ser Val Ser Thr Tyr Met
                 20                  25                  30

His Trp Tyr Gln Gln Arg Ser Gly Leu Gln Pro Lys Leu Leu Ile Tyr
                 35                  40                  45

Ser Ala Ser His Leu Glu Ser Gly Val Pro Ser Arg Phe Ser Gly Ser
 50                  55                  60

Gly Ser Gly Thr Asp Phe Thr Leu Thr Ile Asp Pro Val Glu Ala Asp
 65                  70                  75                  80

Asp Ile Ala Asn Tyr Tyr Cys Gln Gln Ser Asn Glu Leu Pro Val Thr
                 85                  90                  95

Phe Gly Ser Gly Thr Lys Leu Glu Ile Lys
                100                 105

<210> SEQ ID NO 39
<211> LENGTH: 107
<212> TYPE: PRT
<213> ORGANISM: Artificial Sequence
<220> FEATURE:
<223> OTHER INFORMATION: Synthetic

<400> SEQUENCE: 39

Asp Ile Gln Met Thr Gln Ser Pro Ser Ser Leu Ser Ala Ser Val Gly
 1                5                  10                  15

Asp Arg Val Thr Ile Thr Cys Arg Ala Ser Lys Ser Val Ser Thr Tyr
                 20                  25                  30

Met His Trp Tyr Gln Gln Lys Pro Gly Lys Ala Pro Lys Leu Leu Ile
                 35                  40                  45

Tyr Ser Ala Ser His Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Glu Leu Pro Val
                 85                  90                  95

Thr Phe Gly Gly Gly Thr Lys Val Glu Ile Lys
                100                 105
```

```
<210> SEQ ID NO 40
<211> LENGTH: 107
<212> TYPE: PRT
<213> ORGANISM: Artificial Sequence
<220> FEATURE:
<223> OTHER INFORMATION: Synthetic

<400> SEQUENCE: 40

Asp Thr Val Leu Thr Gln Ser Pro Ser Leu Ser Ala Ser Val Gly
1               5                   10                  15

Asp Arg Val Thr Ile Thr Cys Arg Ala Ser Lys Ser Val Ser Thr Tyr
            20                  25                  30

Met His Trp Tyr Gln Gln Lys Pro Gly Lys Ala Pro Lys Leu Leu Ile
        35                  40                  45

Tyr Ser Ala Ser His Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Glu Leu Pro Val
                85                  90                  95

Thr Phe Gly Gly Gly Thr Lys Val Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Synthetic

<400> SEQUENCE: 41

Asp Thr Val Leu Thr Gln Ser Pro Ser Leu Ser Ala Ser Val Gly
1               5                   10                  15

Asp Arg Val Thr Ile Thr Cys Arg Ala Ser Lys Ser Val Ser Thr Tyr
            20                  25                  30

Met His Trp Tyr Gln Gln Lys Pro Gly Lys Gln Pro Lys Leu Leu Ile
        35                  40                  45

Tyr Ser Ala Ser His Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Glu Leu Pro Val
                85                  90                  95

Thr Phe Gly Gly Gly Thr Lys Val Glu Ile Lys
            100                 105

<210> SEQ ID NO 42
<211> LENGTH: 106
<212> TYPE: PRT
<213> ORGANISM: Artificial Sequence
<220> FEATURE:
<223> OTHER INFORMATION: Synthetic

<400> SEQUENCE: 42

Asp Thr Val Leu Thr Gln Ser Pro Ser Leu Ser Ala Ser Val Gly Asp
1               5                   10                  15

Arg Val Thr Ile Thr Cys Arg Ala Ser Lys Ser Val Ser Thr Tyr Met
            20                  25                  30

His Trp Tyr Gln Gln Lys Pro Gly Lys Gln Pro Lys Leu Leu Ile Tyr
```

```
                35                  40                  45
Ser Ala Ser His Leu Glu Ser Gly Val Pro Ser Arg Phe Gly Ser
         50                  55                  60
Gly Ser Gly Thr Asp Phe Thr Leu Thr Ile Ser Ser Leu Gln Pro Glu
 65                  70                  75                  80
Asp Phe Ala Thr Tyr Tyr Cys Gln Gln Ser Asn Glu Leu Pro Val Thr
                 85                  90                  95
Phe Gly Gly Gly Thr Lys Val Glu Ile Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: Synthetic

<400> SEQUENCE: 43

Asp Ile Gln Met Thr Gln Ser Pro Ser Ser Leu Ser Ala Ser Val Gly
 1               5                  10                  15
Asp Arg Val Thr Ile Thr Cys Arg Ala Ser Lys Ser Val Ser Thr Tyr
             20                  25                  30
Met His Trp Tyr Gln Gln Lys Pro Gly Lys Gln Pro Lys Leu Leu Ile
         35                  40                  45
Tyr Ser Ala Ser His Leu Glu Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Asn Glu Leu Pro Val
                 85                  90                  95
Thr Phe Gly Gly Gly Thr Lys Val Glu Ile Lys
            100                 105

<210> SEQ ID NO 44
<211> LENGTH: 118
<212> TYPE: PRT
<213> ORGANISM: Artificial Sequence
<220> FEATURE:
<223> OTHER INFORMATION: Synthetic

<400> SEQUENCE: 44

Glu Val Gln Leu Val Glu Ser Gly Gly Gly Leu Val Gln Pro Gly Arg
 1               5                  10                  15
Ser Leu Thr Leu Ser Cys Val Ala Ser Gly Phe Thr Phe Ser Asn Tyr
             20                  25                  30
Trp Met Thr Trp Ile Arg Gln Ala Pro Gly Lys Gly Leu Glu Trp Val
         35                  40                  45
Ala Ser Ile Thr Asn Thr Gly Ser Ser Thr Phe Tyr Pro Asp Ser Val
     50                  55                  60
Lys Gly Arg Phe Thr Ile Ser Arg Asp Asn Thr Arg Ser Thr Leu Phe
 65                  70                  75                  80
Leu Gln Ile Asn Ser Leu Arg Ser Glu Asp Thr Ala Thr Tyr Tyr Cys
                 85                  90                  95
Thr Arg Asp Thr Thr Ile Ala Pro Phe Asp Tyr Trp Gly Gln Gly Val
            100                 105                 110
Met Val Thr Val Ser Ser
            115
```

<210> SEQ ID NO 45
<211> LENGTH: 118
<212> TYPE: PRT
<213> ORGANISM: Artificial Sequence
<220> FEATURE:
<223> OTHER INFORMATION: Synthetic

<400> SEQUENCE: 45

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ser Ser Ile Thr Asn Thr Gly Ser Ser Thr Phe Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Thr Ile Ala Pro Phe Asp Tyr Trp Gly Gln Gly Thr
            100                 105                 110

Met Val Thr Val Ser Ser
        115
```

<210> SEQ ID NO 46
<211> LENGTH: 118
<212> TYPE: PRT
<213> ORGANISM: Artificial Sequence
<220> FEATURE:
<223> OTHER INFORMATION: Synthetic

<400> SEQUENCE: 46

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Ser Ile Thr Asn Thr Gly Ser Ser Thr Phe Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Thr Ile Ala Pro Phe Asp Tyr Trp Gly Gln Gly Thr
            100                 105                 110

Met Val Thr Val Ser Ser
        115
```

<210> SEQ ID NO 47
<211> LENGTH: 118
<212> TYPE: PRT
<213> ORGANISM: Artificial Sequence
<220> FEATURE:
<223> OTHER INFORMATION: Synthetic

<400> SEQUENCE: 47

Glu Val Gln Leu Val Glu Ser Gly Gly Gly Leu Val Lys Pro Gly Gly

```
                1               5                   10                  15
            Ser Leu Arg Leu Ser Cys Ala Ala Ser Gly Phe Thr Phe Ser Asn Tyr
                            20                  25                  30

Trp Met Thr Trp Val Arg Gln Ala Pro Gly Lys Gly Leu Glu Trp Val
                        35                  40                  45

Ala Ser Ile Thr Asn Thr Gly Ser Ser Thr Phe Tyr Pro Asp Ser Val
                    50                  55                  60

Lys Gly Arg Phe Thr Ile Ser Arg Asp Asn Ala Lys Asn Ser Leu Tyr
             65                 70                  75                  80

Leu Gln Met Asn Ser Leu Arg Ala Glu Asp Thr Ala Val Tyr Tyr Cys
                            85                  90                  95

Thr Arg Asp Thr Thr Ile Ala Pro Phe Asp Tyr Trp Gly Gln Gly Thr
                        100                 105                 110

Met Val Thr Val Ser Ser
                        115
```

<210> SEQ ID NO 48
<211> LENGTH: 118
<212> TYPE: PRT
<213> ORGANISM: Artificial Sequence
<220> FEATURE:
<223> OTHER INFORMATION: Synthetic

<400> SEQUENCE: 48

```
            Glu Val Gln Leu Val Glu Ser Gly Gly Gly Leu Val Lys Pro Gly Gly
             1              5                   10                  15

Ser Leu Arg Leu Ser Cys Ala Ala Ser Gly Phe Thr Phe Ser Asn Tyr
                            20                  25                  30

Trp Met Thr Trp Ile Arg Gln Ala Pro Gly Lys Gly Leu Glu Trp Val
                        35                  40                  45

Ala Ser Ile Thr Asn Thr Gly Ser Ser Thr Phe Tyr Pro Asp Ser Val
                    50                  55                  60

Lys Gly Arg Phe Thr Ile Ser Arg Asp Asn Ala Lys Asn Ser Leu Tyr
             65                 70                  75                  80

Leu Gln Met Asn Ser Leu Arg Ala Glu Asp Thr Ala Val Tyr Tyr Cys
                            85                  90                  95

Thr Arg Asp Thr Thr Ile Ala Pro Phe Asp Tyr Trp Gly Gln Gly Thr
                        100                 105                 110

Met Val Thr Val Ser Ser
                        115
```

<210> SEQ ID NO 49
<211> LENGTH: 118
<212> TYPE: PRT
<213> ORGANISM: Artificial Sequence
<220> FEATURE:
<223> OTHER INFORMATION: Synthetic

<400> SEQUENCE: 49

```
            Glu Val Gln Leu Val Glu Ser Gly Gly Gly Leu Val Lys Pro Gly Gly
             1              5                   10                  15

Ser Leu Arg Leu Ser Cys Ala Ala Ser Gly Phe Thr Phe Ser Asn Tyr
                            20                  25                  30

Trp Met Thr Trp Ile Arg Gln Ala Pro Gly Lys Gly Leu Glu Trp Val
                        35                  40                  45

Ala Ser Ile Thr Asn Thr Gly Ser Ser Thr Phe Tyr Pro Asp Ser Val
                    50                  55                  60
```

```
Lys Gly Arg Phe Thr Ile Ser Arg Asp Asn Ala Lys Ser Ser Leu Tyr
 65                  70                  75                  80

Leu Gln Met Asn Ser Leu Arg Ala Glu Asp Thr Ala Val Tyr Tyr Cys
                 85                  90                  95

Thr Arg Asp Thr Thr Ile Ala Pro Phe Asp Tyr Trp Gly Gln Gly Thr
            100                 105                 110

Met Val Thr Val Ser Ser
            115
```

<210> SEQ ID NO 50
<211> LENGTH: 106
<212> TYPE: PRT
<213> ORGANISM: Artificial Sequence
<220> FEATURE:
<223> OTHER INFORMATION: Synthetic

<400> SEQUENCE: 50

```
Asp Ile Gln Met Thr Gln Ser Pro Ser Phe Leu Ser Ala Ser Val Gly
 1               5                  10                  15

Asp Arg Val Thr Ile Thr Cys Lys Ala Ser Gln Asn Leu Asn Glu Tyr
             20                  25                  30

Leu Asn Trp Tyr Gln Gln Lys Leu Gly Glu Ala Pro Lys Arg Leu Ile
         35                  40                  45

Tyr Lys Thr Asn Thr Leu Gln Ala Gly Ile Pro Ser Arg Phe Ser Gly
 50                  55                  60

Ser Gly Ser Gly Ile Asp Tyr Thr Leu Thr Ile Ser Ser Leu Gln Pro
 65                  70                  75                  80

Glu Asp Val Ala Thr Tyr Phe Cys Ser Gln Tyr Asn Ser Gly Asn Thr
                 85                  90                  95

Phe Gly Ala Gly Thr Lys Leu Glu Leu Lys
            100                 105
```

<210> SEQ ID NO 51
<211> LENGTH: 106
<212> TYPE: PRT
<213> ORGANISM: Artificial Sequence
<220> FEATURE:
<223> OTHER INFORMATION: Synthetic

<400> SEQUENCE: 51

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Leu Asn Glu Tyr
             20                  25                  30

Leu Asn Trp Tyr Gln Gln Lys Pro Gly Lys Ala Pro Lys Arg Leu Ile
         35                  40                  45

Tyr Lys Thr Asn Thr Leu Gln Ala Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ser Gln Tyr Asn Ser Gly Asn Thr
                 85                  90                  95

Phe Gly Gln Gly Thr Lys Leu Glu Ile Lys
            100                 105
```

<210> SEQ ID NO 52
<211> LENGTH: 106
<212> TYPE: PRT
<213> ORGANISM: Artificial Sequence
<220> FEATURE:
<223> OTHER INFORMATION: Synthetic

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Leu Asn Glu Tyr
            20                  25                  30

Leu Asn Trp Tyr Gln Gln Lys Pro Gly Lys Ala Pro Lys Arg Leu Ile
        35                  40                  45

Tyr Lys Thr Asn Thr Leu Gln Ala Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Ser Gln Tyr Asn Ser Gly Asn Thr
                85                  90                  95

Phe Gly Gln Gly Thr Lys Leu Glu Ile Lys
            100                 105

<210> SEQ ID NO 53
<211> LENGTH: 106
<212> TYPE: PRT
<213> ORGANISM: Artificial Sequence
<220> FEATURE:
<223> OTHER INFORMATION: Synthetic

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Leu Asn Glu Tyr
            20                  25                  30

Leu Asn Trp Tyr Gln Gln Lys Pro Gly Lys Ala Pro Lys Arg Leu Ile
        35                  40                  45

Tyr Lys Thr Asn Thr Leu Gln Ala Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Ser Gln Tyr Asn Ser Gly Asn Thr
                85                  90                  95

Phe Gly Gln Gly Thr Lys Leu Glu Ile Lys
            100                 105

<210> SEQ ID NO 54
<211> LENGTH: 106
<212> TYPE: PRT
<213> ORGANISM: Artificial Sequence
<220> FEATURE:
<223> OTHER INFORMATION: Synthetic

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Leu Asn Glu Tyr
            20                  25                  30

Leu Asn Trp Tyr Gln Gln Lys Pro Gly Lys Ala Pro Lys Arg Leu Ile
        35                  40                  45

Tyr Lys Thr Asn Thr Leu Gln Ala Gly Ile Pro Ser Arg Phe Ser Gly
50                  55                  60

-continued

Ser Gly Ser Gly Ile Asp Tyr Thr Leu Thr Ile Ser Ser Leu Gln Pro
65                  70                  75                  80

Glu Asp Phe Ala Thr Tyr Tyr Cys Ser Gln Tyr Asn Ser Gly Asn Thr
                85                  90                  95

Phe Gly Gln Gly Thr Lys Leu Glu Ile Lys
            100                 105

<210> SEQ ID NO 55
<211> LENGTH: 106
<212> TYPE: PRT
<213> ORGANISM: Artificial Sequence
<220> FEATURE:
<223> OTHER INFORMATION: Synthetic

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Leu Asn Glu Tyr
                20                  25                  30

Leu Asn Trp Tyr Gln Gln Lys Leu Gly Glu Ala Pro Lys Arg Leu Ile
            35                  40                  45

Tyr Lys Thr Asn Thr Leu Gln Ala Gly Ile Pro Ser Arg Phe Ser Gly
50                  55                  60

Ser Gly Ser Gly Ile Asp Tyr Thr Leu Thr Ile Ser Ser Leu Gln Pro
65                  70                  75                  80

Glu Asp Phe Ala Thr Tyr Phe Cys Ser Gln Tyr Asn Ser Gly Asn Thr
                85                  90                  95

Phe Gly Gln Gly Thr Lys Leu Glu Ile Lys
            100                 105

<210> SEQ ID NO 56
<211> LENGTH: 106
<212> TYPE: PRT
<213> ORGANISM: Artificial Sequence
<220> FEATURE:
<223> OTHER INFORMATION: Synthetic

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Leu Asn Glu Tyr
                20                  25                  30

Leu Asn Trp Tyr Gln Gln Lys Pro Gly Lys Ala Pro Lys Arg Leu Ile
            35                  40                  45

Tyr Lys Thr Asn Thr Leu Gln Ala Gly Ile Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Ser Gln Tyr Gln Ser Gly Asn Thr
                85                  90                  95

Phe Gly Gln Gly Thr Lys Leu Glu Ile Lys
            100                 105

<210> SEQ ID NO 57
<211> LENGTH: 118
<212> TYPE: PRT
<213> ORGANISM: Artificial Sequence
<220> FEATURE:
<223> OTHER INFORMATION: Synthetic

<400> SEQUENCE: 57

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Ile Arg Gln Ala Pro Gly Lys Gly Leu Glu Trp Val
        35                  40                  45

Ala Ser Ile Thr Asn Thr Gly Ser Ser Thr Phe Tyr Pro Asp Ala Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Thr Thr Ile Ala Pro Phe Asp Tyr Trp Gly Gln Gly Thr
            100                 105                 110

Met Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Synthetic

<400> SEQUENCE: 58

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Ile Arg Gln Ala Pro Gly Lys Gly Leu Glu Trp Val
        35                  40                  45

Ala Ser Ile Thr Asn Thr Gly Ser Ser Thr Phe Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Thr Thr Ile Ala Pro Phe Asp Tyr Trp Gly Gln Gly Thr
            100                 105                 110

Met Val Thr Val Ser Ser
        115

<210> SEQ ID NO 59
<211> LENGTH: 330
<212> TYPE: PRT
<213> ORGANISM: Artificial Sequence
<220> FEATURE:
<223> OTHER INFORMATION: Synthetic

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

-continued

```
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Ala
                325                 330
```

<210> SEQ ID NO 60
<211> LENGTH: 21
<212> TYPE: PRT
<213> ORGANISM: Artificial Sequence
<220> FEATURE:
<223> OTHER INFORMATION: Synthetic

<400> SEQUENCE: 60

```
Gly Gly Gly Gly Ser Gly Gly Gly Gly Ser Gly Gly Gly Gly Ser Gly
1               5                  10                  15
Gly Gly Gly Ser Gly
            20
```

<210> SEQ ID NO 61
<211> LENGTH: 136
<212> TYPE: PRT
<213> ORGANISM: Artificial Sequence
<220> FEATURE:
<223> OTHER INFORMATION: Synthetic

<400> SEQUENCE: 61

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65              70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp
    130                 135
```

<210> SEQ ID NO 62
<211> LENGTH: 606
<212> TYPE: PRT
<213> ORGANISM: Artificial Sequence
<220> FEATURE:
<223> OTHER INFORMATION: Synthetic

<400> SEQUENCE: 62

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Trp Val Ser Trp Val Arg Gln Ala Pro Gly Gln Gly Leu Glu Trp Met
        35                  40                  45

Gly Glu Ile Tyr Pro Asn Ser Gly Val Ser Arg Tyr Asn Glu Lys Phe
    50                  55                  60

Lys Gly Arg Val Thr Met Thr Val Asp Lys Ser Ile Ser Thr Ala Tyr
65              70                  75                  80

Met Glu Leu Ser Arg Leu Arg Ser Asp Asp Thr Ala Val Tyr Tyr Cys
                85                  90                  95

Thr Lys Tyr Phe Gly Tyr Thr Tyr Trp Phe Gly Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Ala Gly Gly Gly Ser Gly Gly Gly Ser Gly Gly Gly Ser
450                 455                 460

Gly Gly Gly Gly Ser Gly Ile Pro Pro His Val Gln Lys Ser Val Asn
465                 470                 475                 480

Asn Asp Met Ile Val Thr Asp Asn Asn Gly Ala Val Lys Phe Pro Gln
            485                 490                 495

Leu Cys Lys Phe Cys Asp Val Arg Phe Ser Thr Cys Asp Asn Gln Lys
        500                 505                 510

Ser Cys Met Ser Asn Cys Ser Ile Thr Ser Ile Cys Glu Lys Pro Gln
            515                 520                 525

Glu Val Cys Val Ala Val Trp Arg Lys Asn Asp Glu Asn Ile Thr Leu
        530                 535                 540

Glu Thr Val Cys His Asp Pro Lys Leu Pro Tyr His Asp Phe Ile Leu
545                 550                 555                 560

Glu Asp Ala Ala Ser Pro Lys Cys Ile Met Lys Glu Lys Lys Lys Pro
            565                 570                 575

Gly Glu Thr Phe Phe Met Cys Ser Cys Ser Ser Asp Glu Cys Asn Asp
            580                 585                 590

Asn Ile Ile Phe Ser Glu Glu Tyr Asn Thr Ser Asn Pro Asp
        595                 600                 605

<210> SEQ ID NO 63
<211> LENGTH: 605
<212> TYPE: PRT
<213> ORGANISM: Artificial Sequence
<220> FEATURE:

-continued

<223> OTHER INFORMATION: Synthetic

<400> SEQUENCE: 63

```
Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Ile Arg Gln Ala Pro Gly Lys Gly Leu Glu Trp Val
        35                  40                  45

Ala Ser Ile Thr Asn Thr Gly Ser Ser Thr Phe Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Thr Thr Ile Ala Pro Phe Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ala
            435                 440                 445

Gly Gly Gly Gly Ser Gly Gly Gly Gly Ser Gly Gly Gly Gly Ser Gly
        450                 455                 460

Gly Gly Gly Ser Gly Ile Pro Pro His Val Gln Lys Ser Val Asn Asn
465                 470                 475                 480

Asp Met Ile Val Thr Asp Asn Asn Gly Ala Val Lys Phe Pro Gln Leu
                485                 490                 495

Cys Lys Phe Cys Asp Val Arg Phe Ser Thr Cys Asp Asn Gln Lys Ser
                500                 505                 510

Cys Met Ser Asn Cys Ser Ile Thr Ser Ile Cys Glu Lys Pro Gln Glu
            515                 520                 525

Val Cys Val Ala Val Trp Arg Lys Asn Asp Glu Asn Ile Thr Leu Glu
            530                 535                 540

Thr Val Cys His Asp Pro Lys Leu Pro Tyr His Asp Phe Ile Leu Glu
545                 550                 555                 560

Asp Ala Ala Ser Pro Lys Cys Ile Met Lys Glu Lys Lys Pro Gly
                565                 570                 575

Glu Thr Phe Phe Met Cys Ser Cys Ser Ser Asp Glu Cys Asn Asp Asn
                580                 585                 590

Ile Ile Phe Ser Glu Gly Tyr Asn Thr Ser Asn Pro Asp
            595                 600                 605

<210> SEQ ID NO 64
<211> LENGTH: 605
<212> TYPE: PRT
<213> ORGANISM: Artificial Sequence
<220> FEATURE:
<223> OTHER INFORMATION: Synthetic

<400> SEQUENCE: 64

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Ile Arg Gln Ala Pro Gly Lys Gly Leu Glu Trp Val
        35                  40                  45

Ala Ser Ile Thr Asn Thr Gly Ser Ser Thr Phe Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Thr Thr Ile Ala Pro Phe Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175
Ser Ser Gly Leu Tyr Ser Leu Ser Val Val Thr Val Pro Ser Ser
        180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Ala
        435                 440                 445
Gly Gly Gly Gly Ser Gly Gly Gly Gly Ser Gly Gly Gly Gly Ser Gly
        450                 455                 460
Gly Gly Gly Ser Gly Ile Pro Pro His Val Gln Lys Ser Val Asn Asn
465                 470                 475                 480
Asp Met Ile Val Thr Asp Asn Asn Gly Ala Val Lys Phe Pro Gln Leu
                485                 490                 495
Cys Lys Phe Cys Asp Val Arg Phe Ser Thr Cys Asp Asn Gln Lys Ser
            500                 505                 510
Cys Met Ser Asn Cys Ser Ile Thr Ser Ile Cys Glu Lys Pro Gln Glu
        515                 520                 525
Val Cys Val Ala Val Trp Arg Lys Asn Asp Glu Asn Ile Thr Leu Glu
        530                 535                 540
Thr Val Cys His Asp Pro Lys Leu Pro Tyr His Asp Phe Ile Leu Glu
545                 550                 555                 560
Asp Ala Ala Ser Pro Lys Cys Ile Met Lys Glu Lys Lys Lys Pro Gly
                565                 570                 575
Glu Thr Phe Phe Met Cys Ser Cys Ser Ser Asp Glu Cys Asn Asp Asn
```

```
                    580                 585                 590
Ile Ile Phe Ser Glu Glu Tyr Asn Thr Ser Asn Pro Asp
        595                 600                 605

<210> SEQ ID NO 65
<211> LENGTH: 605
<212> TYPE: PRT
<213> ORGANISM: Artificial Sequence
<220> FEATURE:
<223> OTHER INFORMATION: Synthetic

<400> SEQUENCE: 65

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Ile Arg Gln Ala Pro Gly Lys Gly Leu Glu Trp Val
        35                  40                  45

Ala Ser Ile Thr Asn Thr Gly Ser Ser Thr Phe Tyr Pro Asp Ala Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Thr Thr Ile Ala Pro Phe Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
```

```
                    340                 345                 350
    Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
    385                 390                 395                 400

Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Ala
                435                 440                 445

Gly Gly Gly Gly Ser Gly Gly Gly Ser Gly Gly Gly Gly Ser Gly
                450                 455                 460

Gly Gly Gly Ser Gly Ile Pro Pro His Val Gln Lys Ser Val Asn Asn
    465                 470                 475                 480

Asp Met Ile Val Thr Asp Asn Asn Gly Ala Val Lys Phe Pro Gln Leu
                    485                 490                 495

Cys Lys Phe Cys Asp Val Arg Phe Ser Thr Cys Asp Asn Gln Lys Ser
                500                 505                 510

Cys Met Ser Asn Cys Ser Ile Thr Ser Ile Cys Glu Lys Pro Gln Glu
                515                 520                 525

Val Cys Val Ala Val Trp Arg Lys Asn Asp Glu Asn Ile Thr Leu Glu
                530                 535                 540

Thr Val Cys His Asp Pro Lys Leu Pro Tyr His Asp Phe Ile Leu Glu
    545                 550                 555                 560

Asp Ala Ala Ser Pro Lys Cys Ile Met Lys Glu Lys Lys Lys Pro Gly
                    565                 570                 575

Glu Thr Phe Phe Met Cys Ser Cys Ser Ser Asp Glu Cys Asn Asp Asn
                580                 585                 590

Ile Ile Phe Ser Glu Glu Tyr Asn Thr Ser Asn Pro Asp
                595                 600                 605

<210> SEQ ID NO 66
<211> LENGTH: 605
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Ile Arg Gln Ala Pro Gly Lys Gly Leu Glu Trp Val
        35                  40                  45

Ala Ser Ile Thr Asn Thr Gly Ser Ser Thr Phe Tyr Pro Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Thr Thr Ile Ala Pro Phe Asp Tyr Trp Gly Gln Gly Thr
```

```
                100             105             110
Met Val Thr Val Ser Ser Ala Ser Thr Lys Gly Pro Ser Val Phe Pro
                115             120             125

Leu Ala Pro Ser Ser Lys Ser Thr Ser Gly Gly Thr Ala Ala Leu Gly
            130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
                165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
        195             200             205

Asn Thr Lys Val Asp Lys Arg Val Glu Pro Lys Ser Cys Asp Lys Thr
        210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
            245             250             255

Thr Pro Glu Val Thr Cys Val Val Val Asp Val Ser His Glu Asp Pro
            260             265             270

Glu Val Lys Phe Asn Trp Tyr Val Asp Gly Val Glu Val His Asn Ala
        275             280             285

Lys Thr Lys Pro Arg Glu Glu Gln Tyr Asn Ser Thr Tyr Arg Val Val
        290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
                325             330             335

Ile Ser Lys Ala Lys Gly Gln Pro Arg Glu Pro Gln Val Tyr Thr Leu
            340             345             350

Pro Pro Ser Arg Glu Glu Met Thr Lys Asn Gln Val Ser Leu Thr Cys
            355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
                405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Ala
        435             440             445

Gly Gly Gly Gly Ser Gly Gly Gly Ser Gly Gly Gly Gly Ser Gly
        450             455             460

Gly Gly Gly Ser Gly Ile Pro Pro His Val Gln Lys Ser Val Asn Asn
465             470             475             480

Asp Met Ile Val Thr Asp Asn Asn Gly Ala Val Lys Phe Pro Gln Leu
                485             490             495

Cys Lys Phe Cys Asp Val Arg Phe Ser Thr Cys Asp Asn Gln Lys Ser
            500             505             510

Cys Met Ser Asn Cys Ser Ile Thr Ser Ile Cys Glu Lys Pro Gln Glu
        515             520             525
```

```
Val Cys Val Ala Val Trp Arg Lys Asn Asp Glu Asn Ile Thr Leu Glu
    530                 535                 540

Thr Val Cys His Asp Pro Lys Leu Pro Tyr His Asp Phe Ile Leu Glu
545                 550                 555                 560

Asp Ala Ala Ser Pro Lys Cys Ile Met Lys Glu Lys Lys Lys Pro Gly
                565                 570                 575

Glu Thr Phe Phe Met Cys Ser Cys Ser Ser Asp Glu Cys Asn Asp Asn
                580                 585                 590

Ile Ile Phe Ser Glu Glu Tyr Asn Thr Ser Asn Pro Asp
                595                 600                 605

<210> SEQ ID NO 67
<211> LENGTH: 214
<212> TYPE: PRT
<213> ORGANISM: Artificial Sequence
<220> FEATURE:
<223> OTHER INFORMATION: Synthetic

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Tyr
                20                  25                  30

Met His Trp Tyr Gln Gln Lys Pro Gly Lys Gln Pro Lys Leu Leu Ile
            35                  40                  45

Tyr Ser Ala Ser His Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Glu Leu Pro Val
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 68
<211> LENGTH: 213
<212> TYPE: PRT
<213> ORGANISM: Artificial Sequence
<220> FEATURE:
<223> OTHER INFORMATION: Synthetic

<400> SEQUENCE: 68

Asp Ile Gln Met Thr Gln Ser Pro Ser Ser Leu Ser Ala Ser Val Gly
```

```
            1               5                  10                 15
Asp Arg Val Thr Ile Thr Cys Lys Ala Ser Gln Asn Leu Asn Glu Tyr
                20                  25                 30

Leu Asn Trp Tyr Gln Gln Lys Pro Gly Lys Ala Pro Lys Arg Leu Ile
                35                  40                 45

Tyr Lys Thr Asn Thr Leu Gln Ala Gly Ile Pro Ser Arg Phe Ser Gly
                50                  55                 60

Ser Gly Ser Gly Thr Asp Tyr Thr Leu Thr Ile Ser Ser Leu Gln Pro
 65                 70                  75                     80

Glu Asp Phe Ala Thr Tyr Tyr Cys Ser Gln Tyr Asn Ser Gly Asn Thr
                85                  90                 95

Phe Gly Gln Gly Thr Lys Leu Glu Ile Lys Arg Thr Val Ala Ala Pro
                100                 105                110

Ser Val Phe Ile Phe Pro Pro Ser Asp Glu Gln Leu Lys Ser Gly Thr
                115                 120                125

Ala Ser Val Val Cys Leu Leu Asn Asn Phe Tyr Pro Arg Glu Ala Lys
                130                 135                140

Val Gln Trp Lys Val Asp Asn Ala Leu Gln Ser Gly Asn Ser Gln Glu
145                 150                 155                    160

Ser Val Thr Glu Gln Asp Ser Lys Asp Ser Thr Tyr Ser Leu Ser Ser
                165                 170                175

Thr Leu Thr Leu Ser Lys Ala Asp Tyr Glu Lys His Lys Val Tyr Ala
                180                 185                190

Cys Glu Val Thr His Gln Gly Leu Ser Ser Pro Val Thr Lys Ser Phe
                195                 200                205

Asn Arg Gly Glu Cys
210

<210> SEQ ID NO 69
<211> LENGTH: 213
<212> TYPE: PRT
<213> ORGANISM: Artificial Sequence
<220> FEATURE:
<223> OTHER INFORMATION: Synthetic

<400> SEQUENCE: 69

Asp Ile Gln Met Thr Gln Ser Pro Ser Ser Leu Ser Ala Ser Val Gly
 1               5                  10                 15

Asp Arg Val Thr Ile Thr Cys Lys Ala Ser Gln Asn Leu Asn Glu Tyr
                20                  25                 30

Leu Asn Trp Tyr Gln Gln Lys Pro Gly Lys Ala Pro Lys Arg Leu Ile
                35                  40                 45

Tyr Lys Thr Asn Thr Leu Gln Ala Gly Ile Pro Ser Arg Phe Ser Gly
                50                  55                 60

Ser Gly Ser Gly Thr Asp Tyr Thr Leu Thr Ile Ser Ser Leu Gln Pro
 65                 70                  75                     80

Glu Asp Phe Ala Thr Tyr Tyr Cys Ser Gln Tyr Gln Ser Gly Asn Thr
                85                  90                 95

Phe Gly Gln Gly Thr Lys Leu Glu Ile Lys Arg Thr Val Ala Ala Pro
                100                 105                110

Ser Val Phe Ile Phe Pro Pro Ser Asp Glu Gln Leu Lys Ser Gly Thr
                115                 120                125

Ala Ser Val Val Cys Leu Leu Asn Asn Phe Tyr Pro Arg Glu Ala Lys
                130                 135                140

Val Gln Trp Lys Val Asp Asn Ala Leu Gln Ser Gly Asn Ser Gln Glu
```

```
              145                 150                 155                 160
        Ser Val Thr Glu Gln Asp Ser Lys Asp Ser Thr Tyr Ser Leu Ser Ser
                        165                 170                 175

Thr Leu Thr Leu Ser Lys Ala Asp Tyr Glu Lys His Lys Val Tyr Ala
                        180                 185                 190

Cys Glu Val Thr His Gln Gly Leu Ser Ser Pro Val Thr Lys Ser Phe
                        195                 200                 205

Asn Arg Gly Glu Cys
                        210

<210> SEQ ID NO 70
<211> LENGTH: 592
<212> TYPE: PRT
<213> ORGANISM: Artificial Sequence
<220> FEATURE:
<223> OTHER INFORMATION: Synthetic

<400> SEQUENCE: 70

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
                35                  40                  45

Arg Thr Ala His Pro Leu Arg His Ile Asn Asn Asp Met Ile Val Thr
            50                  55                  60

Asp Asn Asn Gly Ala Val Lys Phe Pro Gln Leu Cys Lys Phe Cys Asp
65              70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
                115                 120                 125

Pro Lys Leu Pro Tyr His Asp Phe Ile Leu Glu Asp Ala Ala Ser Pro
            130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
                180                 185                 190

Thr Gly Ile Ser Leu Leu Pro Pro Leu Gly Val Ala Ile Ser Val Ile
                195                 200                 205

Ile Ile Phe Tyr Cys Tyr Arg Val Asn Arg Gln Gln Lys Leu Ser Ser
            210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
```

```
              290                 295                 300
Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 71
<211> LENGTH: 567
<212> TYPE: PRT
<213> ORGANISM: Artificial Sequence
<220> FEATURE:
<223> OTHER INFORMATION: Synthetic

<400> SEQUENCE: 71

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
```

```
             65                  70                  75                  80
        Gln Glu Val Cys Val Ala Val Trp Arg Lys Asn Asp Glu Asn Ile Thr
                             85                  90                  95
        Leu Glu Thr Val Cys His Asp Pro Lys Leu Pro Tyr His Asp Phe Ile
                        100                 105                 110
        Leu Glu Asp Ala Ala Ser Pro Lys Cys Ile Met Lys Glu Lys Lys Lys
                    115                 120                 125
        Pro Gly Glu Thr Phe Phe Met Cys Ser Cys Ser Ser Asp Glu Cys Asn
                130                 135                 140
        Asp Asn Ile Ile Phe Ser Glu Glu Tyr Asn Thr Ser Asn Pro Asp Leu
        145                 150                 155                 160
        Leu Leu Val Ile Phe Gln Val Thr Gly Ile Ser Leu Leu Pro Pro Leu
                            165                 170                 175
        Gly Val Ala Ile Ser Val Ile Ile Phe Tyr Cys Tyr Arg Val Asn
                        180                 185                 190
        Arg Gln Gln Lys Leu Ser Ser Thr Trp Glu Thr Gly Lys Thr Arg Lys
                    195                 200                 205
        Leu Met Glu Phe Ser Glu His Cys Ala Ile Ile Leu Glu Asp Asp Arg
                210                 215                 220
        Ser Asp Ile Ser Ser Thr Cys Ala Asn Asn Ile Asn His Asn Thr Glu
        225                 230                 235                 240
        Leu Leu Pro Ile Glu Leu Asp Thr Leu Val Gly Lys Gly Arg Phe Ala
                            245                 250                 255
        Glu Val Tyr Lys Ala Lys Leu Lys Gln Asn Thr Ser Glu Gln Phe Glu
                        260                 265                 270
        Thr Val Ala Val Lys Ile Phe Pro Tyr Glu Glu Tyr Ala Ser Trp Lys
                    275                 280                 285
        Thr Glu Lys Asp Ile Phe Ser Asp Ile Asn Leu Lys His Glu Asn Ile
                290                 295                 300
        Leu Gln Phe Leu Thr Ala Glu Glu Arg Lys Thr Glu Leu Gly Lys Gln
        305                 310                 315                 320
        Tyr Trp Leu Ile Thr Ala Phe His Ala Lys Gly Asn Leu Gln Glu Tyr
                            325                 330                 335
        Leu Thr Arg His Val Ile Ser Trp Glu Asp Leu Arg Lys Leu Gly Ser
                        340                 345                 350
        Ser Leu Ala Arg Gly Ile Ala His Leu His Ser Asp His Thr Pro Cys
                    355                 360                 365
        Gly Arg Pro Lys Met Pro Ile Val His Arg Asp Leu Lys Ser Ser Asn
                370                 375                 380
        Ile Leu Val Lys Asn Asp Leu Thr Cys Cys Leu Cys Asp Phe Gly Leu
        385                 390                 395                 400
        Ser Leu Arg Leu Asp Pro Thr Leu Ser Val Asp Leu Ala Asn Ser
                            405                 410                 415
        Gly Gln Val Gly Thr Ala Arg Tyr Met Ala Pro Glu Val Leu Glu Ser
                        420                 425                 430
        Arg Met Asn Leu Glu Asn Val Glu Ser Phe Lys Gln Thr Asp Val Tyr
                    435                 440                 445
        Ser Met Ala Leu Val Leu Trp Glu Met Thr Ser Arg Cys Asn Ala Val
                450                 455                 460
        Gly Glu Val Lys Asp Tyr Glu Pro Pro Phe Gly Ser Lys Val Arg Glu
        465                 470                 475                 480
        His Pro Cys Val Glu Ser Met Lys Asp Asn Val Leu Arg Asp Arg Gly
                            485                 490                 495
```

```
Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 72
<211> LENGTH: 102
<212> TYPE: PRT
<213> ORGANISM: Artificial Sequence
<220> FEATURE:
<223> OTHER INFORMATION: Synthetic

<400> SEQUENCE: 72

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe Ser
                100

<210> SEQ ID NO 73
<211> LENGTH: 111
<212> TYPE: PRT
<213> ORGANISM: Artificial Sequence
<220> FEATURE:
<223> OTHER INFORMATION: Synthetic

<400> SEQUENCE: 73

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe Ser Glu Glu Tyr Asn Thr Ser Asn Pro Asp
                100                 105                 110
```

<210> SEQ ID NO 74
<211> LENGTH: 136
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 74

Ile Pro Pro His Val Gln Xaa Xaa Val Asn Asn Asp Met Ile Val Thr
1               5                   10                  15

Asp Asn Xaa Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 75
<211> LENGTH: 136
<212> TYPE: PRT
<213> ORGANISM: Artificial Sequence
<220> FEATURE:
<223> OTHER INFORMATION: Synthetic

<400> SEQUENCE: 75

Thr Ala Gly His Thr Gln Thr Ser Thr Gly Gly Gly Ala Ile Thr Thr
1               5                   10                  15

Gly Thr Ser Gly Ala Gly His Gly Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp

```
              130                 135

<210> SEQ ID NO 76
<211> LENGTH: 127
<212> TYPE: PRT
<213> ORGANISM: Artificial Sequence
<220> FEATURE:
<223> OTHER INFORMATION: Synthetic

<400> SEQUENCE: 76

Thr Ala Gly His Thr Gln Thr Ser Thr Gly Gly Ala Ile Thr Thr
1               5                   10                  15

Gly Thr Ser Gly Ala Gly His Gly Pro Gln Leu Cys Lys Phe Cys Asp
            20                  25                  30

Val Arg Phe Ser Thr Cys Asp Asn Gln Lys Ser Cys Met Ser Asn Cys
                35                  40                  45

Ser Ile Thr Ser Ile Cys Glu Lys Pro Gln Glu Val Cys Val Ala Val
            50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser
        115                 120                 125

<210> SEQ ID NO 77
<211> LENGTH: 105
<212> TYPE: PRT
<213> ORGANISM: Artificial Sequence
<220> FEATURE:
<223> OTHER INFORMATION: Synthetic

<400> SEQUENCE: 77

His Tyr Pro Gln Leu Cys Lys Phe Cys Asp Val Arg Phe Ser Thr Cys
1               5                   10                  15

Asp Asn Gln Lys Ser Cys Met Ser Asn Cys Ser Ile Thr Ser Ile Cys
            20                  25                  30

Glu Lys Pro Gln Glu Val Cys Val Ala Val Trp Arg Lys Asn Asp Glu
            35                  40                  45

Asn Ile Thr Leu Glu Thr Val Cys His Asp Pro Lys Leu Pro Tyr His
        50                  55                  60

Asp Phe Ile Leu Glu Asp Ala Ala Ser Pro Lys Cys Ile Met Lys Glu
65                  70                  75                  80

Lys Lys Pro Gly Glu Thr Phe Phe Met Cys Ser Cys Ser Ser Asp
            85                  90                  95

Glu Cys Asn Asp Asn Ile Ile Phe Ser
            100                 105

<210> SEQ ID NO 78
<211> LENGTH: 114
<212> TYPE: PRT
<213> ORGANISM: Artificial Sequence
<220> FEATURE:
<223> OTHER INFORMATION: Synthetic

<400> SEQUENCE: 78

His Tyr Pro Gln Leu Cys Lys Phe Cys Asp Val Arg Phe Ser Thr Cys
1               5                   10                  15
```

```
Asp Asn Gln Lys Ser Cys Met Ser Asn Cys Ser Ile Thr Ser Ile Cys
            20                  25                  30

Glu Lys Pro Gln Glu Val Cys Val Ala Val Trp Arg Lys Asn Asp Glu
            35                  40                  45

Asn Ile Thr Leu Glu Thr Val Cys His Asp Pro Lys Leu Pro Tyr His
        50                  55                  60

Asp Phe Ile Leu Glu Asp Ala Ala Ser Pro Lys Cys Ile Met Lys Glu
65                  70                  75                  80

Lys Lys Lys Pro Gly Glu Thr Phe Phe Met Cys Ser Cys Ser Ser Asp
                85                  90                  95

Glu Cys Asn Asp Asn Ile Ile Phe Ser Glu Glu Tyr Asn Thr Ser Asn
            100                 105                 110

Pro Asp

<210> SEQ ID NO 79
<211> LENGTH: 157
<212> TYPE: PRT
<213> ORGANISM: Artificial Sequence
<220> FEATURE:
<223> OTHER INFORMATION: Synthetic

<400> SEQUENCE: 79

Gly Gly Gly Gly Ser Gly Gly Gly Ser Gly Gly Gly Ser Gly
1               5                   10                  15

Gly Gly Gly Ser Gly Ile Pro Pro His Val Gln Lys Ser Val Asn Asn
            20                  25                  30

Asp Met Ile Val Thr Asp Asn Gly Ala Val Lys Phe Pro Gln Leu
            35                  40                  45

Cys Lys Phe Cys Asp Val Arg Phe Ser Thr Cys Asp Asn Gln Lys Ser
        50                  55                  60

Cys Met Ser Asn Cys Ser Ile Thr Ser Ile Cys Glu Lys Pro Gln Glu
65                  70                  75                  80

Val Cys Val Ala Val Trp Arg Lys Asn Asp Glu Asn Ile Thr Leu Glu
                85                  90                  95

Thr Val Cys His Asp Pro Lys Leu Pro Tyr His Asp Phe Ile Leu Glu
            100                 105                 110

Asp Ala Ala Ser Pro Lys Cys Ile Met Lys Glu Lys Lys Lys Pro Gly
        115                 120                 125

Glu Thr Phe Phe Met Cys Ser Cys Ser Ser Asp Glu Cys Asn Asp Asn
    130                 135                 140

Ile Ile Phe Ser Glu Glu Tyr Asn Thr Ser Asn Pro Asp
145                 150                 155

<210> SEQ ID NO 80
<211> LENGTH: 141
<212> TYPE: PRT
<213> ORGANISM: Artificial Sequence
<220> FEATURE:
<223> OTHER INFORMATION: Synthetic

<400> SEQUENCE: 80

Gly Gly Gly Gly Ser Thr Ala Gly His Thr Gln Thr Thr Gly Gly
1               5                   10                  15

Gly Ala Ile Thr Thr Gly Thr Ser Gly Ala Gly His Gly Pro Gln Leu
            20                  25                  30

Cys Lys Phe Cys Asp Val Arg Phe Ser Thr Cys Asp Asn Gln Lys Ser
        35                  40                  45
```

```
Cys Met Ser Asn Cys Ser Ile Thr Ser Ile Cys Glu Lys Pro Gln Glu
 50                  55                  60

Val Cys Val Ala Val Trp Arg Lys Asn Asp Glu Asn Ile Thr Leu Glu
 65                  70                  75                  80

Thr Val Cys His Asp Pro Lys Leu Pro Tyr His Asp Phe Ile Leu Glu
                 85                  90                  95

Asp Ala Ala Ser Pro Lys Cys Ile Met Lys Glu Lys Lys Pro Gly
                100                 105                 110

Glu Thr Phe Phe Met Cys Ser Cys Ser Ser Asp Glu Cys Asn Asp Asn
        115                 120                 125

Ile Ile Phe Ser Glu Glu Tyr Asn Thr Ser Asn Pro Asp
        130                 135                 140

<210> SEQ ID NO 81
<211> LENGTH: 161
<212> TYPE: PRT
<213> ORGANISM: Artificial Sequence
<220> FEATURE:
<223> OTHER INFORMATION: Synthetic

<400> SEQUENCE: 81

Gly Gly Gly Gly Ser Gly Gly Gly Ser Gly Gly Gly Gly Ser Gly
  1               5                  10                  15

Gly Gly Ser Gly Gly Gly Ser Thr Ala Gly His Thr Gln Thr
                 20                  25                  30

Ser Thr Gly Gly Gly Ala Ile Thr Thr Gly Thr Ser Gly Ala Gly His
            35                  40                  45

Gly Pro Gln Leu Cys Lys Phe Cys Asp Val Arg Phe Ser Thr Cys Asp
 50                  55                  60

Asn Gln Lys Ser Cys Met Ser Asn Cys Ser Ile Thr Ser Ile Cys Glu
 65                  70                  75                  80

Lys Pro Gln Glu Val Cys Val Ala Val Trp Arg Lys Asn Asp Glu Asn
                 85                  90                  95

Ile Thr Leu Glu Thr Val Cys His Asp Pro Lys Leu Pro Tyr His Asp
                100                 105                 110

Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
        130                 135                 140

Cys Asn Asp Asn Ile Ile Phe Ser Glu Glu Tyr Asn Thr Ser Asn Pro
145                 150                 155                 160

Asp

<210> SEQ ID NO 82
<211> LENGTH: 152
<212> TYPE: PRT
<213> ORGANISM: Artificial Sequence
<220> FEATURE:
<223> OTHER INFORMATION: Synthetic

<400> SEQUENCE: 82

Gly Gly Gly Gly Ser Gly Gly Gly Ser Gly Gly Gly Gly Ser Gly
  1               5                  10                  15

Gly Gly Ser Gly Gly Gly Ser Thr Ala Gly His Thr Gln Thr
                 20                  25                  30

Ser Thr Gly Gly Gly Ala Ile Thr Thr Gly Thr Ser Gly Ala Gly His
            35                  40                  45
```

```
Gly Pro Gln Leu Cys Lys Phe Cys Asp Val Arg Phe Ser Thr Cys Asp
    50                  55                  60
Asn Gln Lys Ser Cys Met Ser Asn Cys Ser Ile Thr Ser Ile Cys Glu
65                  70                  75                  80
Lys Pro Gln Glu Val Cys Val Ala Val Trp Arg Lys Asn Asp Glu Asn
                85                  90                  95
Ile Thr Leu Glu Thr Val Cys His Asp Pro Lys Leu Pro Tyr His Asp
                100                 105                 110
Phe Ile Leu Glu Asp Ala Ala Ser Pro Lys Cys Ile Met Lys Glu Lys
            115                 120                 125
Lys Lys Pro Gly Glu Thr Phe Phe Met Cys Ser Cys Ser Ser Asp Glu
        130                 135                 140
Cys Asn Asp Asn Ile Ile Phe Ser
145                 150

<210> SEQ ID NO 83
<211> LENGTH: 131
<212> TYPE: PRT
<213> ORGANISM: Artificial Sequence
<220> FEATURE:
<223> OTHER INFORMATION: Synthetic

<400> SEQUENCE: 83

Ser Gly Gly Gly Gly Ser Gly Gly Gly Gly Ser Gly Gly Gly Gly Ser
1               5                   10                  15
Gly Gly Gly Gly Ser Gly Gly Gly Gly Ser His Tyr Pro Gln Leu Cys
                20                  25                  30
Lys Phe Cys Asp Val Arg Phe Ser Thr Cys Asp Asn Gln Lys Ser Cys
            35                  40                  45
Met Ser Asn Cys Ser Ile Thr Ser Ile Cys Glu Lys Pro Gln Glu Val
        50                  55                  60
Cys Val Ala Val Trp Arg Lys Asn Asp Glu Asn Ile Thr Leu Glu Thr
65                  70                  75                  80
Val Cys His Asp Pro Lys Leu Pro Tyr His Asp Phe Ile Leu Glu Asp
                85                  90                  95
Ala Ala Ser Pro Lys Cys Ile Met Lys Glu Lys Lys Lys Pro Gly Glu
            100                 105                 110
Thr Phe Phe Met Cys Ser Cys Ser Ser Asp Glu Cys Asn Asp Asn Ile
        115                 120                 125
Ile Phe Ser
    130

<210> SEQ ID NO 84
<211> LENGTH: 140
<212> TYPE: PRT
<213> ORGANISM: Artificial Sequence
<220> FEATURE:
<223> OTHER INFORMATION: Synthetic

<400> SEQUENCE: 84

Ser Gly Gly Gly Gly Ser Gly Gly Gly Gly Ser Gly Gly Gly Gly Ser
1               5                   10                  15
Gly Gly Gly Gly Ser Gly Gly Gly Gly Ser His Tyr Pro Gln Leu Cys
                20                  25                  30
Lys Phe Cys Asp Val Arg Phe Ser Thr Cys Asp Asn Gln Lys Ser Cys
            35                  40                  45
Met Ser Asn Cys Ser Ile Thr Ser Ile Cys Glu Lys Pro Gln Glu Val
```

```
               50                  55                  60
Cys Val Ala Val Trp Arg Lys Asn Asp Glu Asn Ile Thr Leu Glu Thr
 65                  70                  75                  80

Val Cys His Asp Pro Lys Leu Pro Tyr His Asp Phe Ile Leu Glu Asp
                 85                  90                  95

Ala Ala Ser Pro Lys Cys Ile Met Lys Lys Lys Pro Gly Glu
                100                 105                 110

Thr Phe Phe Met Cys Ser Cys Ser Ser Asp Glu Cys Asn Asp Asn Ile
            115                 120                 125

Ile Phe Ser Glu Glu Tyr Asn Thr Ser Asn Pro Asp
        130                 135                 140
```

<210> SEQ ID NO 85
<211> LENGTH: 129
<212> TYPE: PRT
<213> ORGANISM: Artificial Sequence
<220> FEATURE:
<223> OTHER INFORMATION: Synthetic

<400> SEQUENCE: 85

```
Gly Gly Gly Gly Ser Gly Gly Gly Ser Gly Gly Gly Ser His
 1               5                  10                  15

Tyr Pro Gln Leu Cys Lys Phe Cys Asp Val Arg Phe Ser Thr Cys Asp
                 20                  25                  30

Asn Gln Lys Ser Cys Met Ser Asn Cys Ser Ile Thr Ser Ile Cys Glu
             35                  40                  45

Lys Pro Gln Glu Val Cys Val Ala Val Trp Arg Lys Asn Asp Glu Asn
 50                  55                  60

Ile Thr Leu Glu Thr Val Cys His Asp Pro Lys Leu Pro Tyr His Asp
 65                  70                  75                  80

Phe Ile Leu Glu Asp Ala Ala Ser Pro Lys Cys Ile Met Lys Glu Lys
                 85                  90                  95

Lys Lys Pro Gly Glu Thr Phe Phe Met Cys Ser Cys Ser Ser Asp Glu
            100                 105                 110

Cys Asn Asp Asn Ile Ile Phe Ser Glu Glu Tyr Asn Thr Ser Asn Pro
        115                 120                 125

Asp
```

<210> SEQ ID NO 86
<211> LENGTH: 5
<212> TYPE: PRT
<213> ORGANISM: Artificial Sequence
<220> FEATURE:
<223> OTHER INFORMATION: Synthetic

<400> SEQUENCE: 86

```
Gly Gly Gly Gly Ser
 1               5
```

<210> SEQ ID NO 87
<211> LENGTH: 25
<212> TYPE: PRT
<213> ORGANISM: Artificial Sequence
<220> FEATURE:
<223> OTHER INFORMATION: Synthetic

<400> SEQUENCE: 87

```
Thr Ala Gly His Thr Gln Thr Ser Thr Gly Gly Ala Ile Thr Thr
 1               5                  10                  15
```

Gly Thr Ser Gly Ala Gly His Gly Pro
            20                  25

<210> SEQ ID NO 88
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 88

Ile Pro Pro His Val Gln Xaa Xaa Val Asn Asn Asp Met Ile Val Thr
1               5                   10                  15

Asp Asn Xaa Gly Ala Val Lys Phe Pro
            20                  25

<210> SEQ ID NO 89
<211> LENGTH: 25
<212> TYPE: PRT
<213> ORGANISM: Artificial Sequence
<220> FEATURE:
<223> OTHER INFORMATION: Synthetic

<400> SEQUENCE: 89

Ile Pro Pro His Val Gln Lys Ser Val Asn Asn Asp Met Ile Val Thr
1               5                   10                  15

Asp Asn Asn Gly Ala Val Lys Phe Pro
            20                  25

<210> SEQ ID NO 90
<211> LENGTH: 9
<212> TYPE: PRT
<213> ORGANISM: Artificial Sequence
<220> FEATURE:
<223> OTHER INFORMATION: Synthetic

<400> SEQUENCE: 90

Glu Glu Tyr Asn Thr Ser Asn Pro Asp
1               5

<210> SEQ ID NO 91
<211> LENGTH: 17
<212> TYPE: PRT
<213> ORGANISM: Artificial Sequence
<220> FEATURE:
<223> OTHER INFORMATION: Synthetic

<400> SEQUENCE: 91

Ser Ile Thr Asn Thr Gly Ser Ser Thr Phe Tyr Pro Asp Ala Val Lys
1               5                   10                  15

Gly

<210> SEQ ID NO 92
<211> LENGTH: 17
<212> TYPE: PRT
<213> ORGANISM: Artificial Sequence
<220> FEATURE:
<223> OTHER INFORMATION: Synthetic

```
<400> SEQUENCE: 92

Ser Ile Thr Asn Thr Gly Ser Ser Thr Phe Tyr Pro Glu Ser Val Lys
1               5                   10                  15
Gly
```